United States Patent [19]

Amara et al.

[11] Patent Number: 5,658,782

[45] Date of Patent: Aug. 19, 1997

[54] AMINO ACID TRANSPORTERS AND USES

[75] Inventors: Susan G. Amara; Jeffrey L. Arriza, both of Portland, Oreg.

[73] Assignee: State of Oregon, Acting by and Through the Oregon State Board of Higher Education on Behalf of the Oregon Health Sciences University a non-profit organization, Portland, Oreg.

[21] Appl. No.: 140,729

[22] Filed: Oct. 20, 1993

[51] Int. Cl.$^6$ .............................. C12N 5/00; C12N 15/00; C07K 1/00; C07H 21/04

[52] U.S. Cl. ............... 435/365; 435/320.1; 435/325; 435/361; 435/367; 435/369; 435/364; 530/350; 536/23.5; 536/24.31

[58] Field of Search ......................... 435/240.2, 320.1; 530/350; 536/24.31, 23.5

[56] References Cited

U.S. PATENT DOCUMENTS 5,424,185  6/1995  Lam et al. ................... 435/6

OTHER PUBLICATIONS

Arriza et al. (1994) J. Neurosci. 14(9): 5559–5569.
Kanai et al. (1992) Nature 360: 467–471.
Kanai et al. (1993) Trends in Neurosci. 16(9): 365–370.
Kanai et al. (1993) FASEB J. 7: 1450–1459.
Kanner (1993) FEBS Lett. 325(1,2): 95–99.
Pines et al. (1992) Nature 360: 464–467.
Schloss et al. (1992) FEBS Lett. 307(1): 76–80.
Shashidharan et al. (1993) Biochim. Biophys. Acta 1216: 161–164.
Stelzner et al. (1993) FASEB J. 7(4/part 2): A575.
Storck et al. (1992) Proc. Natl. Acad. Sci. USA 89: 10955–10959.
Uhl (1992) Trends in Neurosci. 15(7): 265–268.

*Primary Examiner*—Robert A. Wax
*Assistant Examiner*—Lisa J. Hobbs
*Attorney, Agent, or Firm*—Banner & Allegretti, Ltd.

[57] ABSTRACT

The present invention relates to novel mammalian amino acid transporter proteins and the genes that encode such proteins. The invention is directed toward the isolation, characterization and pharmacological use of the human amino acid transporter proteins EAAT1, EAAT2, EAAT3 and ASCT1. The invention specifically provides isolated complementary DNA copies of mRNA corresponding to each of these transporter genes. Also provided are recombinant expression constructs capable of expressing each of the amino acid transporter genes of the invention in cultures of transformed prokaryotic and eukaryotic cells, as well as such cultures of transformed cells that synthesize the human amino acid transporter proteins encoded therein. The invention also provides methods for screening in vitro compounds having transport-modulating properties using preparations of transporter proteins from such cultures of cells transformed with recombinant expression constructs.

6 Claims, 42 Drawing Sheets

FIG. 1A

```
CACCTCTAGC  TCGGAGCGGC  GTGTAGCGCC                                                                                    54

ATG  GAG  AAG  AGC  AAC  GAG  ACC  AAC
                                    Met  Glu  Lys  Ser  Asn  Glu  Thr  Asn
                                     1                 5
GGC  TAC  CTT  GAC  AGC  GCT  CAG  GCG  GGG  CCC  GGA  GCT                                                           102
Gly  Tyr  Leu  Asp  Ser  Ala  Gln  Ala  Gly  Pro  Gly  Ala
     10                      15                 20
CCG  GGG  ACC  GCG  GCG  GGA  CGC  GCA  CGT  TGC  GCG  CGG                                                           150
Pro  Gly  Thr  Ala  Ala  Gly  Arg  Ala  Arg  Cys  Arg  Arg
 25                      30                 35                 40
CGC  CAA  GCG  CTG  GTG  CTG  CTC  TCC  GGG  GCG  CTG  GCG                                                           198
Arg  Gln  Ala  Leu  Val  Leu  Leu  Ser  Gly  Ala  Leu  Ala
          45                 50                 55
GGC  CTG  GGC  GCG  GCG  TTG  CGC  AGC  CTG  CTC  GTC                                                                246
Gly  Leu  Gly  Ala  Ala  Leu  Arg  Ser  Leu  Leu  Val
 65                      70
ACC  TAC  CTG  GCC  TTC  GCC  GGC  GAG  ATG  CGC  CTC  ATG                                                           294
Thr  Tyr  Leu  Ala  Phe  Pro  Gly  Glu  Met  Arg  Leu  Met
          75                      80                 85
ATC  CTG  CCG  CTG  GTC  TGC  AGC  GTG  CTG  GCC  TCG                                                                342
Ile  Leu  Pro  Leu  Val  Cys  Ser  Val  Leu  Ala  Ser
 90                 95                 100
```

FIG. 1B

```
CTC GAT GCC AGC TGC CTC GGG CGT CTG GGC ATC CGT GTC GCC TAC           390
Leu Asp Ala Ser Cys Leu Gly Arg Leu Gly Ile Arg Val Ala Tyr
105             110             115             120

TTT GGC CTC ACC ACA CTG AGT CTG GCG CTC GCC TCG GCC TTG GCG           438
Phe Gly Leu Thr Thr Leu Ser Leu Ala Leu Ala Ser Ala Leu Ala
                125             130             135

TTC ATC AAG CCA GGA TCC GGT CCA GCG CAG ACC CTT GCC TCC GAC           486
Phe Ile Lys Pro Gly Ser Gly Pro Ala Gln Thr Leu Ala Ser Asp
    140             145             150

CTG GGG GAG GAC TCG GGG CTG CCT CCT GTC CCC AAA GAG ACG GTG           534
Leu Gly Glu Asp Ser Gly Leu Pro Pro Val Pro Lys Glu Thr Val
155             160             165

TCT TTC CTC GAC AAC AGA AAC CTG TTT CCC TCC AAT CTT GTG               582
Ser Phe Leu Asp Asn Arg Asn Leu Phe Pro Ser Asn Leu Val
170             175             180

GTT GCT TTC GAT GCA ACC CGT ACG TAT GAT TAT AAG GTC ACC CAG           630
Val Ala Phe Asp Ala Thr Arg Thr Tyr Asp Tyr Lys Val Thr Gln
185             190             195             200

AGC AGC TCT GGA AAT GTA CGT CAT ACC GAA AAG CCC ATA GGC ACT           678
Ser Ser Ser Gly Asn Val Arg His Thr Glu Lys Pro Ile Gly Thr
        205             210             215
```

FIG. 1C

Row ending at position 726:
GAG Glu, ATA Ile, GAA Glu, GGG Gly (220), ATG Met, AAC Asn, ATT Ile, TTA Leu, GGA Gly (225), TTG Leu, GTC Val, CTG Leu, TTT Phe, GCT Ala (230), CTG Leu, GTG Val Row ending at position 774:
TTA Leu, CGA Gly, GTG Val (235), GCC Ala, TTA Leu, AAG Lys, CTA Leu (240), GGC Gly, TCC Ser, GAA Glu, GGA Gly (245), GAC Asp, CTC Leu, ATC Ile Row ending at position 822:
CGT Arg, TTC Phe (250), AAT Asn, TCC Ser, CTC Leu, AAC Asn (255), GAG Glu, GCG Ala, ACG Thr, GTG Val (260), ATG Met, TCC Ser, TGG Trp Row ending at position 870:
ATT Ile (265), ATG Met, TAC Tyr, GTA Val, CCT Pro (270), GTG Val, GGC Gly, ATC Ile, TTC Phe (275), ATG Met, CCT Leu, GTT Val, GGA Gly, AGC Ser, AAG Lys (280)

Row ending at position 918:
ATC Ile, GTG Val, GAA Glu, ATG Met, AAA Lys (285), GAC Asp, ATC Ile, ATG Met, CTG Leu (290), GTG Val, ACC Thr, AGC Ser, CTG Leu, GGA Gly, GGG Gly (295), AAA Lys Row ending at position 966:
TAC Tyr, ATC Ile, TCT Ser, ATA Ile, TTG Leu, GGC Gly, CAT His (305), GTT Val, ATT Ile, CAT His, GGA Gly (310), CTG Leu, ATT Ile, GTT Val Row ending at position 1014:
CTG Leu, CCA Pro (315), ATT Ile, TAT Tyr, TTT Phe, GTT Val, TTC Phe (320), ACA Thr, CGA Arg, AAA Lys, AAC Asn, CCA Pro (325), TTC Phe, AGA Arg, TTC Phe

FIG. 1D

```
CTC  GGC  CTG  CTC  GCC  CCA  TTT  GCG  ACA  GCA  TTT  GCT  ACC  TGC  TCC                1062
Leu  Gly  Leu  Leu  Ala  Pro  Phe  Ala  Thr  Ala  Phe  Ala  Thr  Cys  Ser
          330            335                      340

AGC  GCG  TCA  ACC  CTT  CCC  TCT  ATG  ATG  AAG  TGC  ATT  GAA  GAG  AAC  AAT           1110
Ser  Ala  Ser  Thr  Leu  Pro  Ser  Met  Met  Lys  Cys  Ile  Glu  Glu  Asn  Asn
345                      350                      355                      360

GGT  GAC  AAG  AGG  AGC  AGG  TTT  ATT  ATC  AAC  GCC  GGG  GCC                          1158
Gly  Asp  Lys  Arg  Ser  Arg  Phe  Ile  Ile  Asn  Ala  Gly  Ala
               365                      370                 375

GTG  ATG  GAC  GGA  GCA  ATC  GCC  CCC  CTC  CAG  TGT  GCC  ATC  GGG  ACC                1206
Val  Met  Asp  Gly  Ala  Ile  Ala  Pro  Leu  Gln  Cys  Ala  Ile  Gly  Thr
                    380                      385                      390

ATT  AAC  CTC  AAC  CTC  TCC  GAG  ATA  GCC  CAG  ATT  TTC  GTG  TTC                     1254
Ile  Asn  Leu  Asn  Leu  Ser  Glu  Ile  Ala  Gln  Ile  Phe  Val  Phe
                         395                      400                      405

ATT  CAA  ACT  GCG  TCC  AGT  GTT  GGA  GCA  GCA  GAG  GGC  GTG  ACC                     1302
Ile  Gln  Thr  Ala  Ser  Ser  Val  Gly  Ala  Ala  Glu  Gly  Val  Thr
410                      415                      420

GCT  GGG  GTC  CTC  ACC  ATT  GCC  ATT  ATC  CTG  CTG  GCC  ATT  GGG  CCA  CTG           1350
Ala  Gly  Val  Leu  Thr  Ile  Ala  Ile  Ile  Leu  Leu  Ala  Ile  Gly  Pro  Leu
425                      430                      435                      440
```

FIG. 1E

```
CCT ACT CAT GAC CTG CCT CTG ATC GCT GTG GAC TGG ATT GTG GAC          1398
Pro Thr His Asp Leu Pro Leu Ile Ala Val Asp Trp Ile Val Asp
            445             450             455

CGG ACC ACG ACC CTG GTG GTG AAT GTG GAG GGG GAT GCC CTG GGT GCA GGC  1446
Arg Thr Thr Thr Leu Val Val Asn Val Glu Gly Asp Ala Leu Gly Ala Gly
        460                 465             470

ATT CTC CAC CAC CTG AAT CAG AAG CTG GCA ACA AAG TGG GGC GAG GAA       1494
Ile Leu His His Leu Asn Gln Lys Leu Ala Thr Lys Trp Gly Glu Glu
        475             480             485

CTT GCT GAG GTG AAA GTG GAA GCC ATC CCC AAC TGC AAG TCT GAG GAG       1542
Leu Ala Glu Val Lys Val Glu Ala Ile Pro Asn Cys Lys Ser Glu Glu
        490             495             500

ACA TCG CCC CTG CTG GTG GTG ACA CAG CAC AAC CCC GCT GTG CCC GCC       1590
Thr Ser Pro Leu Leu Val Val Thr Gln His Asn Pro Ala Val Pro Ala
505             510             515             520

AGT GCC CCA GAA CTG GAA TCC AAG GAG TCG GTT CTG TGATGGGGCT            1636
Ser Ala Pro Glu Leu Glu Ser Lys Glu Ser Val Leu
            525             530

GGGCTTTGGG CTTGCCTGCC AGCAGTGATG TCCCACCCTG TTCA                      1680
```

FIG. 2A

```
AAAGAAGAGA CCCTCCTAGA AAAGTAAAAT ATG ACT AAA AGC AAT GGA GAA GAG      54
                                 Met Thr Lys Ser Asn Gly Glu Glu
                                   1                   5

CCC AAG ATG GGG GGC ATG GAG AGA TTC CAG CAG GGA CTG CGT AAA         102
Pro Lys Met Gly Gly Met Glu Arg Phe Gln Gln Gly Val Arg Lys
     10              15                  20

CGC ACA CTT TTG GCC AGG AAG AAA GTG CAG AAC GCT ACA AAG GAG GTT    150
Arg Thr Leu Leu Ala Arg Lys Lys Val Gln Asn Ala Thr Lys Glu Val
 25              30                  35              40

GTT AAA AGT TAC CTG AAT TTT CGG ATT GCT TTT ACC CTG GTC ACC        198
Val Lys Ser Tyr Leu Asn Phe Arg Ile Ala Phe Thr Leu Val Thr
             45                  50                  55

GCT ATT GTG GGT GGA GAA ATC ACA TTT TTC TCC CTC CGA CTC TAC AGA    246
Ala Ile Val Gly Gly Glu Ile Thr Phe Phe Ser Leu Arg Leu Tyr Arg
         60              65                  70

ATG AGC TAC CGG GAA AAG TAC TTC TCC TTT CCT CCT GGG GAA CTT CTG    294
Met Ser Tyr Arg Glu Lys Tyr Phe Ser Phe Pro Pro Gly Glu Leu Leu
     75              80                  85

ATG AGG TTA CAG ATG CTG GTC TTA CCA CTT ATC TCC AGT CTT           342
Met Arg Leu Gln Met Leu Val Leu Pro Leu Ile Ile Ser Leu
 90              95                  100
```

FIG. 2B

```
GTC ACA GGA ATG GCG GCG CTA GAT AGT AAG GCA TCA GGG AAG TGG GAA     390
Val Thr Gly Met Ala Ala Leu Asp Ser Lys Ala Ser Gly Lys Trp Glu
105             110             115             120

TGC GGA GCT GTA GTC TAT ATG ACC ACC ATT GCT GTA ACC ATT GTG AAG     438
Cys Gly Ala Val Val Tyr Met Thr Thr Ile Ala Val Thr Ile Val Lys
        125             130             135

ATT GGC ATA ATC ATT GTC ATC ATC ATC CAT CCT GGG AAG GGC ACA GAT     486
Ile Gly Ile Ile Ile Val Ile Ile Ile His Pro Gly Lys Gly Thr Asp
            140             145             150

GAA AAC ATG CAC AGA GAA GGC AAA GTA CGA ACA GTG AAG GCA CTG GAA     534
Glu Asn Met His Arg Glu Gly Lys Val Arg Thr Val Lys Ala Leu Glu
        155             160             165

GCC TTC ATG GAC TTG ATC AGG AAC ATG TTA AAT CCA AAT AGC GTA AAA     582
Ala Phe Met Asp Leu Ile Arg Asn Met Leu Asn Pro Asn Ser Val Lys
    170             175             180             
                                                    (195?)

GCC TGC ATG GAG TTT AAC TTT ACC AAC TAT GAG AAG AGA AGC TTT AAT     630
Ala Cys Gln Gln Phe Asn Phe Thr Asn Tyr Glu Lys Arg Ser Phe Asn
185             190             195             200

GTG CCC ATC GAG AAC GAA ACG CCT GTG GGT GCT GTG ATA AAC
Val Pro Ile Gln Ala Glu Thr Leu Val Gly Ala Val Ile Asn             678
                205             210             215
```

Row-end nucleotide positions: 390, 438, 486, 534, 582, 630, 678

FIG. 2C

| | | | | | | | | | | | | | | | | |
|---|---|---|---|---|---|---|---|---|---|---|---|---|---|---|---|---|
| GTG<br>Val | TCT<br>Ser | GAG<br>Glu | GCC<br>Ala<br>220 | ATG<br>Met | GAG<br>Glu | ACT<br>Thr | CTT<br>Leu | ACC<br>Thr<br>225 | CGA<br>Arg | ATC<br>Ile | ACA<br>Thr | GAG<br>Glu | GAG<br>Glu<br>230 | CTG<br>Leu | GTC<br>Val | 726 |
| CCA<br>Pro | GTT<br>Val | CCA<br>Pro<br>235 | GGA<br>Gly | TCT<br>Ser | GTG<br>Val | AAT<br>Asn | GGA<br>Gly<br>240 | GTC<br>Val | AAT<br>Asn | GCC<br>Ala | CTG<br>Leu | GGT<br>Gly<br>245 | CTA<br>Leu | GTT<br>Val | GTC<br>Val | 774 |
| TTC<br>Phe | TCC<br>Ser<br>250 | ATG<br>Met | TGC<br>Cys | TTC<br>Phe | GGT<br>Gly | TTT<br>Phe<br>255 | ATT<br>Ile | GGA<br>Gly | GTG<br>Val | ATG<br>Met<br>260 | AAC<br>Asn | AAG<br>Lys | GAA<br>Glu | CAG<br>Gln | GGG<br>Gly | 822 |
| GAG<br>Gln<br>265 | GCC<br>Ala | CTG<br>Leu | AGA<br>Arg | GAG<br>Glu | TTC<br>Phe<br>270 | TTT<br>Phe | GAT<br>Asp | TCT<br>Ser | CTT<br>Leu | AAC<br>Asn<br>275 | GAA<br>Glu | GCC<br>Ala | ATC<br>Ile | ATG<br>Met | AGA<br>Arg<br>280 | 870 |
| CTG<br>Leu | GTA<br>Val | GCA<br>Ala | ATA<br>Ile<br>285 | ATG<br>Met | TGG<br>Trp | TAT<br>Tyr | GCC<br>Ala | CCC<br>Pro<br>290 | CTT<br>Leu | GGT<br>Gly | GGT<br>Gly | ATT<br>Ile | TTC<br>Phe<br>295 | ATG<br>Met | CTG<br>Leu | 918 |
| ATT<br>Ile | GCT<br>Ala | GGG<br>Gly | AAG<br>Lys<br>300 | ATG<br>Met | GAG<br>Glu | GAA<br>Glu<br>305 | GAC<br>Asp | ATG<br>Met | GGT<br>Gly | ATT<br>Ile<br>310 | GTG<br>Val | GGG<br>Gly | GGG<br>Gly | | | 966 |
| CAG<br>Gln | CTT<br>Leu | GCC<br>Ala<br>315 | ATG<br>Met | TAC<br>Tyr | GTG<br>Val | ACC<br>Thr | ACT<br>Thr<br>320 | ATT<br>Ile | GTT<br>Val | GTC<br>Val | GGC<br>Gly | TTA<br>Leu<br>325 | CTC<br>Leu | ATT<br>Ile | CAC<br>His | 1014 |

FIG. 2D

```
GCA  GTC  ATC  GTC  TTG  CCA  CTC  CTC  TAC  TTC  TTG  GTA  ACA  CGG  AAA  AAC         1062
Ala  Val  Ile  Val  Leu  Pro  Leu  Leu  Tyr  Phe  Leu  Val  Thr  Arg  Lys  Asn
     330                      335                      340

CCT  TGG  GTT  TTT  ATT  GGA  GGG  TTG  CTG  CAA  GCA  CTC  ATC  ACC  GCT  CTG         1110
Pro  Trp  Val  Phe  Ile  Gly  Gly  Leu  Leu  Gln  Ala  Leu  Ile  Thr  Ala  Leu
345                      350                      355                           360

GGG  ACC  TCT  TCA  AGT  TCT  GCC  CTA  CCC  ACC  ATC  TTC  AAG  TGC  CTG              1158
Gly  Thr  Ser  Ser  Ser  Ser  Ala  Leu  Pro  Thr  Ile  Phe  Lys  Cys  Leu
               365                      370                      375

GAA  AAC  AAT  GGC  GTG  GAC  AAG  CGC  CCC  ACC  ATC  ACC  AGA  GTG  CTC  CCC         1206
Glu  Asn  Asn  Gly  Val  Asp  Lys  Arg  Pro  Thr  Ile  Thr  Arg  Val  Leu  Pro
          380                      385                      390

GTA  GGA  GCC  ATT  AAC  ATG  GAT  GGG  ACT  GTC  ATC  ACC  TAT  GAG  TTG             1254
Val  Gly  Ala  Ile  Asn  Met  Asp  Gly  Thr  Val  Ile  Thr  Tyr  Glu  Leu
     395                      400                      405

GCT  GCC  ATT  TTC  ATT  CAA  GCT  TTT  AAC  GTT  AAC  CTG  GAA  AAC  GGA             1302
Ala  Ala  Ile  Phe  Ile  Gln  Ala  Phe  Asn  Val  Asn  Leu  Glu  Asn  Gly
     410                      415                      420

CAA  ATT  ACA  AGC  ATC  ACA  GCC  ACA  GCT  GCT  AGT  ATT  GGG  GCA                   1350
Gln  Ile  Thr  Ser  Ile  Thr  Ala  Thr  Ala  Ala  Ser  Ile  Gly  Ala
425            430                      435                      440
```

FIG. 2E

```
                GCT ATT CCT CAG GCG GGC CTG GTC ACT ATG GTC ATT GTG CTG ACA        1398
                Ala Ile Pro Gln Ala Gly Leu Val Thr Met Val Ile Val Leu Thr
GGA                     445             450             455
Gly

TCT GTC GGC CTG CCC ACT GAC GAC ATC ACG CTC ATC ATC GCG GTG GAC        1446
Ser Val Gly Leu Pro Thr Asp Asp Ile Thr Leu Ile Ile Ala Val Asp
            460             465             470

TGG TTC GAT CGC CTC CGG ACC ACC ACC ACC GTA CTG GGA GAC TCC           1494
Trp Phe Asp Arg Leu Arg Thr Thr Thr Thr Val Leu Gly Asp Ser
Leu                 480             485
Phe
475

CTG GGA GCT GGG ATT GTG GAG CAC TTG TCA CGA CAT CTG AAG AAC           1542
Leu Gly Ala Gly Ile Val Glu His Leu Ser Arg His Leu Lys Asn
    490             495             500

AGA GAT GTT GAA ATG AAC TCA GTG ATT GAA GAG ATT GAA ATG AAG           1590
Arg Asp Val Glu Met Asn Ser Val Ile Glu Glu Ile Glu Met Lys
505             510             515             520

AAA CCA TAT CAA CTG CAA GAC GCA AAT GAA ACT GAG AAA CCC ATC           1638
Lys Pro Tyr Gln Leu Gln Asp Ala Asn Glu Thr Glu Lys Pro Ile
            525             530             535

GAC AGT GAA ACC AAG ATG                                                1680
Asp Ser Glu Thr Lys Met
                540

TAGACTAACA TAAAGAAACA CTTT
```

FIG. 3A

```
GATAGTGCTG AAGAGGAGGG GCGTTCCCAG ACC ATG GCA TCT ACG GAA GGT GCC                  54
                                     Met Ala Ser Thr Glu Gly Ala
                                      1               5

AAC AAT ATG CCC AAG CAG GTG GAA GTG CGA ATG CCA GAC AGT CAT CTT                   102
Asn Asn Met Pro Lys Gln Val Glu Val Arg Met Pro Asp Ser His Leu
         10              15              20

GGC TCA GAG GAA CCC AAG CAC CGG CAC CTG GGC CTG CGC TGT GAC                       150
Gly Ser Glu Glu Pro Lys His Arg His Leu Gly Leu Arg Cys Asp
     25              30              35

AAG CTG GGG AAG AAT CTG CTG CTC ACC CTG ACG GTG TTT GGT GTC ATC                   198
Lys Leu Gly Lys Asn Leu Leu Leu Thr Leu Thr Val Phe Gly Val Ile
 40              45              50              55

CTG GGA GCA GTG TGT CGC TTT GCA TCT CCC ATC ATC CAC                               246
Leu Gly Ala Val Cys Arg Phe Ala Ser Pro Ile Ile His
                     60              65              70

CCT GAT GTG ATG ATG GGG TTA ATA GCC TTC CCA GGG GAT ATA CTC ATG AGG               294
Pro Asp Val Met Met Gly Leu Ile Ala Phe Pro Gly Asp Ile Leu Met Arg
             75              80              85

ATG AAA ATG CTC ATT CTG GGT CTA TCC AGC ATC TTA ATC ACA                           342
Met Lys Met Leu Ile Leu Gly Leu Ser Ser Ile Leu Ile Thr
     90              95             100
```

FIG. 3B

```
GGG  TTG  TCA  GGC  CTG  GAT  AAG  GCT  AGT  GGC  CGC  TTG  GGC  ACG  AGA
Gly  Leu  Ser  Gly  Leu  Asp  Lys  Ala  Ser  Gly  Arg  Leu  Gly  Thr  Arg   390
     105                           110            115

GCC  ATG  GTG  TAT  TAC  ATG  TCC  ACG  ATT  GCA  GTA  CTG  GGG
Ala  Met  Val  Tyr  Tyr  Met  Ser  Thr  Ile  Ala  Val  Leu  Gly           438
120                 125                     130            135

GTC  ATT  CTG  GTC  TTG  GCT  ATC  CAT  CCA  GGC  ATT  AAT  CCC  AAG  CTC  AAG
Val  Ile  Leu  Val  Leu  Ala  Ile  His  Pro  Gly  Ile  Asn  Pro  Lys  Leu  Lys   486
          140                           145                           150

CAG  CTG  GGG  CCT  AAG  GAT  AAT  GAA  GTG  TCC  AGC  CTG  GAT
Gln  Leu  Gly  Pro  Lys  Asp  Asn  Glu  Val  Ser  Ser  Leu  Asp           534
               155            160                      165

TTC  CTG  GAC  CTT  ATT  CGA  AAT  CTC  TTC  CCT  GAA  AAC  CTT  GTC  CAA  GCC
Phe  Leu  Asp  Leu  Ile  Arg  Asn  Leu  Phe  Pro  Glu  Asn  Leu  Val  Gln  Ala   582
          170                      175                      180

TGC  TTT  CAA  CAG  ATT  CAA  ACA  ACG  AAG  AAA  GTT  GCA  CCA
Cys  Phe  Gln  Gln  Ile  Gln  Thr  Thr  Lys  Lys  Val  Ala  Pro           630
     185                      190                      195

CCG  GAC  GAG  GAG  GCC  AAC  GCA  ACC  AGC  GCT  GAA  GTC  TCT  CTG  TTG
Pro  Asp  Glu  Glu  Ala  Asn  Ala  Thr  Ser  Ala  Glu  Val  Ser  Leu  Leu   678
200                      205                      210                 215
```

FIG. 3C

| | | | | | | | | | | | | | | | | |
|---|---|---|---|---|---|---|---|---|---|---|---|---|---|---|---|---|
| AAC Asn | GAG Glu | ACT Thr | GTG Val | ACT Thr 220 | GAG Glu | GTG Val | CCG Pro | GAG Glu 225 | ACT Thr | AAG Lys | ATG Met | GTT Val | ATC Ile 230 | AAG Lys | | 726 |
| AAG Lys | GGC Gly | CTG Leu | GTG Val | GAG Glu 235 | TTC Phe | AAG Lys | GAT Asp | ATG Met 240 | GGG Gly | AAC Asn | GTC Val | TTA Leu | GGT Gly | CTG Leu 245 | GGG Gly | 774 |
| TTT Phe | ATT Ile 250 | GCT Ala | TTT Phe | GGC Gly | ATC Ile 255 | GCT Ala | ATG Met | AAG Lys | GGA Gly 260 | GAT Asp | CAG Gln | GCC Ala | | | | 822 |
| AAG Lys | CTG Leu 265 | ATG Met | GAT Asp | TTC Phe 270 | ATT Ile | TTG Leu | AAT Asn | GAG Glu 275 | ATT Ile | GTA Val | ATG Met | AAG Lys | | | | 870 |
| TTA Leu 280 | GTG Val | ATC Ile | ATG Met 285 | TGG Trp | TAC Tyr | TCT Ser | CCC Pro | CTG Leu 290 | ATC Ile | GCC Ala | TGC Cys | CTG Leu 295 | | | | 918 |
| ATC Ile | TGT Cys | GGA Gly | ATC Ile | ATT Ile | ATC Ile 300 | GCA Ala | AAG Lys | TTA Leu | GAA Glu | GTG Val | GTT Val | GCT Ala 310 | AGG Arg | | | 966 |
| CAA Gln | CTG Leu | GGG Gly | ATG Met 315 | TAC Tyr | GTA Val | ACA Thr | GTG Val 320 | ATC Ile | GGC Gly | CTC Leu | ATC Ile 325 | CAC His | | | | 1014 |

FIG. 3D

| | | | | | | | | | | | | | | | |
|---|---|---|---|---|---|---|---|---|---|---|---|---|---|---|---|
| GGG Gly | ATC Ile 330 | TTT Phe | CTC Leu | CCC Pro | TTG Leu | ATT Ile 335 | TAC Tyr | TTT Phe | GTA Val | GTG Val | ACC Thr 340 | AGG Arg | AAA Lys | AAC Asn | 1062 |
| CCC Pro | TTC Phe 345 | TCC Ser | CTT Leu | TTT Phe | GCT Ala | GGC Gly 350 | ATT Ile | TTC Phe | CAA Gln | GCT Ala | TGG Trp 355 | ATC Ile | ACT Thr | GCC Ala | CTG Leu | 1110 |
| GGC Gly 360 | ACC Thr | TCC Ser | GCT Ala | GCT Ala 365 | GGA Gly | ACT Thr | CCT Pro | GTC Val 370 | ACC Thr | TTT Phe | CGT Arg | TGC Cys | CTG Leu 375 | | | 1158 |
| GAA Glu | AAT Asn | CTG Leu | GGG Gly 380 | ATT Ile | GAT Asp | CGT Arg | GTG Val 385 | CCT Pro | ACT Thr | AGA Arg | TTC Phe | GTC Val | CTT Leu 390 | | | 1206 |
| GTT Val | GGA Gly | ACC Thr 395 | TCC Ser | AAC Asn | AAG Lys | GAT Asp | GGT Gly 400 | CGT Arg | ACA Thr | GCC Ala | TAT Tyr | GAA Glu 405 | GCG Ala | GTG Val | | 1254 |
| GCC Ala | ATC Ile 410 | TTT Phe | ATA Ile | AAC Asn | ATG Met | CAA Gln 415 | ATG Met | AAT Asn | GGT Gly | GTT Val | GTC Val 420 | CTG Leu | GAT Asp | GGA Gly | | 1302 |
| CAG Gln | ATT Ile 425 | GTG Val | ACT Thr | GTA Val | AGC Ser | CTC Leu 430 | CTG Leu | ACA Thr | GCC Ala | GCA Ala 435 | AGC Ser | GTC Val | GGC Gly | GCG Ala | | 1350 |

FIG. 3E

| bp | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1398 | GCC Ala 440 | AGT Ser | ATC Ile | CCC Pro | AGT Ser | GCC Ala 445 | GGG Gly | CTG Leu | GTC Val | ACC Thr | ATG Met 450 | CTC Leu | CTC Leu | ATT Ile | CTG Leu | ACA Thr 455 |
| 1446 | GCC Ala | GTG Val | GGC Gly | CTG Leu | CCA Pro 460 | ACA Thr | GAG Glu | GAC Asp | ATC Ile | AGC Ser 465 | ATG Met | TTG Leu | CTG Leu | GTG Val | GCT Ala | GTG Val 470 |
| 1494 | TGG Trp | CTG Leu | GAC Asp 475 | AGG Arg | ATG Met | AGA Arg | ACT Thr | TCA Ser 480 | ATC Ile | AAT Asn | TTG Leu | CTG Leu | GTG Val | GCT Ala 485 | GGT Gly | GTG Val |
| 1542 | TTT Phe | GGG Gly | GCT Ala 490 | ATA Ile | GTC Val | TAT Tyr | CAC His 495 | CTC Leu | TCT Ser | GTT Val | AAT Asn | TCC Ser 500 | GAG Glu | CTG Leu | GAT Asp | ACC Thr |
| 1590 | ATT Ile | GAC Asp 505 | TCC Ser | GAG Gln | CAT His | CGA Arg | GTG Val 510 | ATG Met | CAT His | GAA Glu | CTC Leu | TCT Ser 515 | GAG Glu | ATG Met | ACC Thr | AAG Lys |
| 1638 | CAA Gln 520 | ATT Ile | GAT Asp | GAC Asp 525 | ATG Met | AAG Lys | AAC Asn | CAC His | AGG Arg 530 | AGC Ser | GAA Glu | AAC Asn | TCT Ser | ATT Asn 535 | |  |
| 1686 | CAA Gln | TGT Cys | GTC Val | TAT Tyr | GCA Ala | CAC His | AAC Asn | TCT Ser | GCT Ala 540 | TAT Tyr | ATA Ile | GTA Val | GAT Asp | GAA Glu | TGC Cys 550 | AAG Lys |

FIG. 3F

```
GTA ACT CTG GCA GCC AAT GGA AAG TCA GCC GAC TGC AGT GTT GAG GAA
Val Thr Leu Ala Ala Asn Gly Lys Ser Ala Asp Cys Ser Val Glu Glu
        555                 560                 565              1734

GAA CCT TGG AAA CGT GAG AAA TAAGGATATG     AGTCTCAGCA     AATTCTTGAA  1785
Glu Pro Trp Lys Arg Glu Lys
        570

TAAACTCCCC AGCGT                                                      1800
```

FIG. 4A

```
ATAGCGGCGA CAGCC                                                                                        51
           ATG  GGG  AAA  CCG  GCG  AGG  AAA  GGA  TGC  CCG  AGT  TGG
           Met  Gly  Lys  Pro  Ala  Arg  Lys  Gly  Cys  Pro  Ser  Trp
            1                    5                        10

AAG  CGC  TTC  CTG  AAG  AAT  AAC  TGG  GTG  CTG  TTG  CTG  TCC  ACC  GTG  GCC  GCG      99
Lys  Arg  Phe  Leu  Lys  Asn  Asn  Trp  Val  Leu  Leu  Leu  Ser  Thr  Val  Ala  Ala
          15                    20                       25

GTG  GTG  CTA  GGC  ATT  ACC  ACA  GGA  GTC  TTG  GTT  CGA  GAA  CAC  AGC  AAC            147
Val  Val  Leu  Gly  Ile  Thr  Thr  Gly  Val  Leu  Val  Arg  Glu  His  Ser  Asn
     30                    35                       40

CTC  TCA  ACT  CTA  GAG  AAA  TTC  TAC  TTT  GCT  TTT  CCT  GGA  GAA  ATT  CTA            195
Leu  Ser  Thr  Leu  Glu  Lys  Phe  Tyr  Phe  Ala  Phe  Pro  Gly  Glu  Ile  Leu
45                         50                       55                       60

ATG  GGG  ATG  CTG  AAA  CTC  ATC  ATT  TTG  CCA  TTA  TCC  ATA  GAA  TCC  AGC  ATG      243
Met  Gly  Met  Leu  Lys  Leu  Ile  Ile  Leu  Pro  Leu  Ser  Ile  Glu  Ser  Ser  Met
                    65                    70                       75

ATT  ACA  GGT  GTT  GCT  GCA  CTG  GAT  TCC  AAC  GTA  TCC  GGA  AAA  TCC  AGC  ATT  GGT  291
Ile  Thr  Gly  Val  Ala  Ala  Leu  Asp  Ser  Asn  Val  Ser  Gly  Lys  Ser  Ser  Ile  Gly
          80                    85                       90

CTG  CGC  GCT  GTC  GTG  TAT  TAT  TTC  TGT  ACC  ACT  CTC  ATT  GCT  GTT  ATT            339
Leu  Arg  Ala  Val  Val  Tyr  Tyr  Phe  Cys  Thr  Thr  Leu  Ile  Ala  Val  Ile
     95                    100                      105
```

FIG. 4B

| | | | | | | | | | | | | | | | | |
|---|---|---|---|---|---|---|---|---|---|---|---|---|---|---|---|---|
| CTA Leu | GGT Gly 110 | ATT Ile | GTG Val | CTG Leu | GTG Val | GTG Val 115 | AGC Ser | ATC Ile | AAG Lys | CCT Pro | GGT Gly 120 | GTC Val | ACC Thr | CAG Gln | AAA Lys | 387 |
| GTG Val 125 | GGT Gly | GAA Glu | ATT Ile | GCG Ala | AGG Arg 130 | ACA Thr | GGC Gly | AGC Ser | ACC Thr | CCT Pro 135 | GAA Glu | GTC Val | AGT Ser | ACG Thr | GTG Val 140 | 435 |
| GAT Asp | GCC Ala | ATG Met | TTA Leu | GAT Asp 145 | CTC Leu | ATC Ile | AGG Arg | AAT Asn | ATG Met 150 | TTC Phe | CCT Pro | GAG Glu | AAT Asn | CTT Leu 155 | GTC Val | 483 |
| CAG Gln | GCC Ala | TGT Cys | TTT Phe 160 | CCA Pro | TAC Tyr | CAG Gln | AAA Lys | ACT Thr 165 | AAG Lys | CGT Arg | GAA Glu | GTG Val 170 | GTG Val | AAG Lys | CCT Pro | 531 |
| CCC Pro | AGC Ser | GAT Asp 175 | CCA Pro | GAG Glu | ATG Met | AAC Asn | ATG Met 180 | ACA Thr | GAG Glu | GAA Glu | TTC Phe 185 | ACA Thr | GCT Ala | GTC Val | 579 |
| ATG Met | ACA Thr 190 | ACT Thr | GCA Ala | ATT Ile | TCC Ser | AAG Lys 195 | AAC Asn | AAA Lys | ACA Thr | AAG Lys | GAA Glu 200 | TAC Tyr | AAA Lys | ATT Ile | GTT Val | 627 |
| GGC Gly 205 | ATG Met | TAT Tyr | TCA Ser | GAT Asp | GGC Gly 210 | ATA Ile | GTC Val | CTG Leu | TTG Leu | GGC Gly 215 | ATT Ile | GTC Val | TTT Phe | TGC Cys 220 | 675 |
| CTT Leu | GTC Val | TTT Phe | GGA Gly | CTT Leu 225 | ATT Ile | GTC Val | AAA Lys | ATG Met 230 | GGA Gly | AAG Lys | GAA Glu | GGA Gly | CAA Gln 235 | ATT Ile | 723 |

FIG. 4C

```
CTG  GTG  GAT  TTC  TTC  AAT  GCT  TTG  AGT  GAT  GCA  ACC  ATG  AAA  ATC  GTT        771
Leu  Val  Asp  Phe  Phe  Asn  Ala  Leu  Ser  Asp  Ala  Thr  Met  Lys  Ile  Val
               240                      245                      250

CAG  ATC  ATG  TGT  TAT  ATG  CCA  CTA  GGT  ATT  TTG  TTC  ATT  GCT                  819
Gln  Ile  Met  Cys  Tyr  Met  Pro  Leu  Gly  Ile  Leu  Phe  Ile  Ala
     255                      260                      265

GGG  AAG  ATA  GAA  GTT  GAA  GAC  TGG  GAA  ATA  TTC  CGC  AAG  CTG  GGC             867
Gly  Lys  Ile  Glu  Val  Glu  Asp  Trp  Glu  Ile  Phe  Arg  Lys  Leu  Gly
     270                 275                      280

CTT  TAC  ATG  ACA  GTC  CTG  ACT  GGG  CTT  GCA  ATC  CAC  TCC  ATT  GTA             915
Leu  Tyr  Met  Thr  Val  Leu  Thr  Gly  Leu  Ala  Ile  His  Ser  Ile  Val
285                 290                      295                      300

ATT  CTC  CCG  CTG  ATA  TTC  TAT  ATA  GTC  GTA  CGA  AAG  AAC  CCT  TTC  CGA        963
Ile  Leu  Pro  Leu  Ile  Phe  Tyr  Ile  Val  Val  Arg  Lys  Asn  Pro  Phe  Arg
               305                      310                      315

TTT  GCC  ATG  GGA  ATG  GCC  CAG  GCT  CTC  CTC  ACA  GCT  CCT  ATG  ATC  TCT       1011
Phe  Ala  Met  Gly  Met  Ala  Gln  Ala  Leu  Leu  Thr  Ala  Pro  Met  Ile  Ser
               320                      325                      330

TCC  AGT  TCA  GCA  ACA  CTG  CCT  GTC  ACC  TTC  CGC  TGT  GCT  GAA  AAT            1059
Ser  Ser  Ser  Ala  Thr  Leu  Pro  Val  Thr  Phe  Arg  Cys  Ala  Glu  Asn
          335                      340                      345
```

FIG. 4D

```
AAC  CAG  GTG  GAC  AAG  AGG  ATC  ACT  CGA  TTC  CTG  TTA  CCC  GTT  GGT  GCA        1107
Asn  Gln  Val  Asp  Lys  Arg  Ile  Thr  Arg  Phe  Val  Leu  Pro  Val  Gly  Ala
     350                      355                      360

ACA  ATC  AAC  ATG  GAT  GGG  ACC  GCG  CTC  TAT  GAA  CCC  GCA  GTG  GCG  GTG        1155
Thr  Ile  Asn  Met  Asp  Gly  Thr  Ala  Leu  Tyr  Glu  Pro  Ala  Val  Ala  Val
365                      370                      375                           380

TTT  ATT  GCA  CAG  TTG  AAT  GAC  CTG  TTG  GGC  ATT  GGG  CAG  ATC  ATC  GCA        1203
Phe  Ile  Ala  Gln  Leu  Asn  Asp  Leu  Leu  Gly  Ile  Gly  Gln  Ile  Ile  Ala
                    385                      390                      395

ACC  ATC  AGT  ATC  ACG  GCC  TCT  GCC  ATC  AGC  GGA  GCT  ATT  GGG  ATC  CAG        1251
Thr  Ile  Ser  Ile  Thr  Ala  Ser  Ala  Ile  Ser  Gly  Ala  Ile  Gly  Ile  Gln
                    400                      405                      410

CCC  CAG  GCT  GGC  CTG  GTT  GTG  ATC  ATG  CTG  AGT  GCT  GCC  TGG  CTC  GTG        1299
Pro  Gln  Ala  Gly  Leu  Val  Val  Ile  Met  Leu  Ser  Ala  Ala  Trp  Leu  Val
                    415                      420                      425

CTG  CCC  GCC  GAT  GTC  ACC  ATT  ATT  CTG  GCT  GAC  TGG  GCC  CTG  GGC  GGC        1347
Leu  Pro  Ala  Asp  Val  Thr  Thr  Ile  Leu  Ala  Asp  Trp  Ala  Leu  Gly  Gly
     430                      435                      440

GAC  AGG  TTC  ACC  ATG  AAC  GTC  CTT  GGT  GAT  GCT  TTT  GGG  ACT  CTG        1395
Asp  Arg  Phe  Thr  Met  Asn  Val  Leu  Gly  Asp  Ala  Phe  Gly  Thr  Leu
445            450                      455                      460
```

FIG. 4E

```
GGC ATT GTG GAA AAG CTC TCC AAG AAG GAG CTG GAG ATG GAT GTT     1443
Gly Ile Val Glu Lys Leu Ser Lys Lys Glu Leu Glu Met Asp Val
            465                 470                 475

TCA TCT GAA GTC AAC ATT GTG AAT CCC TTT GCC TTG GAA TCC ACA ATC 1491
Ser Ser Glu Val Asn Ile Val Asn Pro Phe Ala Leu Glu Ser Thr Ile
        480                 485                 490

CTT GAC AAC GAC TCA GAC AAG AAG GAG CTG TAT GTC AAT GGA GGC     1539
Leu Asp Asn Asp Ser Asp Lys Lys Glu Leu Tyr Val Asn Gly Gly
        495                 500                 505

TTT GCA GTA GAC AAG TCT GAC ATC TCA TTC ACC GAG ACC TCA CAG     1587
Phe Ala Val Asp Lys Ser Asp Ile Ser Phe Thr Glu Thr Ser Gln
    510                 515                 520

TTC TAGGGCCCCT GGCTGCAGAT GACTGGAAAC AAGGAAGGAC ATTTCGTGAG      1640
Phe
525

AGTCATCTCA AACACGGCTT AAGGAAAAGA GAAA                           1674
```

FIG. 5A

```
ASCT1                 MEKSNETNGLYDSAQAGPAAGPGAPGTAAGRARRCARFLRRQALVLL..TVSGVLAGAGLGAAIR.GL
GLAST1  MTKSNGEEPRMGSRMTRFQQGVRKRTLLAKKKVQNITKEDVKSYLFRNAFVLL..TVSAVIVGTILGFAIRPY.
GLT1        MASTEGANNMPKQVEVRMHDSHLSSEEPKHRNLGMRMCDKLGKNLLLSLTVFGVILGAVCGGLIRLAA
EAAC1                                          MGKPARKGCDSKRFLKNNWLLLS.TVVAVVLGIVIGVLVREYS

66 SLSRTQVTYLAFPGEMLRMLRVIILPLVVCSLVSQAASLDASCLQRLGGIRVAYFGL.TTLSASALAVALAFI
 72 KMSYREVKYFSFPGELIMRMLQVLVIPLIISSLVTGMAALDSKASGKMGM.RAVVYMTTTIIAVVIGIIVII
 69 PIHPDVVMLIAFPGDILMRMLKVLILPLIISSLITGLSGLDAKASGRLGT.RAMVYYMSTTIIAVLGVILLA
 43 NLSTLDKFYFAFPGEIIMRMEKLVIIPLIVSSMITGVAALDSNVSGKIGL.RAVLYFCTTIIAVIIGIVBVS

130 IKPGSGAQTLQSSDIGLEDSGPPPVPKETVDSFLDIARNLFPSNLVVAAFRTYATDYKVV......TONSSS
145 IHPGKGT.KENMYREGKIVOVTA.......ADAFIDLIRNMFPPNIVEACFKQFKTSYEKRSFKVPIQANETLLG
142 IHPGNPKLKKQLGPGKKNDEYSS.......LDAFLDLIRNLFPENLVQACFOQIQTVTKKVLVAPPS.EEANTTK
116 IKPGVTQKVDEIDRTGSTPEVST.......VDAMLDLIRNMFPENLVQACFQQYKTTREEV..TASDDTGKNGTE

205 GNVTHEKIPIGTEI............EGMNILGLVLFALVLGVALKKLGSEGEDLIRFFNSLNEATVLVSW
212 AVINVSEAMETLTRIREEMVPVPGSVN.GVNALGLVVFSMCFGFVIGNMKEQGGALREEFDSLNEAIVRLVAV
209 AVISLINETMNEAPEETKIVIKKGLEFKDGMNVLGLIGFFIAFGIAMGKMGVAGGADGGVLOMSERDCHEVSDM
182 ESVTAVMTTAVSENRTKEYRVVGLYS..DGINVLGLIVFCLVFGLVIGKMGEKGGILVDFFNALSDATVKIVQI

265 IMWYVPVGIMFLVGSRIVEMKDIIVLVTSLGKYIFASILGHVIHGGIVLPLIYFVFTRKNPEREFLLGLLAPFAT
285 IMWYAPLGILFLIAGKILEMEDMGVIGGOLAMYTVVGLIHAVIVLPLIYFLVTRKNPWVFIGGLLQALIT
283 DHVFPAGIACLICGKIIAIKDLEVVAROLGMYMITVVGLITHGGIFPLIYFEVVTRKNPESFFAGIFQAWIT
254 IMCYMPLGILFLIAGKLIIEVEDWEIF.RKLGLYMVTVLSGLAHSIVILPLIEIVRKNPRFAMGTQALLT

339 AFATCSSSSATLPSMMKCIEENNGVDKRISREILPLGATVNMDGAAIFQCVAAVFIAGLNNIELNAGQIFGILVT
350 ALGTSSSSATLPIFKCLEENNGVDKRITRFVLPVGATINMDGTALYEALAAIFIAGVNNFDLNFGQIITSIT
357 ALGTASSAGTLPVTFRCLEDNLGIDKRVTREFVLPVGATINMDGTALYEAVAAIFIAGMNGVILDGGOIVTVSLT
327 ALMISSSSATLPVTFRCAEEKNRVDKRITRFVLPVGATINMDGTALYEAVAAVFIAGLNDMDISIGQIITISVT
```

FIG. 5B

```
413  ATASSVGAAGVPAGGVLTIAIIEAIGLPTHDLPLILAVDWIVDRTTTVVNVEGDALGAGILHMLNQKATKKGE
433  ATAASIGAAGIPOAGLVIMVIVLTSYGLPTDDITIIIAVDWFIDRLRTTNVLGDSLGAGIVEHLSRHELKNRD
431  ATLASIGAASIPSAGLVTMLLIITAVGLPTEDISLLVAVDWLLDRMRTSVNVVGDSFGAGIVYHISKSELDTID
401  ATAASIGAAGVPOAGLVTMVIVLSAVGLPAEDVTLIIAVDWLLIDRFRTVNVLGDAFGTGIVEKLSKKELEQMD

487  QELAEVKVEAIPNCKSEEETSPLVTHQNPAGPVASAPELESKESVL              532
507  VEMGNSVIEENEMKKPYQLIAQDNEPEKPVADSETKM                       543
505  SQHRMHEDIEMTKTQSVYDDTKNHRESNSNQCVYAAHNSVVIDECKVTLAANGKSADCSVEEEPWKREK    573
475  VSSEVNIVNPFALESATLDNEDSDTKKSYINGGFAVDKSDTISFTQTSQF          524
```

FIG. 11

```
EAAT1        MTKSNGEEPKMGGRMERFQQGVRKRTLLAKKKVQNTKKQVKSYLFGNPFVTL..TVTAVIVGI.LGFIIRPY.
EAAT2        MASTEGANNMPKQVEVRMPDSHLGSEEPKHRMLGLRLCDKLGKNLLITLTVFGVILGAVCGGIIRLAS
EAAT3                        MGKFARKGCPSWKRFLKNNWVLLS.TVAAVVLGITTGVIVREHS
                                                                            |——1——|

72      RMSYREVKYFSFPGELLMRMIQMEVIPLIISSLVTGMAALDSKASGKMGRAVVYYMTTTIAVVIGIIIVII
     69      PIMPDVVMLIAFPGDILMRLKMLILPLIISSLITGLSLDAKASGRLGTRAMVYYMSTTIAAVIGVILVLAI
     44      NLSTLEKFYFAFPGEIIMRMLKLIILPLIISSMITGVAALDSNVSGKIGLRAVVYYFGTTLIAVIGIVVSI
                 |——2——|                                         |——3——|

146      HPGKGT KENMHREGKIVRVTAADAFLDIRNMFPPNLVEACFKQFKTGYEKRSFKVPIQANETLVGAVINNVS
    143      HPGNPKLKKQLGPGKKNDEVSSLDAFLDIRNLFPENLVQACFQQIQTVTKKVLVAPPPDEENATSAEVSLLN
    118      KPGVTQKVGEIARTGSTPEVSTVDAMLDLIRNMFPENLVQACEQQVKTKREV..KPPSDPEMNMTEESFTAVM

219      EAMETLTRITEELVPVPGSVN.GVNALGIVVESMCEFGFVIGNMKEQGQALREFFDSLNEAIMRLVAVIMWYAPE
    217      ETVTEVPEETKMVIKKGLEFKDGMNVIGLIIGFIAFGIAMGKMGDQAKLMVDFFNILNEIVMKLVIMIMWYSPL
    190      TTAISKNKTKFEYKIVGMYS..DGINVLGLIIVECLVEGLNIGLVIGKMGEKGQILVDFFNALSDATMKIVQIIMCVMPL
                         |——4——|                                                |——5——|

292      GILFLIAGKIVEMEDMGVIGGQLAMYTYTVIVGLLIHAVIVIPLLYELVTRKNPWVFIGGLLQALITALGTSSS
    291      GIACLICGKTTAIKDLEVVAROIGMYMVTVIIGLIIHGGIFIPLIYFVVTRKNPFSLFAGIFQAWITALGTASS
    261      GILFLIAGKIIEVEDWFIF.RKLGLYMATVLTGIAIHSIVILPLIYFIVRKNPFRFAMGMAQALLTAIMISSS
                              |——6——|

366      SATLPITFKCLEENNGVDKRVTRFVLPVGATINMDGTALYEALAAIFIAQVNNFELNFGQITISITATAASIG
    385      AGTLPITFKCLEENLGIDKRVTRFVLPVGATINMDGTALYEAVAAIFIAQMNGVVLDGGQIVTVSLTATLASVG
    334      SATLPITFKCAEENNQVDKRITRFVLPVGATINMDGTAIYEAVAAVFIAQLNDLDLGIQITTSITATSASIG
                              |——7——|                        |——8——|
```

FIG. 11A

```
440  AAGIPQAGLVTMVIVLTSVGLPTDDITIIAVDWFLDRLRTTTNVLGDSLGAGIVEHLSRHELKNRDVEMGNSV
439  AASIPSAGLVTMLLITAVGLPTEDISLLVAVGLPTEDISLLVAVDWLLDRMRTSVNVVGDSFGAGIVYHLSKSELDTIDSQMRVHE
408  AAGVPQAGLVTMVIVLSAVGLIPAEDVTLIIAVDWLLDRFRTMVNVLGDAFGTGIVEKISKKELEQMDVSSEVNI

514  IEENEMKKPYQLIAQDNTEKPIDSETKM 542
513  DIEMTKTQSIYDDMKNHRESNSNQCVYAAHNSVIVDECKVTLAANGKSADCSVEEEPWKREK 574
482  VNPFALESTILDNEDSDTKKSYVNGGFAVDKSDTISFTQTSQF 525
```

AMINO ACID TRANSPORTERS AND USES

BACKGROUND OF THE INVENTION

1. Field of the Invention

This invention relates to amino acid transporters from mammalian species and the genes corresponding to such transporters. Specifically, the invention relates to the isolation, cloning and sequencing of complementary DNA (cDNA) copies of messenger RNA (mRNA) encoding each of four novel human amino acid transporter genes. The invention also relates to the construction of recombinant expression constructs comprising such cDNAs from each of the four novel human amino acid transporter genes of the invention, said recombinant expression constructs being capable of expressing amino acid transporter proteins in cultures of transformed prokaryotic and eukaryotic cells. Production of the transporter proteins in such cultures is also provided. The invention relates to the use of such cultures of such transformed cells to produce homogeneous compositions of each transporter protein. The invention also provides cultures of such cells producing transporter proteins for the characterization of novel and useful drugs. Antibodies against and epitopes of these transporter proteins are also provided by the invention.

2. Background of the Invention

The approximately 20 naturally-occurring amino acids are the basic building blocks for protein biosynthesis. Certain amino acids, such as glutamate and glycine, as well as amino acid derivatives such as γ-aminobutyric acid (GABA), epinephrine and norepinephrine, and histamine, are also used as signaling molecules in higher organisms such as man. For these reasons, specialized trans-membrane transporter proteins have evolved in all organisms to recover or scavenge extracellular amino acids (see Christensen, 1990, Physiol. Rev. 70: 43–77 for review).

These transporter proteins play a particularly important role in uptake of extracellular amino acids in the vertebrate brain (see Nicholls & Attwell, 1990, TiPS 11: 462–468). Amino acids that function as neurotransmitters must be scavenged from the synaptic cleft between neurons to enable continuous repetitive synaptic transmission. More importantly, it has been found that high extracellular concentrations of certain amino acids (including glutamate and cysteine) can cause neuronal cell death. High extracellular amino acid concentrations are associated with a number of pathological conditions, including ischemia, anoxia and hypoglycemia, as well as chronic illnesses such as Huntington's disease, Parkinson's disease, Alzheimer's disease, epilepsy and amyotrophic lateral sclerosis (ALS; see Pines et al., 1992, Nature 360: 464–467).

Glutamate is one example of such an amino acid. Glummate is an excitatory neurotransmitter (i.e., excitatory neurons use glutamate as a neurotransmitter). When present in excess (>about 300 μM; Bouvier et al., 1992, Nature 360: 471–474; Nicholls & Attwell, ibid.; >5 μM for 5 min.; Choi et al., 1987, J. Neurosci. 7: 357–358), extracellular glutamate causes neuronal cell death. Glummate transporters play a pivotal role in maintaining non-toxic extracellular concentrations of glutamate in the brain. During anoxic conditions (such as occur during ischemia), the amount of extracellular glutamate in the brain rises dramatically. This is in part due to the fact that, under anoxic conditions, glutamate transporters work in reverse, thereby increasing rather than decreasing the amount of extracellular glutamate found in the brain. The resultingly high extracellular concentration of glutamate causes neuron death, with extremely deleterious consequences for motor and other brain functions, resulting in stroke, anoxia and other instances of organic brain dysfunction.

This important role for amino acid transporters in maintaining brain homeostasis of extracellular amino acid concentrations has provided the impetus for the search for and development of compounds to modulate and control transporter function. However, conventional screening methods require the use of animal brain slices in binding assays as a first step. This is suboptima/for a number of reasons, including interference in the binding assay by non-specific binding of heterologous (i.e., non-transporter) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. The ability to synthesize human transporter molecules in vitro would provide an efficient and economical means for rational drug design and rapid screening of potentially useful compounds.

Amino acid transporters are known in the art, and some of these proteins have been isolated biochemically and their corresponding genes have been recently cloned using genetic engineering means.

Christensen et al., 1967, J. Biol. Chem. 242:5237–5246 report the discovery of a neutral amino acid transporter (termed the ACS transporter) in Erlich ascites tumor cells.

Makowske & Christensen, 1982, J. Biol. Chem. 257:14635–14638 provide a biochemical characterization of hepatic amino acid transport.

Kanner & Schuldiner, 1987, CRC Crit. Rev. Biochem. 22:1–38 provide a review of the biochemistry of neurotransmitters.

Olney et al., 1990, Science 248:596–599 disclose that the amino acid cysteine is a neurotoxin when present in excess extracellularly.

Wallace et al., 1990, J. Bacteriol. 172:3214–3220 report the cloning and sequencing of a glutamate/aspartate transporter gene termed gltP from Escherichia coli strain K12.

Kim et al., 1991, Nature 352:725–728 report the discovery that a cationic amino acid transporter is the cell surface target for infection by ecotropic retroviruses in mice.

Wang et al., 1991, Nature 352:729–731 report the discovery that a cationic amino acid transporter is the cell surface target for infection by ecotropic retroviruses in mice.

Maenz et al., 1992, J. Biol. Chem. 267:1510–1516 provide a biochemical characterization of amino acid transport in rabbit jejunal brush border membranes.

Bussolati et al., 1992, J. Biol. Chem. 267:8330–8335 report that the ASC transporter acts in an electrochemically neutral manner so that sodium ion co-transport occurs without disrupting the normal membrane potential of the cells expressing the transporter.

Engelke et al., 1992, J. Bacteriol. 171:5551–5560 report the cloning of a dicarboxylate carrier from Rhizobium meliloti.

Guastella et al., 1992, Proc. Natl. Acad. Sci. USA 89:7189–7193 disclose the cloning of a sodium ion and chloride ion-dependent glycine transporter from a glioma cell line that is expressed in the rat forebrain and cerebellum.

Kavanaugh et al., 1992, J. Biol. Chem. 267:22007–22009 report that biochemical characterization of a rat brain GABA transporter expressed in vitro in Xenopus laevis oocytes.

Storck et al., 1992, Proc. Natl. Acad. Sci. USA 89:10955–10959 disclose the cloning and sequencing of a sodium ion-dependent glutamate/aspartate transporter from rat brain termed GLAST1.

Bouvier et al., ibid., disclose the biochemical characterization of a glial cell-derived glutamate transporter.

Pines et al., ibid., report the cloning and sequencing of a glial cell glutamate transporter from rat brain termed GLT-1.

Kanai & Hediger, 1992, Nature 360:467–471 disclose the cloning and sequencing of a sodium ion-dependent, high affinity glutamate transporter from rabbit small intestine termed EAAC1.

Kong et at., 1993, J. Biol. Chem. 268:1509–1512 report the cloning and sequencing of a sodium-ion dependent neutral amino acid transporter of the A type that is homologous to a sodium-ion dependent glucose transporter.

Nicholls & Attwell, ibid., review the role of amino acids and amino acid transporters in normal and pathological brain functions.

SUMMARY OF THE INVENTION

The present invention relates to the cloning, expression and functional characterization of mammalian amino acid transporter genes. The invention comprises nucleic acids, each nucleic acid having a nucleotide sequence of a novel amino acid transporter gene. The nucleic acids provided by the invention each comprise a complementary DNA (cDNA) copy of the corresponding mRNA transcribed in vivo from each of the amino acid transporter genes of the invention. Also provided are the deduced amino acid sequences of each the cognate proteins of the cDNAs provided by the invention.

This invention provides nucleic acids, nucleic acid hybridization probes, recombinant eukaryotic expression constructs capable of expressing the amino acid transporters of the invention in cultures of transformed cells, such cultures of transformed eukaryotic cells that synthesize the amino acid transporters of the invention, homogeneous compositions of each of the amino acid transporter proteins, and antibodies against and epitopes of each of the amino acid transporter proteins of the invention. Methods for characterizing these transporter proteins and methods for using these proteins in the development of agents having pharmacological uses related to these transporter proteins are also provided by the invention.

In a first aspect, the invention provides a nucleic acid having a nucleotide sequence encoding a human neutral amino acid transporter that is the ASCT1 transporter (SEQ ID No:2). In this embodiment of the invention, the nucleotide sequence includes 1680 nucleotides of the human ASCT1 cDNA comprising 1596 nucleotides of coding sequence, 30 nucleotides of 5' untranslated sequence and 54 nucleotides of 3' untranslated sequence. In this embodiment of the invention, the nucleotide sequence of the ASCT1 transporter consists essentially of the nucleotide sequence depicted in FIG. 1 (SEQ ID No:2). The use of the term "consisting essentially of" herein is meant to encompass the disclosed sequence and includes allelic variations of this nucleotide sequence, either naturally occurring or the product of in vitro chemical or genetic modification. Each such variant will be understood to have essentially the same nucleotide sequence as the nucleotide sequence of the corresponding ASCT1 disclosed herein.

The corresponding ASCT1 protein molecule, having the deduced amino acid sequence consisting essentially of the sequence shown in FIG. 1 (SEQ ID No.:3), is also claimed as an aspect of the invention. The use of the term "consisting essentially of" herein is as described above. Similarly, the corresponding ASCT1 protein molecule, having the deduced amino acid sequence consisting essentially of the sequence shown in FIG. 1 (SEQ ID No.:3), is also claimed as an aspect of the invention. ASCT1 protein molecules provided by the invention are understood to have substantially the same biological properties as the ASCT1 protein molecule encoded by the nucleotide sequence described herein.

In another aspect, the invention comprises a homogeneous composition of the 55.9 kD mammalian ASCT1 transporter or derivative thereof, said size being understood to be the size of the protein before any post-translational modifications thereof. The amino acid sequence of the ASCT1 transporter or derivative thereof preferably consists essentially of the amino acid sequence of the human ASCT1 transporter protein shown in FIG. 1 (SEQ ID No:3).

In a second aspect, the invention provides a nucleic acid having a nucleotide sequence encoding a human excitatory amino acid transporter that is the EAAT1 transporter (SEQ ID No:4). In this embodiment of the invention, the nucleotide sequence includes 1680 nucleotides of the human EAAT1 cDNA comprising 1626 nucleotides of coding sequence, 30 nucleotides of 5' untranslated sequence and 24 nucleotides of 3' untranslated sequence. In this embodiment of the invention, the nucleotide sequence of the EAAT1 transporter consists essentially of the nucleotide sequence depicted in FIG. 2 (SEQ ID No:4). The use of the term "consisting essentially of" herein is as described above.

In another aspect, the invention comprises a homogeneous composition of the 59.5 kilodalton (kD) mammalian EAAT1 transporter or derivative thereof, said size being understood to be the size of the protein before any post-translational modifications thereof. The amino acid sequence of the EAAT1 transporter or derivative thereof preferably consists essentially of the amino acid sequence of the human EAAT1 transporter protein shown in FIG. 2 (SEQ ID No:5). EAAT1 protein molecules provided by the invention are understood to have substantially the same biological properties as the EAAT1 protein molecule encoded by the nucleotide sequence described herein.

In a third aspect, the invention provides a nucleic acid having a nucleotide sequence encoding a human excitatory amino acid transporter that is the EAAT2 transporter (SEQ ID No:6). In this embodiment of the invention, the nucleotide sequence includes 1800 nucleotides of the human EAAT2 cDNA comprising 1722 nucleotides of coding sequence, 33 nucleotides of 5' untranslated sequence and 45 nucleotides of 3' untranslated sequence. In this embodiment of the invention, the nucleotide sequence of the EAAT2 transporter consists essentially of the nucleotide sequence depicted in FIG. 3 (SEQ ID No:6). The use of the term "consisting essentially of" herein is as described above.

The corresponding EAAT2 protein molecule, having the deduced amino acid sequence consisting essentially of the sequence shown in FIG. 3 (SEQ ID No.:7), is also claimed as an aspect of the invention. EAAT2 protein molecules provided by the invention are understood to have substantially the same biological properties as the EAAT2 protein molecule encoded by the nucleotide sequence described herein.

In another aspect, the invention comprises a homogeneous composition of the 62.1 kD mammalian EAAT2 transporter or derivative thereof, said size being understood to be the size of the protein before any post-translational modifications thereof. The amino acid sequence of the EAAT2 transporter or derivative thereof preferably consists essentially of the amino acid sequence of the human EAAT2 transporter protein shown in FIG. 3 (SEQ ID No:7).

In yet another aspect, the invention provides a nucleic acid having a nucleotide sequence encoding a human excitatory amino acid transporter that is the EAAT3 transporter (SEQ ID No:8). In this embodiment of the invention, the nucleotide sequence includes 1674 nucleotides of the human EAAT3 cDNA comprising 1575 nucleotides of coding sequence, 15 nucleotides of 5' untranslated sequence and 84 nucleotides of 3' untranslated sequence. In this embodiment of the invention, the nucleotide sequence of the EAAT3 transporter consists essentially of the nucleotide sequence depicted in FIG. 4 (SEQ ID No:8). The use of the term "consisting essentially of" herein is as described above.

The corresponding EAAT3 protein molecule, having the deduced amino acid sequence consisting essentially of the sequence shown in FIG. 4 (SEQ ID No.:9), is also claimed as an aspect of the invention. EAAT3 protein molecules provided by the invention are understood to have substantially the same biological properties as the EAAT3 protein molecule encoded by the nucleotide sequence described herein.

In another aspect, the invention comprises a homogeneous composition of the 57.2 kD) mammalian EAAT3 transporter or derivative thereof, said size being understood to be the size of the protein before any post-translational modifications thereof. The amino acid sequence of the EAAT3 transporter or derivative thereof preferably consists essentially of the amino acid sequence of the human EAAT3 transporter protein shown in FIG. 4 (SEQ ID No:9).

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clone embodying the invention, and oligonucleotide and other synthetic probes synthesized chemically using the nucleotide sequence information of cDNA or genomic done embodiments of the invention.

It is a further object of this invention to provide such nucleic acid hybridization probes to determine the pattern, amount and extent of expression of these transporter genes in various tissues of mammals, including humans. It is also an object of the present invention to provide nucleic acid hybridization probes derived from the sequences of the amino acid transporter genes of the invention to be used for the detection and diagnosis of genetic diseases. It is an object of this invention to provide nucleic acid hybridization probes derived from the DNA sequences of the amino acid transporter genes herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be used as antigens for the production of amino acid transporter-specific antibodies, or used for competitors of amino acid transporter molecules for amino acid, agonist, antagonist or drug binding, or to be used for the production of inhibitors of the binding of agonists or antagonists or analogues thereof to such amino acid transporter molecules.

The present invention also provides antibodies against and epitopes of the mammalian amino acid transporter molecules of the invention. It is an object of the present invention to provide antibodies that are immunologically reactive to the amino acid transporters of the invention. It is a particular object to provide monoclonal antibodies against these amino acid transporters, must preferably the human excitatory and neutral amino acid transporters as herein disclosed. Hybridoma cell lines producing such antibodies are also objects of the invention. It is envisioned at such hybridoma cell lines may be produced as the result of fusion between a non-immunoglobulin producing mouse myeloma cell line and spleen cells derived from a mouse immunized with a cell line which expresses antigens or epitopes of an amino acid transporter of the invention. The present invention also provides hybridoma cell lines that produces such antibodies, and can be injected into a living mouse to provide an ascites fluid from the mouse that is comprised of such antibodies. It is a further object of the invention to provide immunologically-active epitopes of the amino acid transporters of the invention. Chimeric antibodies immunologically reactive against the amino acid transporter proteins of the invention are also within the scope of this invention.

The present invention provides recombinant expression constructs comprising a nucleic acid encoding an amino acid transporter of the invention wherein the construct is capable of expressing the encoded amino acid transporter in cultures of cells transformed with the construct. Preferred embodiments of such constructs comprise the human EAAT1 cDNA (SEQ ID No.:4), the human EAAT2 cDNA (SEQ ID No.:6), the human EAAT3 cDNA (SEQ ID No.:8), and human ASCT1 cDNA (SEQ ID No.:2), each construct being capable of expressing the amino acid transporter encoded therein in cells transformed with the construct.

The invention also provides cultures cells transformed with the recombinant expression constructs of the invention, each such cultures being capable of and in fact expressing the amino acid transporter encoded in the transforming construct.

The present invention also includes within its scope protein preparations of prokaryotic and eukaryotic cell membranes containing at least one of the amino acid transporter proteins of the invention, derived from cultures of prokaryotic or eukaryotic cells, respectively, transformed with the recombinant expression constructs of the invention. In a preferred embodiment, each preparation of such cell membranes comprises one species of the amino acid transporter proteins of the invention.

The invention also provides methods for screening compounds for their ability to inhibit, facilitate or modulate the biochemical activity of the amino acid transporter molecules of the invention, for use in the in vitro screening of novel agonist and antagonist compounds. In preferred embodiments, cells transformed with a recombinant expression construct of the invention are contacted with such a compound, and the effect of the compound on the transport of the appropriate amino acid is assayed. Additional preferred embodiments comprise quantitative analyses of such effects.

The present invention is also useful for the detection of analogues, agonists or antagonists, known or unknown, of the amino acid transporters of the invention, either naturally occurring or embodied as a drug. In preferred embodiments, such analogues, agonists or antagonists may be detected in blood, saliva, semen, cerebrospinal fluid, plasma, lymph, or any other bodily fluid.

Specific preferred embodiments of the present invention will become evident from the following more detailed description of certain preferred embodiments and the claims.

DESCRIPTION OF THE DRAWINGS

FIG. 1 illustrates the nucleotide (SEQ ID No.:2) and amino acid (SEQ ID No.:3) sequences of the human ASCT1 neutral amino acid transporter.

FIG. 2 illustrates the nucleotide (SEQ ID No.:4) and amino acid (SEQ ID No.:5) sequences of the human EAAT1 excitatory amino acid transporter.

FIG. 3 illustrates the nucleotide (SEQ ID No.:6) and amino acid (SEQ ID No.:7) sequences of the human EAAT2 excitatory amino acid transporter.

FIG. 4 illustrates the nucleotide (SEQ ID No.:8) and amino acid (SEQ ID No.:9) sequences of the human EAAT3 excitatory amino acid transporter.

FIG. 5 presents an amino acid sequence comparison between human ASCT1, GLAST1, GLT1 and EAAC1.

FIG. 11 illustrates the degree of predicted amino acid sequence homology between the novel human glutamate transporters EAAT1, EAAT2 and EAAT3; overbars indicate nine regions of hydrophobicity determined using the algorithm of Eisenberg et al., and potential sites of N-linked glycosylation are shown by the circled asparagine (N) residues.

Figure 6A:
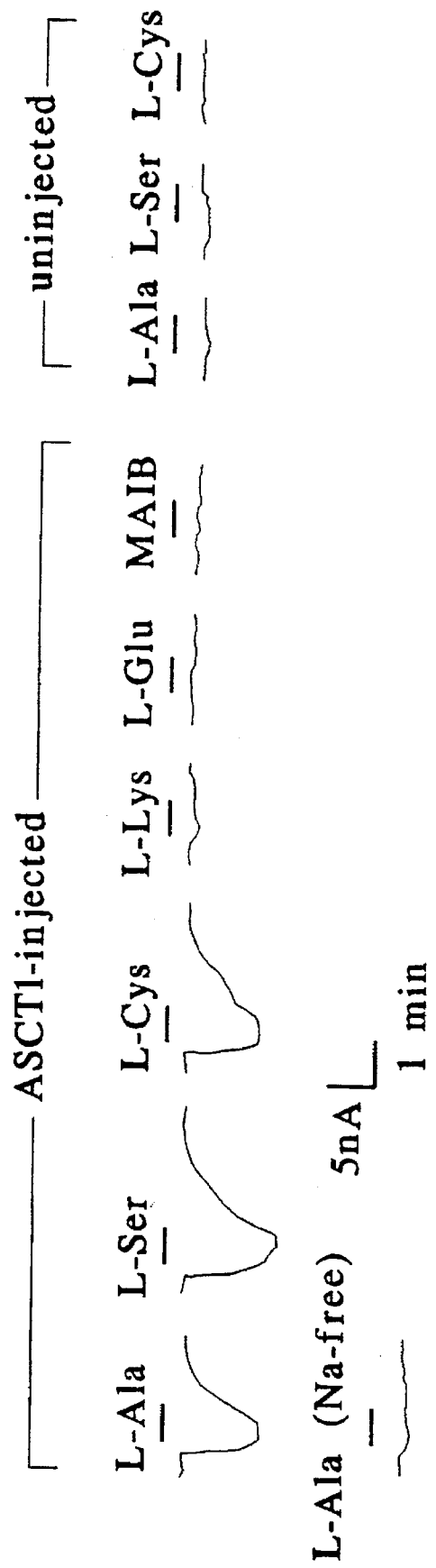
FIG. 6 illustrates transmembrane electrochemical currents in *Xenopus laevis* oocytes microinjected with RNA encoding ASCT1 and contacted with the indicated amino acids (Panel A); the amino acid concentration dependence of such electrochemical currents (Panel B); and a plot of normalized current vs. amino acid concentration illustrating the kinetic parameters of amino acid transport (Panel C).

Table III illustrates Glutamate uptake inhibition constants.

DETAILED DESCRIPTION OF THE PREFERRED EMBODIMENTS

The term "human amino acid transporter EAAT1" as used herein refers to proteins consisting essentially of, and having substantially the same biological activity as, the protein encoded by the nucleic acid depicted in FIG. 2 (SEQ ID No.:4). This definition is intended to encompass natural allelic variations in the EAAT1 sequence. Cloned nucleic acid provided by the present invention may encode EAAT1 protein of any species of origin, including, for example, mouse, rat, rabbit, cat, and human, but preferably the nucleic acid provided by the invention encodes EAAT1 receptors of mammalian, most preferably human, origin.

The tea "human amino acid transporter EAAT2" as used herein refers to proteins consisting essentially of, and having substantially the same biological activity as, the protein encoded by the nucleic acid depicted in FIG. 3 (SEQ ID No.:6). This definition is intended to encompass natural allelic variations in the EAAT2 sequence. Cloned nucleic acid provided by the present invention may encode EAAT2 protein of any species of origin, including, for example, mouse, rat, rabbit, cat, and human, but preferably the nucleic acid provided by the invention encodes EAAT2 receptors of mammalian, most preferably human, origin.

The term "human amino acid transporter EAAT3" as used herein refers to proteins consisting essentially of, and having substantially the same biological activity as, the protein encoded by the nucleic acid depicted in FIG. 4 (SEQ ID No.:8). This definition is intended to encompass natural allelic variations in the EAAT3 sequence. Cloned nucleic acid provided by the present invention may encode EAAT3 protein of any species of origin, including, for example, mouse, rat, rabbit, cat, and human, but preferably the nucleic acid provided by the invention encodes EAAT3 receptors of mammalian, most preferably human, origin.

The term "human amino acid transporter ASCT1" as used herein refers to proteins consisting essentially of, and having substantially the same biological activity as, the protein encoded by the nucleic acid depicted in FIG. 1 (SEQ ID No.:2). This definition is intended to encompass natural allelic variations in the ASCT1 sequence. Cloned nucleic acid provided by the present invention may encode ASCT1 protein of any species of origin, including, for example, mouse, rat, rabbit, cat, and human, but preferably the nucleic acid provided by the invention encodes ASCT1 receptors of mammalian, most preferably human, origin.

Each of the nucleic acid hybridization probes provided by the invention comprise DNA or RNA consisting essentially of the nucleotide sequence of one of the amino acid transporters, depicted in FIGS. 1–4 (SEQ ID Nos.:2,4,6,8), or any portion thereof effective in nucleic acid hybridization. Mixtures of such nucleic acid hybridization probes are also within the scope of this embodiment of the invention. Nucleic acid probes as provided herein are useful for detecting amino acid transporter gene expression in cells and tissues using techniques well-known in the art, including but not limited to Northern blot hybridization, in situ hybridization and Southern hybridization to reverse transcriptase—polymerase chain reaction product DNAs. The probes provided by the present invention, including oligonucleotides probes derived therefrom, are useful are also useful for Southern hybridization of mammalian, preferably human, genomic DNA for screening for restriction fragment length polymorphism (RFLP) associated with certain genetic disorders.

The production of proteins such as these amino acid transporter molecules from cloned genes by genetic engineering means is well known in this art. The discussion which follows is accordingly intended as an overview of this field, and is not intended to reflect the full state of the art.

DNA encoding an amino acid transporter may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carded out with oligonucleotide probes generated from the nucleic acid sequence information from each of the amino acid transporters disclosed herein. Probes may be labeled with a detectable group such as a fluorescent group, a radioactive atom or a chemiluminescent group in accordance with know procedures and used in conventional hybridization assays, as described in greater detail in the Examples below. In the alternative, amino acid transporter-derived nucleic acid sequences may be obtained by use of the polymerase chain reaction (PCR) procedure, using PCR oligonucleotide primers corresponding to nucleic acid sequence information derived from an amino acid transporter as provided herein. See U.S. Pat. Nos. 4,683,195 to Mullis et al. and 4,683,202 to Mullis.

Each of the amino acid Wansporter proteins may be synthesized in host cells transformed with a recombinant expression construct comprising a nucleic acid encoding the particular amino acid transporter cDNA. Such recombinant expression constructs can also be comprised of a vector that is a replicable DNA construct. Vectors are used herein either to amplify DNA encoding an amino acid transporter and/or to express DNA encoding an amino acid transporter gene. For the purposes of this invention, a recombinant expression construct is a replicable DNA construct in which a nucleic acid encoding an amino acid transporter is operably linked to suitable control sequences capable of effecting the expression of the amino acid transporter in a suitable host.

The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is pCMV5 (Andersson et al., 1989, J. Biol. Chem. 264: 8222–8229). Transformed host cells are cells which have been transformed or transfected with recombinant expression constructs made using recombinant DNA techniques and comprising nucleic acid encoding an amino acid transporter protein. Preferred host cells are COS-7 cells (Gluzman, 1981, Cell 23: 175–182). Transformed host cells may express the amino acid transporter protein, but host cells transformed for purposes of cloning or amplifying nucleic acid hybridization probe DNA need not express the transporter. When expressed, each of the amino acid transporters of the invention will typically be located in the host cell membrane. See, Sambrook et al., ibid.

Cultures of cells derived from multicellular organisms are a desirable host for recombinant antino acid transporter protein synthesis. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, and WI138, BI-IK, COS-7, CV, and MDCK cell lines. COS-7 cells are preferred.

The invention provides homogeneous compositions of each of the human EAAT1, EAAT2, EAAT3 and ASCT1 amino acid transporter proteins produced by transformed eukaryotic cells as provided herein. Each such homogeneous composition is intended to be comprised of the corresponding amino acid transporter protein that comprises at least 90% of the protein in such a homogenous composition. The invention also provides membrane preparation from cells expressing each of the amino acid transporter proteins as the result of transformation with a recombinant expression construct, as described herein.

Amino acid transporter proteins made from cloned genes in accordance with the present invention may be used for screening amino acid analogues, or agonist or antagonists of amino acid transport, or for determining the amount of such agonists or antagonists in a solution of interest (e.g., blood plasma or serum). For example, host cells may be transformed with a recombinant expression construct of the present invention, an amino acid transporter expressed in those host cells, and the cells or membranes thereof used to screen compounds for their effect on amino acid transport activity. By selection of host cells that do not ordinarily express a particular amino acid transporter, pure preparations of membranes containing the transporter can be obtained.

The recombinant expression constructs of the present invention are useful in molecular biology to transform cells which do not ordinarily express a particular amino acid transporter to thereafter express this receptor. Such cells are useful as intermediates for making cell membrane preparations useful for transporter activity assays, which are in turn useful for drug screening. The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, Cell 51:503–512; Bertling, 1987, Bioscience Reports 7: 107–112; Smithies et al., 1985, Nature 317:230–234.

Oligonucleotides of the present invention are useful as diagnostic tools for probing amino acid transporter gene expression in tissues of humans and other animals. For example, tissues are probed in situ with oligonucleotide probes carrying detectable groups by conventional autoradiographic techniques, to investigate native expression of this receptor or pathological conditions relating thereto. Further, chromosomes can be probed to investigate the presence or absence of the corresponding amino acid transporter gene, and potential pathological conditions related thereto.

The invention also provides antibodies that are immunologically reactive to the amino acid transporter proteins or epitopes thereof provided by the invention. The antibodies provided by the invention may be raised, using methods well known in the art, in animals by inoculation with cells that express an amino acid transporter or epitopes thereof, cell membranes from such cells, whether crude membrane preparations or membranes purified using methods well known in the art, or purified preparations of proteins, including fusion proteins, particularly fusion proteins comprising epitopes of the amino acid transporter proteins of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses one of the amino acid transporters provided by the invention, or any cell or cell line that expresses one of the amino acid transporters of the invention, or any epitope thereof, as a result of molecular or genetic engineering, or that has been treated to increase the expression of an endogenous or heterologous amino acid transporter protein by physical, biochemical or genetic means. Preferred cells are E. coli and insect SF9 cells, most preferably E. coli cells, that have been transformed with a recombinant expression construct of the invention encoding an amino acid transporter protein, and that express the transporter therefrom.

The present invention also provides monoclonal antibodies that are immunologically reactive with an epitope derived from an amino acid transporter of the invention, or fragment thereof, present on the surface of such cells, preferably E. coli cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cells of a myeloma cell line with spleen cells derived from animals immunized with cells expressing an amino acid transporter of the invention, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an amino acid transporter of the invention. The present invention also encompasses fragments, including but not limited to F(ab) and F(ab)'$_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of an amino acid transporter, made by methods known to those of skill in the art.

The present invention also encompasses an epitope of an amino acid transporter of the invention, comprised of sequences and/or a conformation of sequences present in the transporter molecule. This epitope may be naturally occurring, or may be the result of proteolytic cleavage of a transporter molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an amino acid transporter-derived epitope. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They set forth for explanatory purposes only, and are not to be taken as limiting the invention.

EXAMPLE 1

Isolation Of a Human Neutral Amino Acid Transporter cDNA

In order to clone a novel human neutral amino acid transporter, a cDNA library was prepared from human motor cortex mRNA using standard techniques [see Sambrook et al., 1990, *Molecular Cloning: A Laboratory Manual* (Cold Spring Harbor Press: New York)]. Briefly, total RNA was isolated using the method of Chomczynski & Sacchi (1987, Anal. Biochem. 162: 156–159), wherein the tissue is disrupted and solubilized in a solution containing guanidinium isothiocyanate and the RNA purified by phenol/chloroform extractions. Total cellular RNA thus isolated was then enriched for poly (A$^+$) mRNA by oligo (dT) chromatography. A mixture of oligo (dT)-primed and random-primed mRNA was converted to cDNA using the Superscript Choice System (Bethesda Research Labs, Gaithersburg, Md.). cDNA was ligated into the cloning vector λZAPII (Strategene, La Jolla, Calif.), packaged into phage heads using commercially-available packaging extracts (Strategene) and used to infect E. coli. Lawns of infected bacterial cells were used to make plaque lifts for hybridization using standard conditions (see Sambrook, et al., ibid.).

This cDNA library was hybridized with a $^{32}$P-labeled oligonucleotide having the following sequence:

5'-CTG(A/G)GC(A/G)ATGAA(A/G)ATGGCAGCCAGGGC(C/T)TCATACAGGGCTGTGCC-(A/G)TCCATGTT(A/G)ATGGT(A/G)GC-3'.  (SEQ ID NO: 1)

(This oligonucleotide was obtained commercially from Oligos, Etc., Wilsonville, Oreg.). This oligonucleotide was chosen on the basis of shared homology between a cloned rat glutamate transporter gene (GLAST1) and the bacterial glutamate transporter gene gltP (see Storck et al, ibid. and Wallace et al., ibid.), which suggested an important and conserved structural motif. Hybridization was performed at 50° C. in a solution containing 0.5M $Na_2HPO_4$ (pH 7.15)/ 7% sodium dodecyl sulfate (SDS) and the filters were washed at 60° C. in 2X SSPE [0.36M NaCl/20 mM sodium phosphate (pH 7.7)/2 mM ethylenediamine tetraacetic acid (EDTA)] and 1% SDS. Hybridizing clones were identified by autoradiography at −70° C. using tungsten-containing intensifying screens (DuPont-NEN, Wilmington, Del.).

More than 20 positively-hybridizing clones were detected in screening experiments using the above-described primer. One of these clones was excised from the cloning vector in vivo by superinfection with a defective filamentous phage that recognizes and excises cloned insert sequences along with adjacent modified phage replication-form sequences (termed pBluescript SK and available from Strategene). This clone contained a 2.7 kilobase (kb) insert, which was sequenced using the dideoxy-chain termination method of Sanger et al. (1977, Proc. Natl. Acad. Sci. USA 74: 5463), using Sequenase 2.0, a modified form of bacteriophage T7 DNA polymerase (U.S. Biochemical Corp., Cleveland, Ohio). The nucleotide sequence of the portion of this clone containing an open reading frame (encoding the ASCT1 gene) is shown in FIG. 1 1.

This ASCT1 clone (SEQ ID No.:2) was found to be comprised of about 180 bp of 5' untranslated region, about 900 bp of 3' untranslated region and an open reading frame of 1596 bp encoding the ASCT1 transporter protein (comprising 532 amino acids). The initiator methionine codon was found to be the first methionine codon 3' to an in-frame stop codon and embedded within the consensus sequence for eukaryotic translation initiation (see Kozak, 1987, Nucleic Acids Res 15: 8125–8132). The ASCT1 amino acid sequence (SEQ ID No.:3; also shown in FIG. 1) was found to exhibit similarity to other known glutamate transporter subtypes (an amino acid sequence comparison is shown in FIG. 5). An amino acid comparison between glutamate transporters from rat (GLAST1 and GLT-1) and rabbit (EAAC1) showed 39%, 34% and 39% sequence identity (respectively) between these amino acid transporter proteins (shown in FIG. 5 by shaded boxes). This degree of sequence identity is comparable to the sequence identity between these glutamate subtypes themselves. Both the amino and carboxyl termini were found to be divergent between these transporter proteins, and diversity was also found in the extracellular domains of these putative protein sequences, which contain conserved potential N-glycosylation sites (shown in FIG. 5 by open boxes). It was noted that a highly conserved sequence (comprising the amino acids —LYEA—) in the glutamate transporters was replaced by the unrelated amino acid sequence —IFQC— in the ASCT1 sequence (at positions 385–387 of the ASCT1 amino acid sequence shown in FIG. 5). 6–10 putative transmembrane domains were found using the algorithm of Eisenberg et al. (1984, J. Molec. Biol. 179: 125–142). On the basis of these dam ASCT1 was determined to encode a related but distinct and novel member of the amino acid transporter family.

EXAMPLE 2

Isolation of Human Excitatory Amino Acid Transporter cDNA

The remaining (>20) positively-hybridizing dones from the human motor cortex cDNA library detected by hybridization with the primer described in Example 1 (SEQ ID No. :1) were isolated and the corresponding plasmids obtained by in vivo excision after superinfection with defective phage as described in Example 1 above. These resulting plasmids were isolated and purified using conventional techniques (see Sambrook et al., ibid.). Four classes of clones were distinguished based on differential hybridization experiments using each clone as a hybridization probe against a panel of the remaining clones one after another, where conditions of hybridization stringency were varied to distinguish between each of the classes.

Representative clones from each class were sequenced as described in Example 1. One class of clones represented the ASCT1 cDNA sequences described in Example 1. The other three classes were found to encode novel proteins having amino acid sequences homologous to but distinct from the human ASCT1 sequence. Clone GT5 was determined to contain a 4.0 kb insert encoding a protein having a predicted amino acid sequence (termed EAAT1; SEQ ID No.:4) homologous to but distinct from the rat GLAST1 cDNA clone of Storck et al. (ibid.). Clone GT13 was determined to contain a 2.5 kb insert comprising an open reading frame corresponding to a full-length coding sequence for a novel human transporter gene termed EAAT2 (SEQ ID No. :6). Clone GT11 was found to contain a partial sequence of another novel human transporter termed EAAT3. The EAAT3 clone was used to re-screen the cDNA library described in Example 1. The result of these re-screening experiments was the isolation of Clone GT11B containing a full-length open reading frame encoding EAAT3 (SEQ ID No. :8).

FIG. 11 shows the results of alignment of the predicted amino acid sequences of the three novel glutamate transporters of the invention. Nine regions of Eisenberg algorithm predicted hydrophobicity are denoted by overlining, and potential sites of N-linked glycosylation (consensus sequence N-X-S/T, where X is any amino acid) are indicated by the circles asparagine (N) residues. EAAT1 shares 47% (253/542) amino acid sequence identity with EAAT2 and 46% (262/574) sequence identity with EAAT3, whereas the EAAT2 sequence is 45% (259/574) identical to the predicted EAAT3 sequence. Cross-species comparisons of the predicted amino acid sequences of these novel human glutamate transporters revealed the following relationships: EAAT1 was found to be 96% homologous with the rat GLAST1 sequence (Storck et al., ibid.); EAAT2 was found to be 90% homologous with the rat GLT1 sequence (Pines et al., 1992, ibid.); and EAAT3 was found to be 93% homologous with the rabbit EAAC1 sequence (Kanai & Hediger, 1992, ibid.). These results indicate that EAAT1, EAAT2 and EAAT3 are related but distinct members of the glutamate transporter family of amino acid transporters.

EXAMPLE 3

Functional Expression of the ASCT1 Amino Acid Transporter Gene in Xenopus Oocytes The sequence similarity between ASCT1 and the glutamate transporters GLAST1, EAAC1 and GLT-1 suggested that the protein encoded by ASCT1 was an amino acid transporter. The ability of the ASCT1 gene product to transport amino acids, and the identity of which amino acids might be transported by this gene product, was assayed in *Xenopus laevis* oocytes following microinjection of in vitro synthesized ASCT1 RNA.

Briefly, the coding sequence of the ASCT1 cDNA was isolated with unique flanking restriction sites using a PCR-based assay. In this assay, each of the complementary primers used for PCR amplification of the coding sequence contained a sequence encoding a unique restriction enzyme recognition site at the 5' terminus of each PCR primer. For ASCT1, the sense primer contained a KpnI recognition sequence (GGTAC↓C), and the antisense primer contained an XbaI recognition sequence (T↓CTAGA) at their respective 5' termini. Each of the PCR primers used for amplifying ASCT1 sequences had the following sequence:
ASCT1. Sense primer:
5'-CGCGGGTACCGCCATGGAGAAGAGCAAC-3' (SEQ ID NO: 10);
ASCT1 antisense primer:
5'-CGCGTCTAGATCACAGAACCGACTCCTTG-3' (SEQ ID NO: 11).

PCR amplification was performed for 30 cycles, each cycle comprising 1 minute at 94° C., 30 seconds at 55° C. and 2 minutes at 72° C. Following the PCR, the product of the amplification reaction was purified using standard techniques (Saiki et at., 1988, Science 239: 487–491). The DNA then digested with the restriction enzymes KpnI and XbaI and then cloned into the polylinker of an oocyte transcription vector (pOTV; see Wang et al., 1991, Nature 352: 729–731) that had been digested with KpnI and XbaI. Synthetic RNA was then transcribed in vitro from this clone using the method of Kavanaugh et al. (1992, J. Biol. Chem. 267: 22007–22009) employing bacteriophage T7 RNA polymerase (New England Biolabs, Beverly, Mass.). 20–50 nL of ASCT1 RNA (at a concentration of about 400/xg/mL) was injected into defolliculated stage V–VI Xenopus oocytes excised from female Xenopus laevis anesthetized by immersion in 3-aminobenzoic acid for 60 min. Excised oocytes were treated with collagenase II (Sigma Chemical Co., St. Louis, Mo.) in calcium-free Barth's saline solution [comprising 88 mM NaCl, 1 mM KCl, 2.4 mM $NaHCO_3$, 0.82 mM $MgSO_4$, 7.5 mM Tris-HCl (pH 7.6), 50 U/mL Nystatin (Sigma) and 0.1 mg/mL gentamycin (Sigma)] for 60 min., and then incubated overnight at 15° C. in 50% Leibowitz's L-15 media (Grand Island Biological Co. (GIBCO), Long Island, N.Y.). After overnight incubation the ooeytes were mechanically defolliculated and then were injected with ASCT-1 RNA and incubated at 19° C. for 48 h (see Kim et at., 1991, Nature 352:725–728 for further details of Xenopus oocyte preparation and microinjection).

Amino acid transport in such oocytes was assayed using [$^3$H-I] alanine, [$^3$H] serine or [$^{35}$S] cysteine (obtained from New England Nuclear, Boston, Mass.). Briefly, microinjected oocytes were patch-clamped at −60 mV using a Dagan TEV-200 clamp amplifier with an Axon Instruments (Foster City, Calif.) TL-1 A/D interface controlled by pCLAMP software (Axon Instruments) (see Kavanaugh et al., 1992, J. Biol. Chem. 267:22007–22009 for a detailed review of this methodology) and continuously superfused with ND-96 buffer (consisting of 96 mM NACl/2 mM KCl/1.8 mM $CaCl_2$/1 mM $MgCl_2$/5 mM HEPES, pH 7.5). For transport measurements, this solution was changed to a solution containing varying concentrations of the radiolabeled amino acids in ND-96 buffer.

Figure 6B:
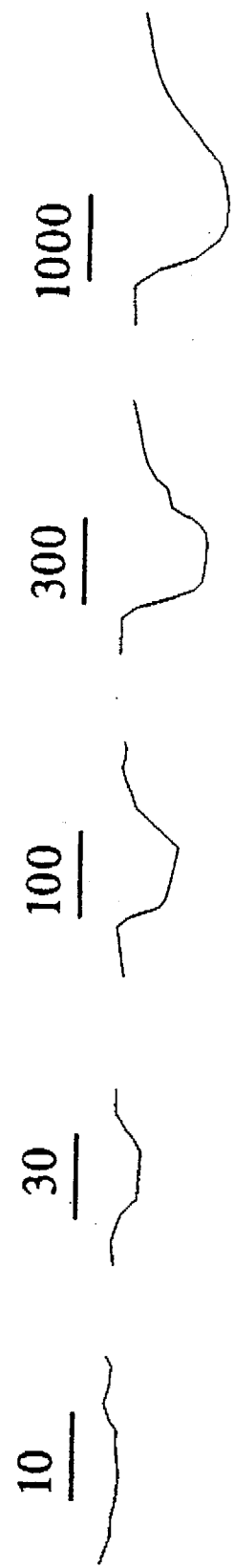
Figure 6C:
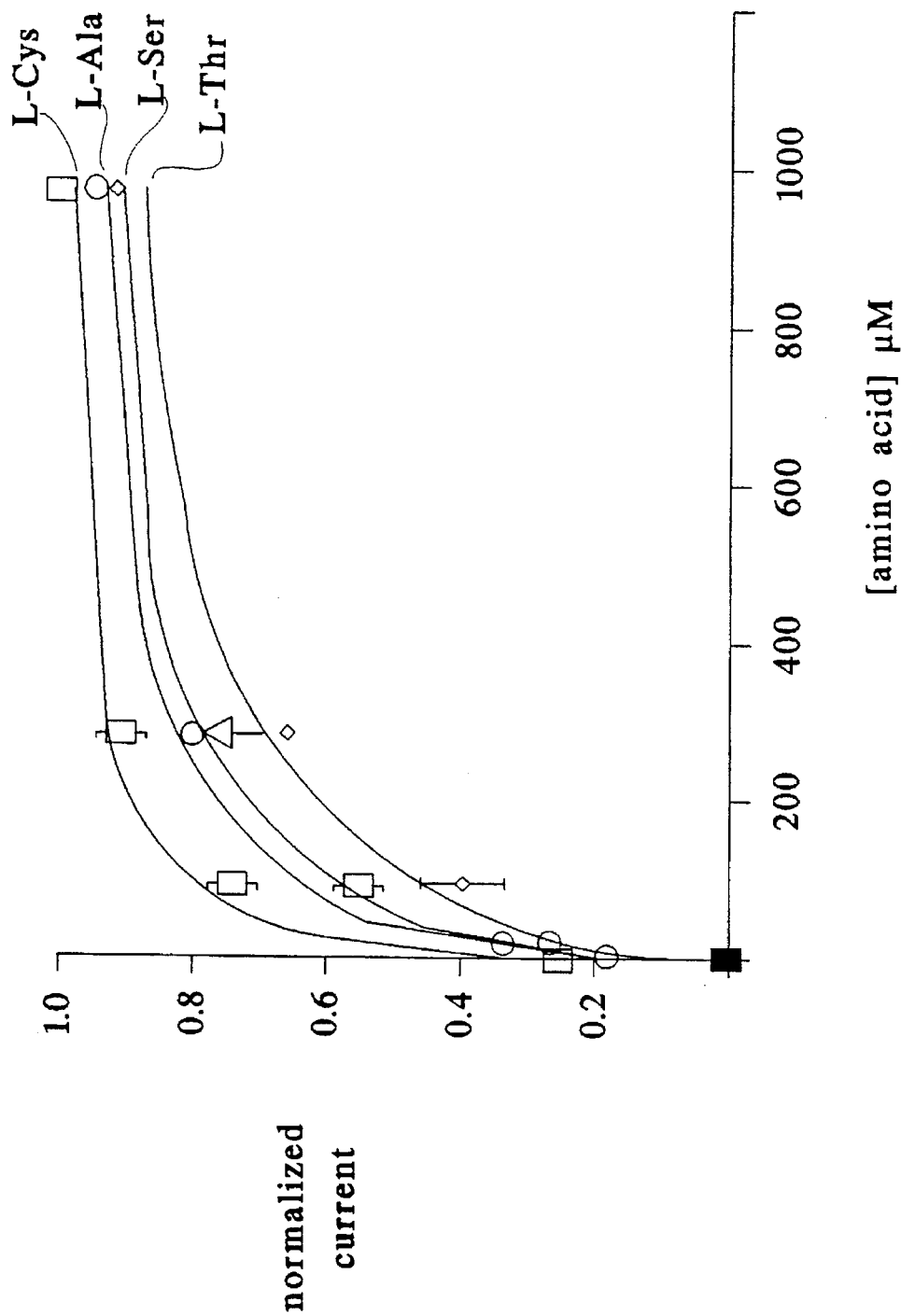
Figure 7A:
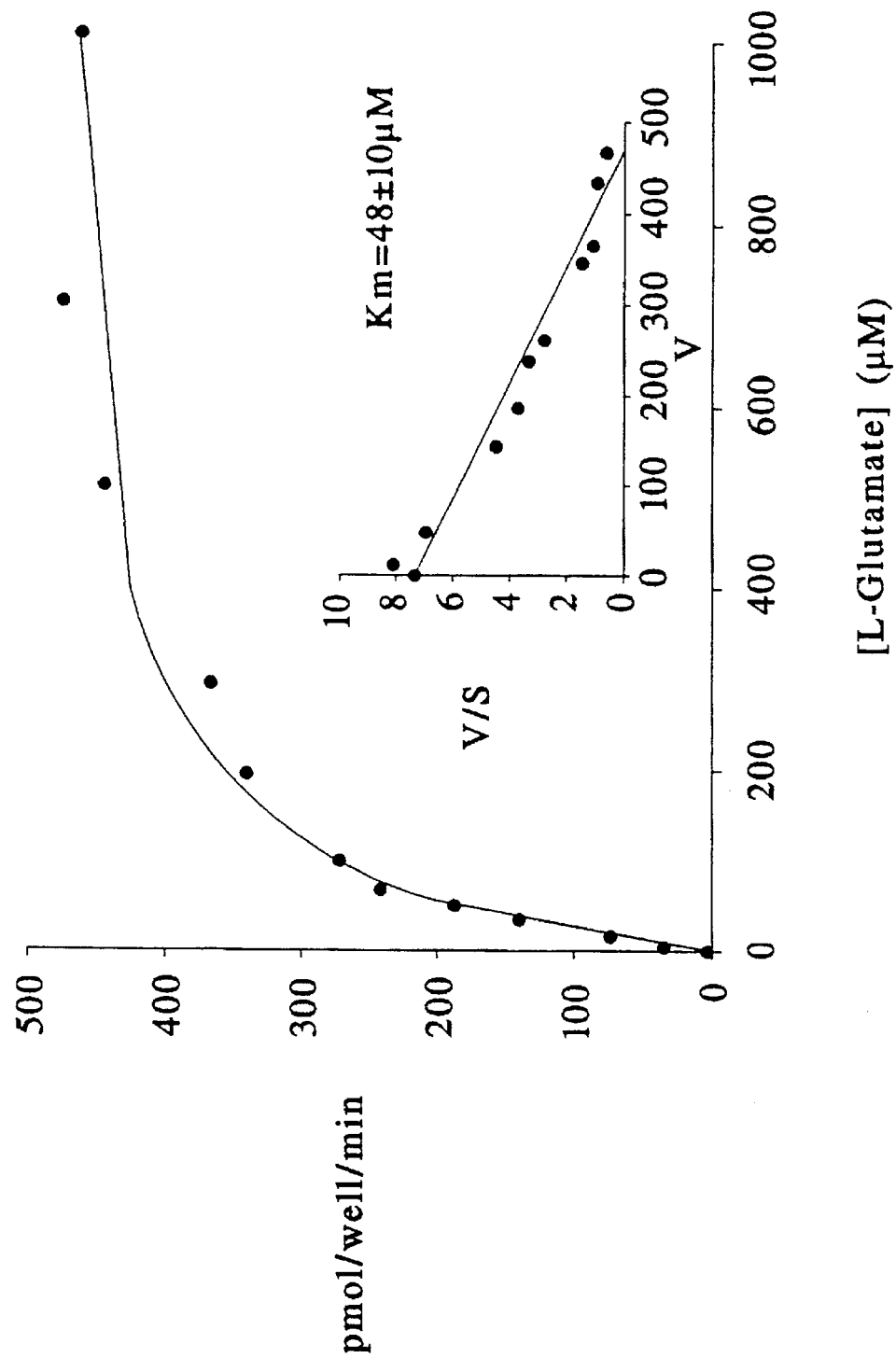
FIG. 7 presents glutamate transporter kinetics of EAAT1 (Panels A and B), EAAT2 (Panels C and D) and EAAT3 (Panels E and F).
Figure 7B:
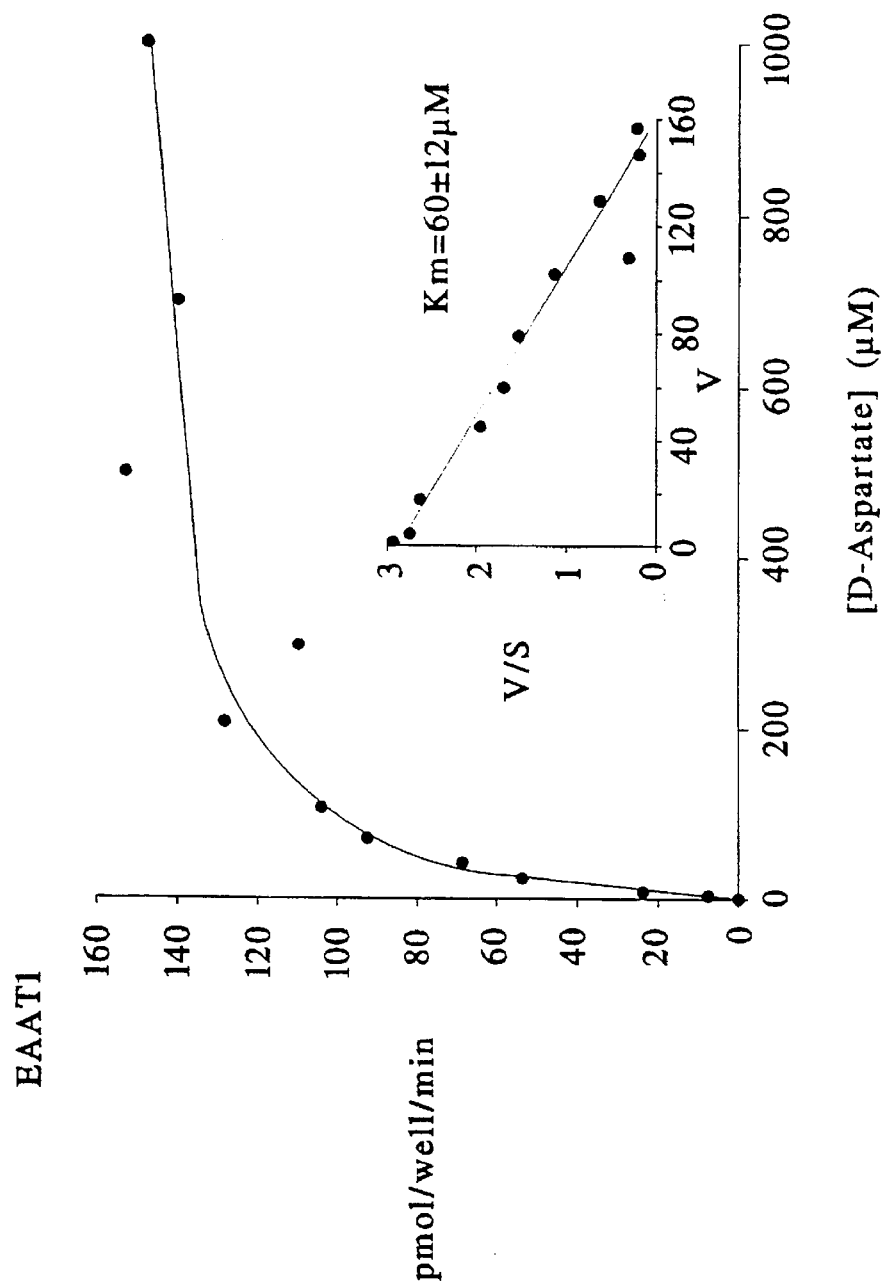
Figure 7C:
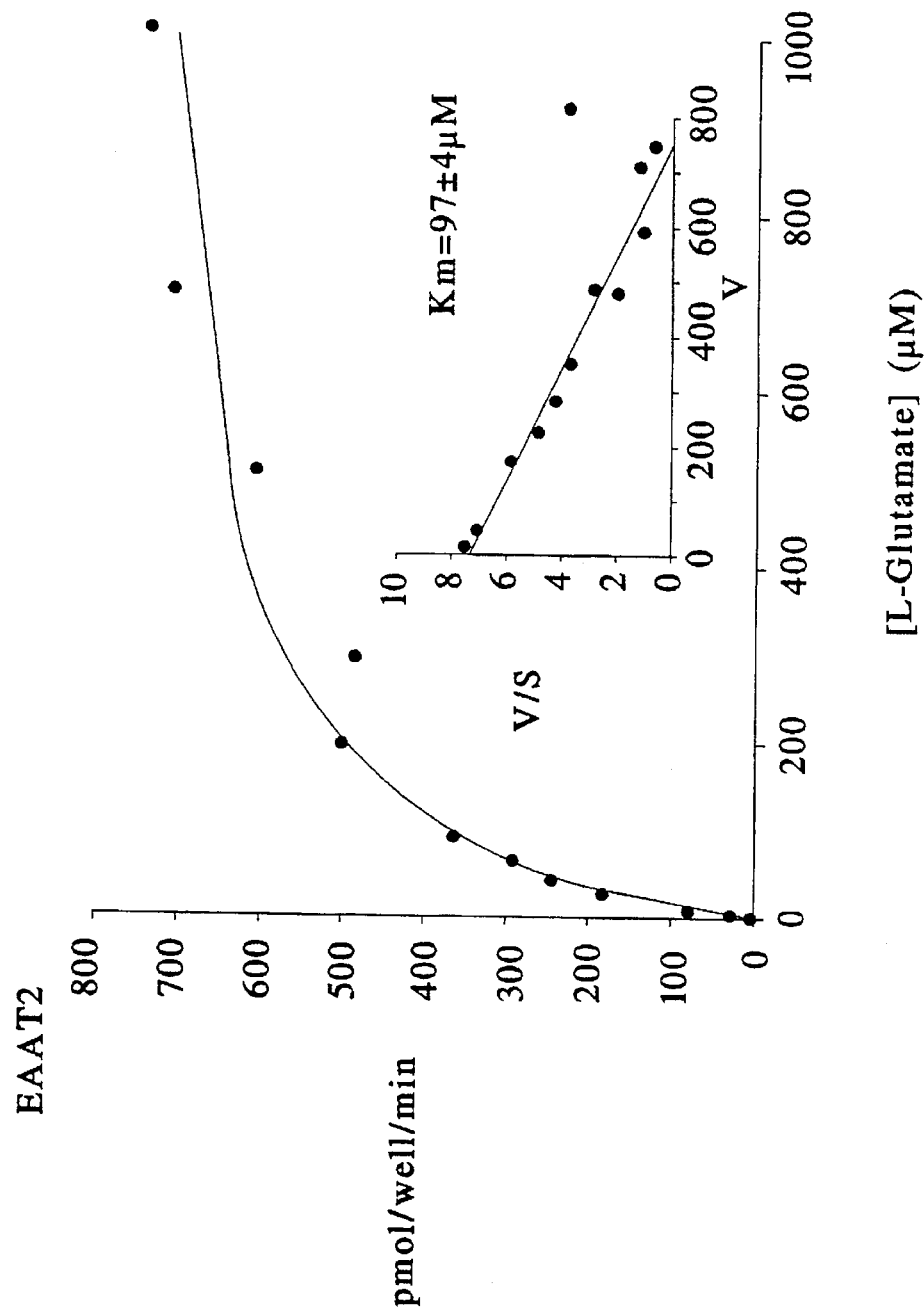
Figure 7D:
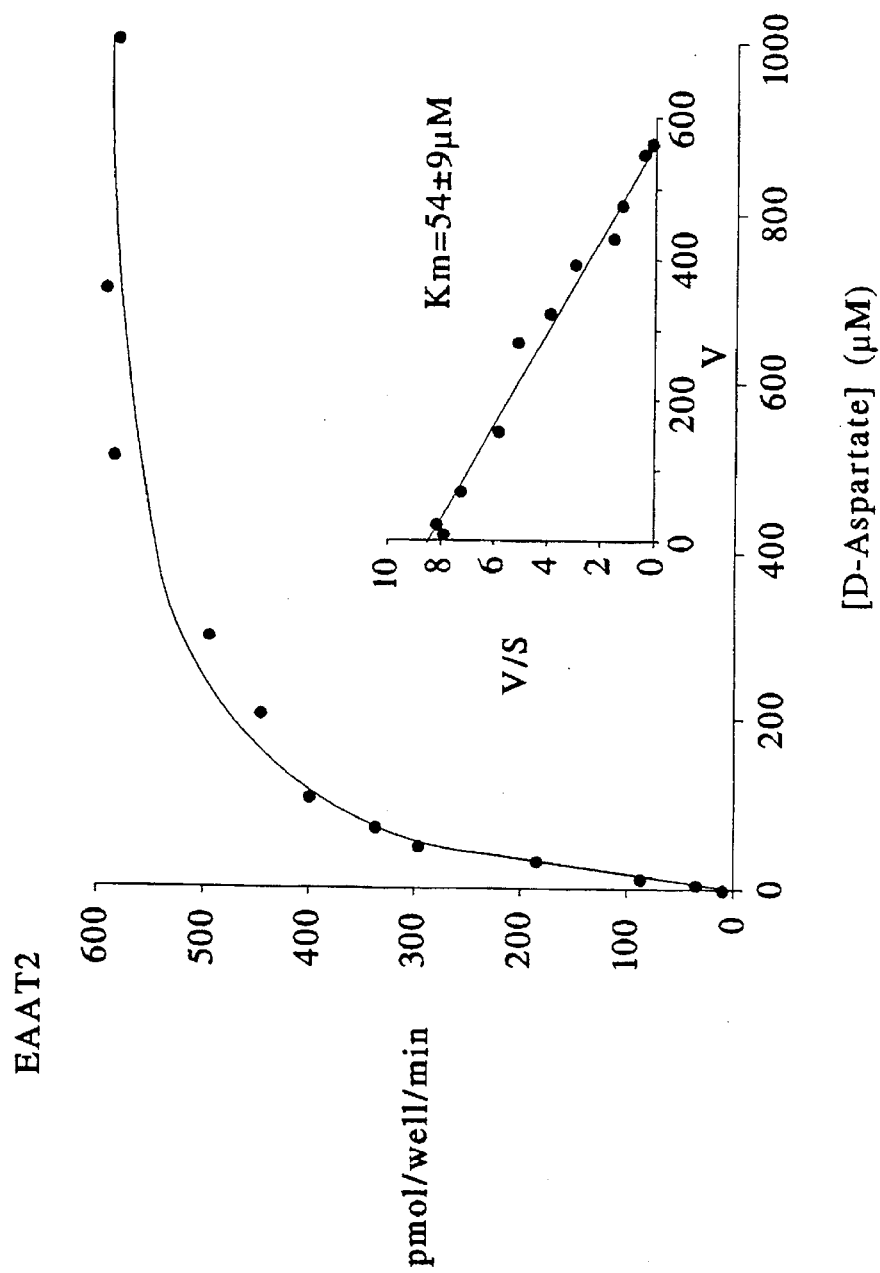
Figure 7E:
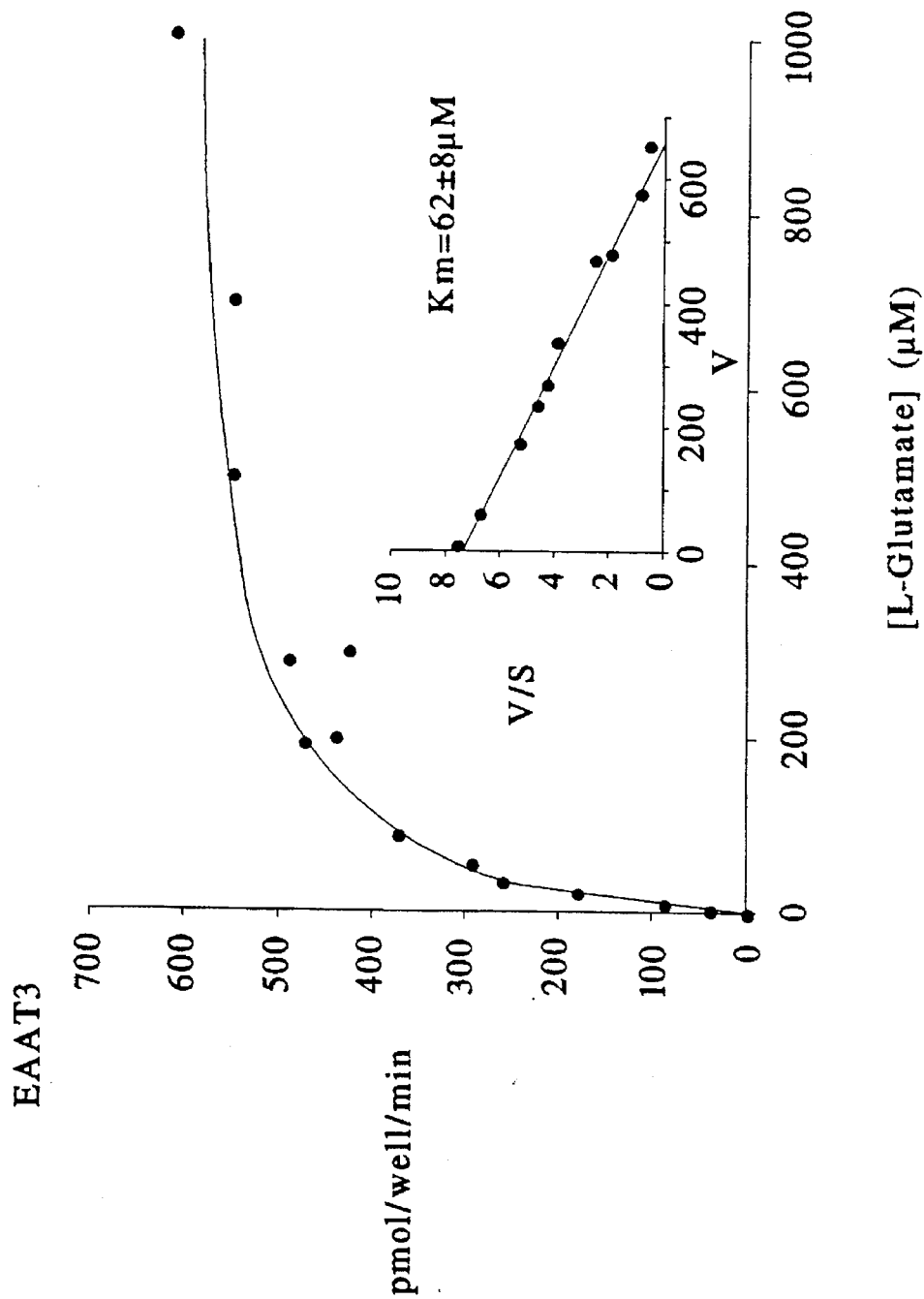
Figure 7F:
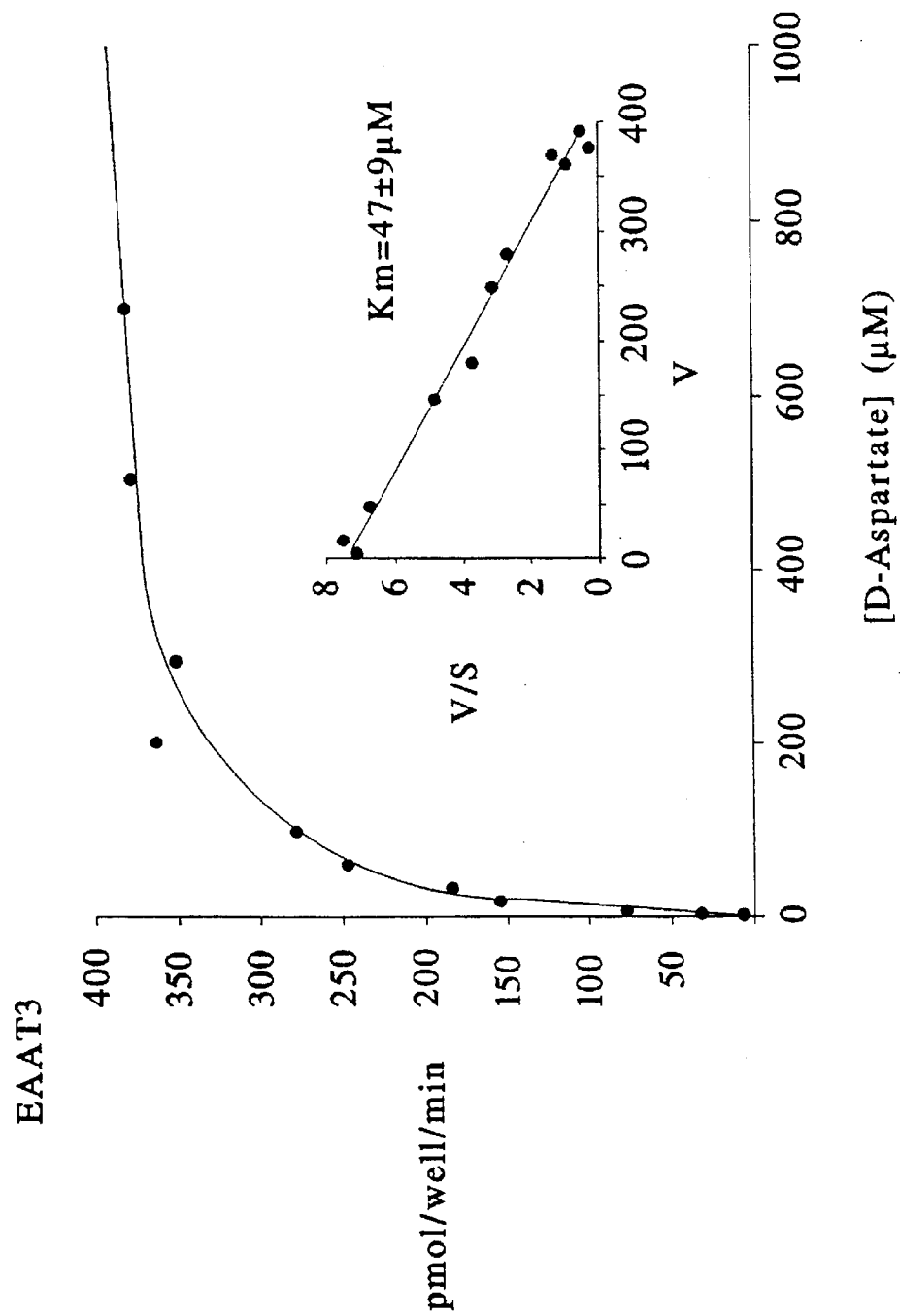

Three types of experiments were performed, the results of each being shown in FIG. 6. As shown in Panel A, when such oocytes were contacted with ND-96 buffer containing L-alanine, L-serine or L-cysteine, a hyperpolarization of the cell plasma membrane was produced as the result of inward currents of $Na^+$ ion, as has been associated with other known amino acid transporters (see Nicholls, ibid.). In contrast, the amino acids L-lysine, L-glutamine, proline, glycine, methionine, arginine, glutamine, asparagine, and leucine, and the amino acid analogues N-methylalanine, had no effect at much higher concentrations (i.e., about 1 mM). Another amino acid analogue, 2-methylaminoisobutyric acid (MAIB), which is known to be specific for the amino acid transporter type A (Christensen et al., 1967, J. Biol. Chem. 242: 5237–5246), also had no effect at concentrations of 1 mM. Further, in competition experiments, contacting such oocytes with a solution containing MAIB at a concentration of 10 mM had no effect on the rate of uptake of [$^3$H] alanine present at 100 μM. The response of the oocytes was also stereospecific (D-alanine was found to produce only 12±3% of the response produced by treatment of these oocytes with L-alanine) and $Na^+$ ion-specific (no response was detected when $Na^+$ ions were replaced by tris-hydroxyethylaminomethane buffer, shown in Panel A). The rate of radiolabeled amino acid uptake (in pmol/min per oocyte, determined at an amino acid concentration of 100 μM) for the amino acids alanine, cysteine and serine are shown in Table I.

The uptake currents measured in ASCT1-injected oocytes were found to be both dose-dependent and saturable. FIG. 6, Panel B illustrates the dose-dependency of the electrochemical response of ASCT1-injected oocytes to L-alanine. The intensity of the response (equivalent to the amount of current flow into the cell) increased with the concentration of L-alanine from 10 μM to 1 mM. The saturability of this response is shown in FIG. 6, Panel C. In this Figure, the current, normalized to the maximum response obtained with L-alanine, is shown plotted against the extracellular amino acid concentration of each amino acid tested. For the L-stereoisomers of alanine, serine, cysteine and threonine, the inward current flux was found to saturate and reach a plateau at concentrations from 400–1000 μM. More detailed analyses of the kinetics of amino acid influx were performed by least squares linear regression analysis of induced inward current ([I]) plotted as a function of substrate amino acid concentration ([S]), using the equation shown in the legend of Table II. Data were averaged from all oocytes tested, and the results expressed as the mean ± standard error are shown in Table II.

These results indicated that the cloned ASCT1 cDNA derived from human motor cortex mRNA encoded an amino acid transporter that was specific for Alanine, Serine, Cysteine (and Threonine) and that amino acid transport activity was accompanied by an inward current flow mediated by sodium ions. These results demonstrated that the novel amino acid transporter isolated herein was related to but distinct from other, known transporters, such as the so-called ASC amino acid transporters (Christensen et al., ibid.).

EXAMPLE 4

Functional Expression of the Glutamate Amino Acid Transporter Genes in Xenopus Oocytes Similar series of experiments were performed using RNA synthesized in vitro from constructs containing each of the cloned glutamine transporter genes of the invention. In these experiments, each of the PCR primers used to amplify each of the glutamate transporter genes had the following sequence:
EAAT1 sense primer:
5'-CGCGGGTACCAATATGACTAAAAGCAATG-3' (SEQ ID NO:12);
EAAT1 antisense primer:
5'-CGCGTCTAGACTACATCTTGGTTTCACTG-3' (SEQ ID NO:13);

EAAT2 sense primer:
5'-CGCGGGTACCACCATGGCATCTACGGAAG-3' (SEQ ID NO:14);
EAAT2 antisense primer:
5'-CGCGTCTAGATTATTTCTCACGTTTCCAAG-3' (SEQ ID NO:15)
EAAT3 sense primer:
5'-CGCGGGTACCGCCATGGGGAAACCGGCG-3' (SEQ ID NO:16);
EAAT3 antisense primer
5'-CGCGGGATCCCTAGAACTGTGAGGTCTG-3' (SEQ ID NO:17).

As can be determined by inspection of these sequences, each of the sense primers contained a KpnI recognition sequence (GGTAC↓C), and each of the antisense primers contained an XbaI recognition sequence (T↓CTAGA) at the 5' terminus of each primer for EAAT1 and EAAT2. For EAAT3, the sense primer contained a KpnI recognition sequence, and the antisense primer contained a BamHI recognition sequence (G↓GATCC) at the 5' terminus of each primer.

PCR amplification was performed for 30 cycles, each cycle comprising 1 minute at 94° C., 30 seconds at 50° C. and 2 minutes at 72° C. Following the PCR, each of the PCR products was isolated and cloned into pOTV as described in Example 3, from which RNA encoding each glutamate transporter was synthesized in vitro as described.

Figure 12A:
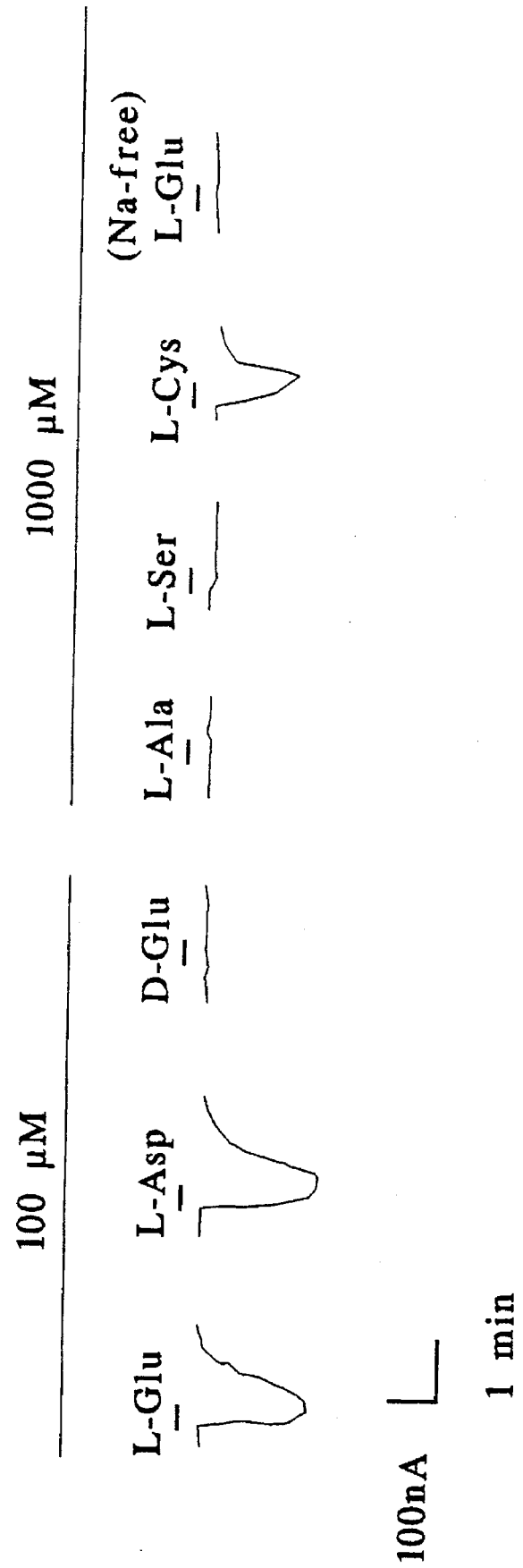
FIG. 12 illustrates electrogenic uptake of various amino acids (Panel A) and the concentration dependence of such uptake of L-glutamate (Panel B) in *Xenopus laevis* oocytes expressing the EAAT1 amino acid transporter.
Figure 12B:
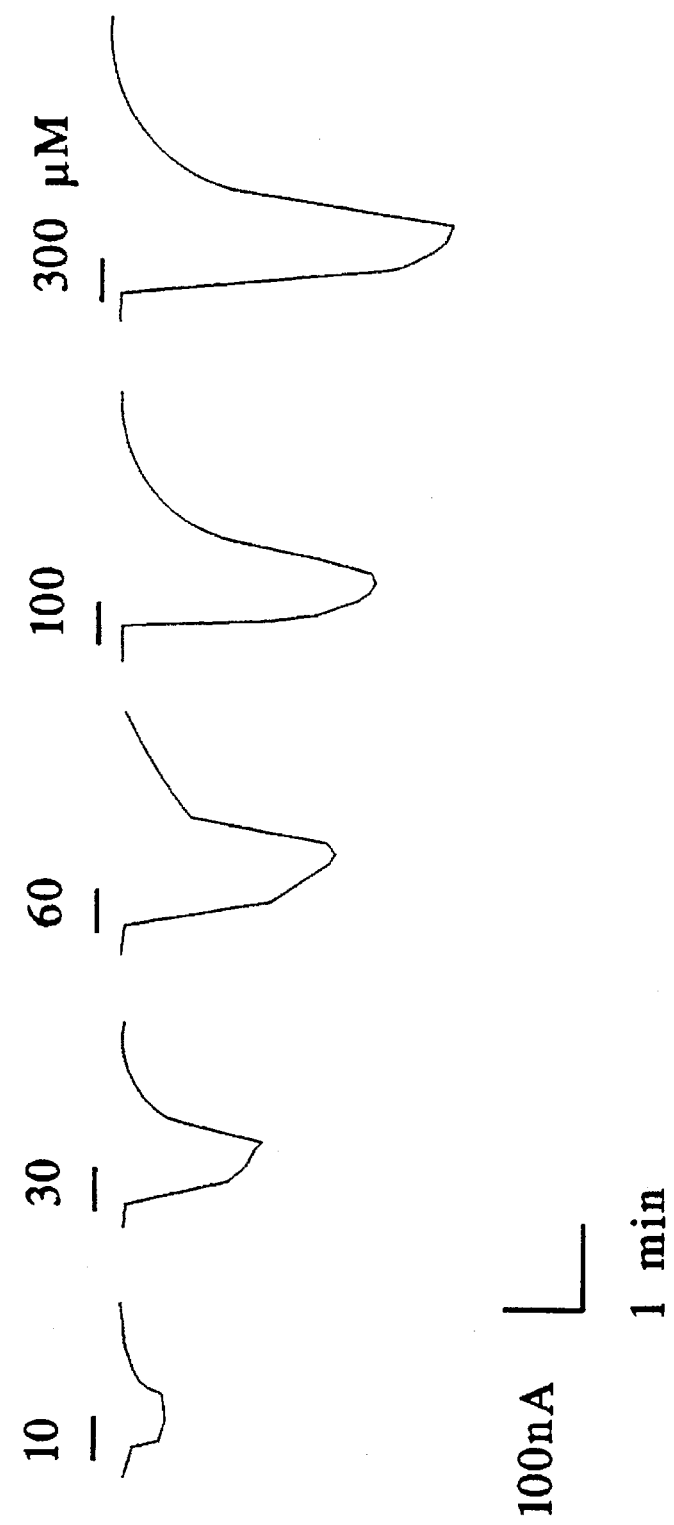
Figure 12C:
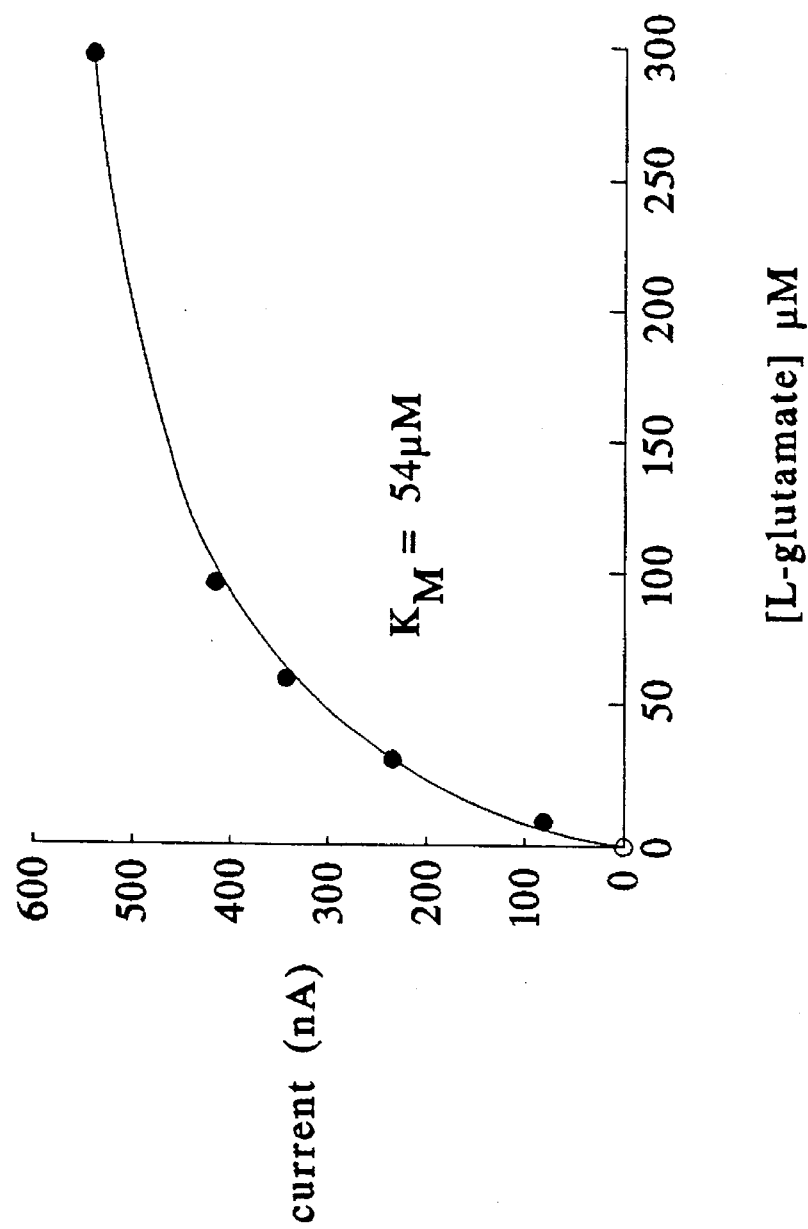

Such RNA preparations were each introduced into Xenopus oocytes as described in Example 3 to enable expression therein. Amino acid uptake experiments were performed on such oocytes expressing each of the glutamate transporters, also as described in Example 3. Results of such experiments are shown in FIG. 12. Panel A shows electrogenic uptake of various amino acids in EAAT1-expressing oocytes. Both L-glutamate and L-aspartate caused inward currents as high as several microamps when added to the incubation media (ND-96) at a concentration of 100 µM. In contrast, incubation of EAAT1-expressing oocytes with L-alanine and L-serine at ten-fold higher concentrations (i.e., 1000 µM) did not result in electrogenic uptake of these amino acids. Uptake was found to be stereospecific, since L-glutamate incubation did not result in the generation of an inward electric current, and sodium-ion specific, since electrogenic uptake of L-glutamate was abolished by incubation in sodium ion-free media (choline was used to replace sodium in these incubations).

These experiments also demonstrated the surprising result that cysteine, when present at high enough extracellular concentrations (i.e., 1000 µM) was capable of being electrogenically transported by the EAAT1 transporter. Cysteine had not previously been reported to be a glutamate transporter substrate; however, amino acid sequence analysis of the EAAT1 transporter showed structural similarities between EAAT1 and the ASCT1 transporter, which was demonstrated herein to transport cysteine (see Example 3). As will be discussed in detail below, the EAAT1 transporter displays a $K_m$ for glutamate of 54 µM; in contrast, the $K_m$ for cysteine was found to be 300 µM. The EAAT1 transporter thus displays a pattern of substrate specificity that is distinct from that of any known glutamate transporter.

Panel B of FIG. 12 illustrates the results of biochemical analysis of substrate affinity of the EAAT1 transporter for glutamate, said results being plotted as current versus substrate concentration to yield an estimate of the $K_m$. These experiments were performed essentially as described for the ASCT1 transporter in Example 3. Patch-clamped oocytes expressing the EAAT1 transporter were incubated with varying extracellular concentrations of L-glutamate, and the magnitude of the resulting inward currents determined. From these experiments, the plotted relationship between the magnitude of the inward current and the extracellular L-glutamate concentration was determined, resulting in an estimate for $K_m$ equal to 54 µM for L-glutamate. These results were in good agreement with results obtained in COS-7 cells expressing the EAAT1 transporter, described hereinbelow (see Example 5).

EXAMPLE 5

Functional Expression of the Amino Acid Transporter Genes in COS-7 Cells

DNA fragments comprising the coding sequences of the novel glutamate transporter genes of the invention were excised from the pOTV constructs described in Example 3 and subcloned into the mammalian expression plasmid pCMV5 (Anderson et al., 1989, J. Biol. Chem. 264: 8222–8229). These mammalian expression constructs were used for transient expression assays of glutamate transporter protein function after transfection of each of these constructs into COS-7 cells (Gluzman, 1981, Cell 23:175–182).

Each of the pCMV5 constructs corresponding to EAAT1, EAAT2 and EAAT3 were introduced into COS-7 cells by DEAE-dextran facilitated transfection (see Sambrook et al., ibid.). Two day following transfection, the transfected cells were washed three times in phosphate-buffered saline (PBS) and then incubated with a mixture of radiolabeled amino acid ([$^3$H]-L-glutamate or [$^3$H]-D-aspartate; Dupont-NEN) and non-radiolabeled amino acid for 10 min. After incubation, the cells were washed three times with ice-cold PBS, solubilized with a solution of 0.1% sodium dodecyl sulfate (SDS) and the amount of radioactivity associated with the cells determined using standard liquid scintillation counting methods. The results of these experiments showed that cells transfected with each of the glutamate transporter constructs accumulated significantly-higher (between 10- and 100-fold higher) amounts of radioactivity than did mock (i.e., pCMV5 plasmid) transfected COS-7 cells (which accumulation represented endogenous COS-7 cell uptake of radioactive glutamate). The course of radioactive glutamate uptake was found to be linear for at least 20 min in assays performed at room temperature.

These results are shown in FIG. 7. In the Figure, EAAT1 transporter kinetics of glutamate uptake are depicted in Panel A and of aspartate are shown in Panel B. Similarly, EAAT2 kinetics for glutamate and aspartate are shown in Panels C and D, respectively. Finally, EAAT3 kinetics are shown in Panel E (glutamate) and Panel F (aspartate). Each data point was determined by incubating a COS cell culture transfected with the appropriate pCMV5-glutamate transporter clone with 100 nM of radiolabeled amino acid and increasing amounts of unlabeled amino acid. Results are plotted as uptake velocity (in pmol/cell culture/rain) minus endogenous uptake versus total amino acid concentration, and each data point was performed in triplicate. The results show that both glutamate and aspartate uptake mediated by each of the three novel human glutamate transporters is saturable. Insets in each Panel depict Eadie-Hofstee plots of initial velocity data, from which $K_m$ values were determined. The $K_m$ values are shown as the mean ± standard error based on at least three independent experients. These results show that each of the three novel rater proteins comprising the instant invention is functionally competent as an amino acid transporter when expressed in a culture of mammalian cells, and that each of the novel transporters encoded by the cDNA clones EAAT1, EAAT2 and EAAT3 displays a collection of biochemical properties consistent with their designation as human glutamate transporter proteins.

EXAMPLE 6

Inhibitor Potency Analyses Using COS-7 Cells Expressing Amino Acid Transporter Proteins COS-7 cell cultures transformed with pCMV5-human glutamate transporter constructs as described in Example 4 were used to characterize the pharmacological properties of each of these transporter proteins relative to a variety of known glutamate transporter inhibitors. These assays were performed essentially as described in Example 4, with the exception that varying amounts of each of a number of known inhibitor compounds were included in the incubations.

Figure 8A:
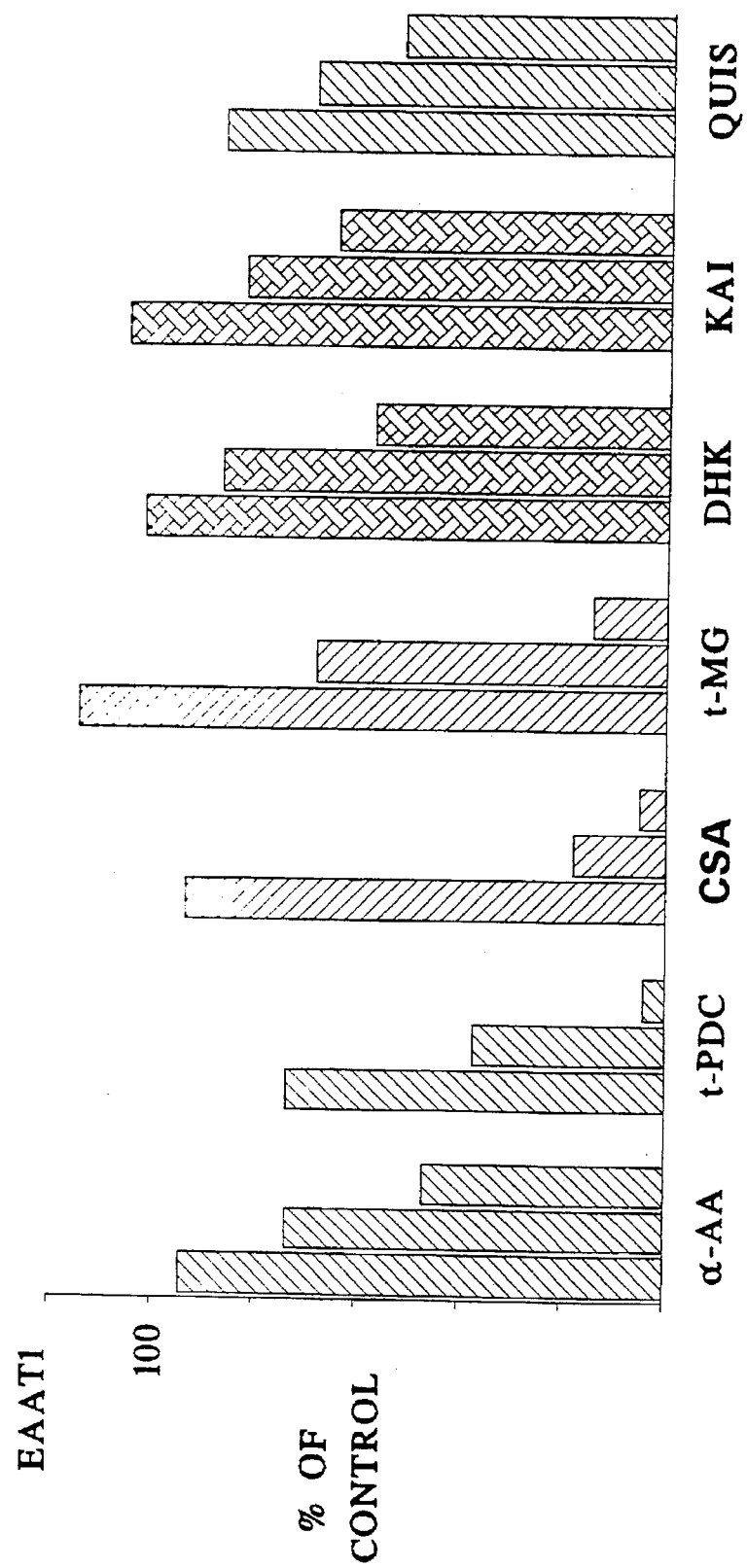
FIG. 8 represents the pharmacological responsiveness of glutamate transport by the human excitatory amino acid transporters EAAT1, EAAT2 and EAAT3 when contacted with the indicated competitors/inhibitors at the indicated concentrations.
Figure 8B:
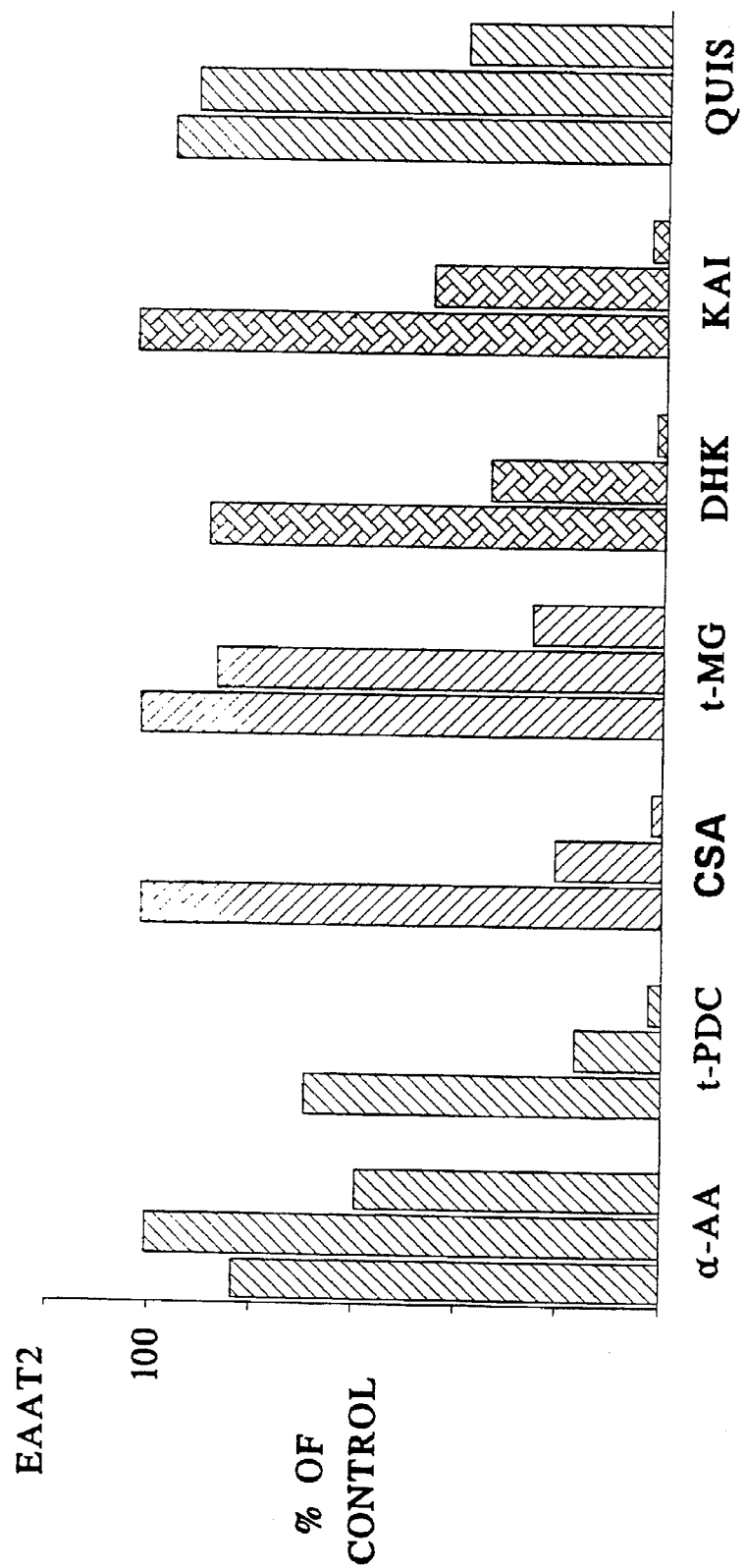
Figure 8C:
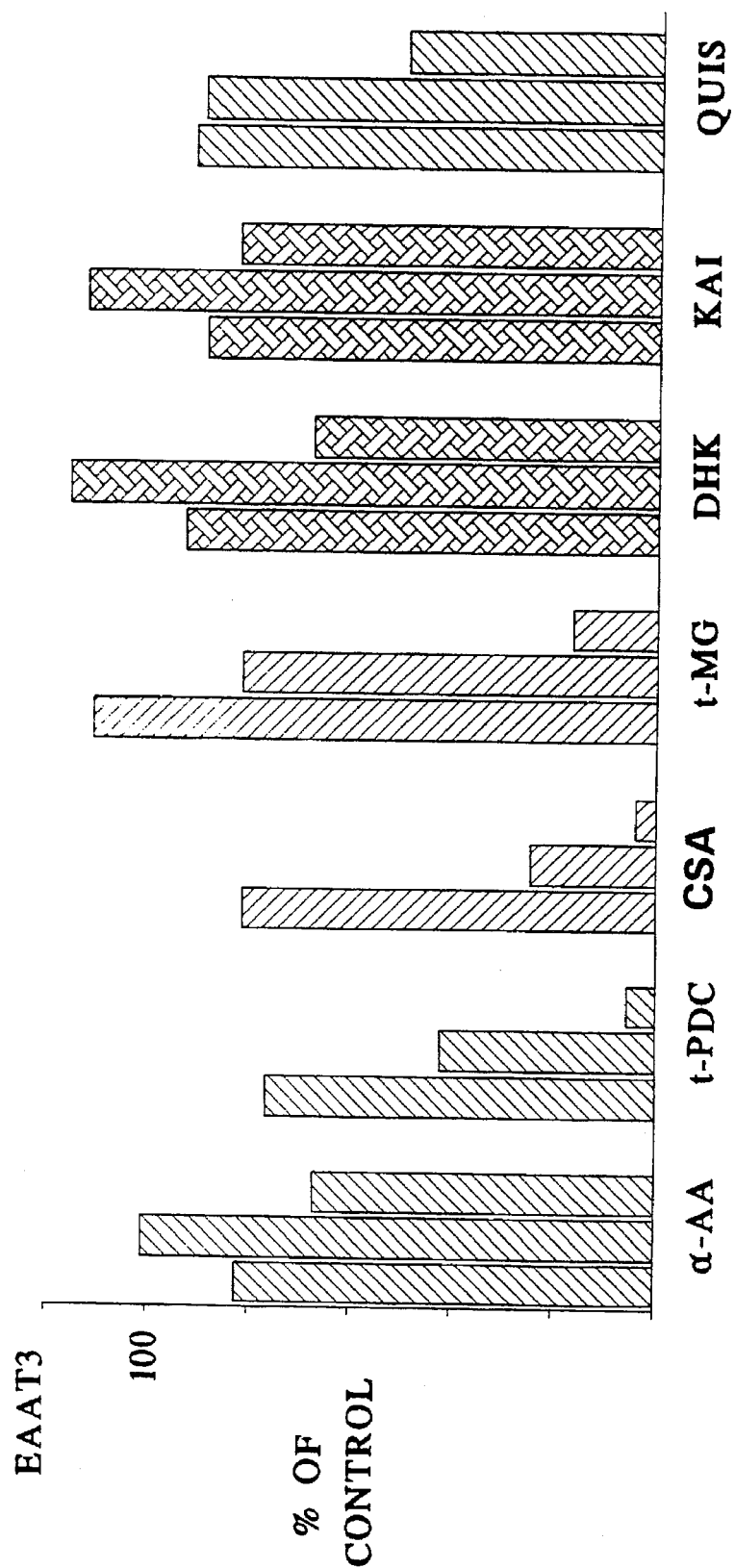

The results of these experiments are shown in FIG. 8. The data in FIG. 8 represent the pharmacological responsiveness of glutamate transport by the human excitatory amino acid transporters EAAT1, EAAT2 and EAAT3 when contacted with the following competitors/inhibitors: L-threo-β-hydroxyaspartate (THA); L-trans-pyrrolidine-2,4-dicarboxylate (PDC); L-serine-O-sulfate (SOS); dihydrokainate (DHK); and kainate (KAI). In these experiments, uptake of 1 µM of [$^3$H]-L-glutamate was determined in the presence of the indicated amounts of each of the inhibitors. As can be seen from the Figure, each of the glutamate transporter proteins of the invention displays a characteristic pattern of sensitivity to the inhibitors. Thus, the relative potency of inhibition of radiolabeled glutamate uptake was found to be as follows for the EAAT1 and EAAT3 transporter proteins:

THA<PDC<SOS<<DHK, KAI, whereas the inhibition pattern for EAAT2 was as follows:

PDC<THA<DHK<KAI<SOS.

These results, as well as results obtained from similar experiments performed with L-cysteate, L-cysteine sulfinic acid, β-glutarnate and L-aspartate-β-hydroxymate, are shown in Table III. Even though the relative pattern of inhibition was the same for EAAT1 and EAAT3, the results shown in the Table support the finding that each of the glutamate transporters of the invention is uniquely characterized by its sensitivity to this panel of glutamate uptake inhibitors.

In addition, a number of reported inhibitors were found to be ineffective when tested with COS cell culture expressing each of the novel glutamate transporter proteins of the invention. These include cis-1-aminocyclobutane-1,3-dicarboxylate, L-pyroglummic acid, S-sulfo-L-cysteine, N-acetyl aspartylglutamate, N-methyl-D-aspartate (NMDA) and quisqualate. α-aminoadipate, a classical inhibitor of glutamate uptake, exhibited only low potency when tested against all three EAAT subtypes. These results of functional assays support the conclusion arrived at from structural analysis (i.e., nucleic acid and amino acid sequence analyses) that the glutamate transporter cDNAs and proteins of the invention are novel mammalian transporter species.

EXAMPLE 7

Tissue Distribution of Amino Acid Transporter Expression

The tissue distribution of mRNA corresponding to expression of the amino acid transporters disclosed herein was determined in various tissues by Northern hybridization experiments (see Sambrook et al., ibid.). The results of these experiments are shown in FIGS. 9 and 10.

A panel of tissue samples was examined by Northern hybridization analysis performed under high stringency conditions as follows. A nylon filter containing 2 µg human peripheral tissue poly(A)$^+$ RNA was obtained from Clonetech Laboratories (Palo Alto, Calif.), and a similar filter was prepared containing human brain region RNA as follows. Total RNA was isolated from human brain region tissue obtained from the Oregon Brain Repository and 20 µg/region were size-fractionated by denaturing formaldehyde agarose gel electrophoresis (see Sambrook et al., ibid.). Fractionated RNA was then transferred to a nylon filter using the Northern blot/capillary-osmotic technique. Northern hybridization of both filters was performed individually with $^{32}$P-labeled amino acid transporter-specific probes for each transporter to be analyzed. Probes were derived from amino acid transporter coding sequences and labeled using $^{32}$P-labeled dCTP by the random primer method (Boehringer-Mannheim, Indianapolis Ind.). Filters were hybridized overnight at 42° C. individually with each radiolabeled probe (at a concentration of $10^6$ cpm/mL) in a solution of 5X SSPE/50% formamide/7.5X Denhardt's solution (comprising 0.15 g/100 mL each of Ficoll, polyvinylpyrrolidone and bovine serum albumin)/2% SDS and 100 µg/mL denatured salmon-sperm DNA. Following hybridization, filters were washed twice for 30 min at room temperature in 2X SSPE/0.1% SDS and twice for 20 min at 50° C. in 0.1 X SSPE/0.1% SDS. Hybridizing RNAs were visualized by autoradiography at −70° C. using intensifying screens. The filters were subsequently re-probed as described with a radiolabeled human β-actin probe (Clonetech) as a positive control.

Figure 9:
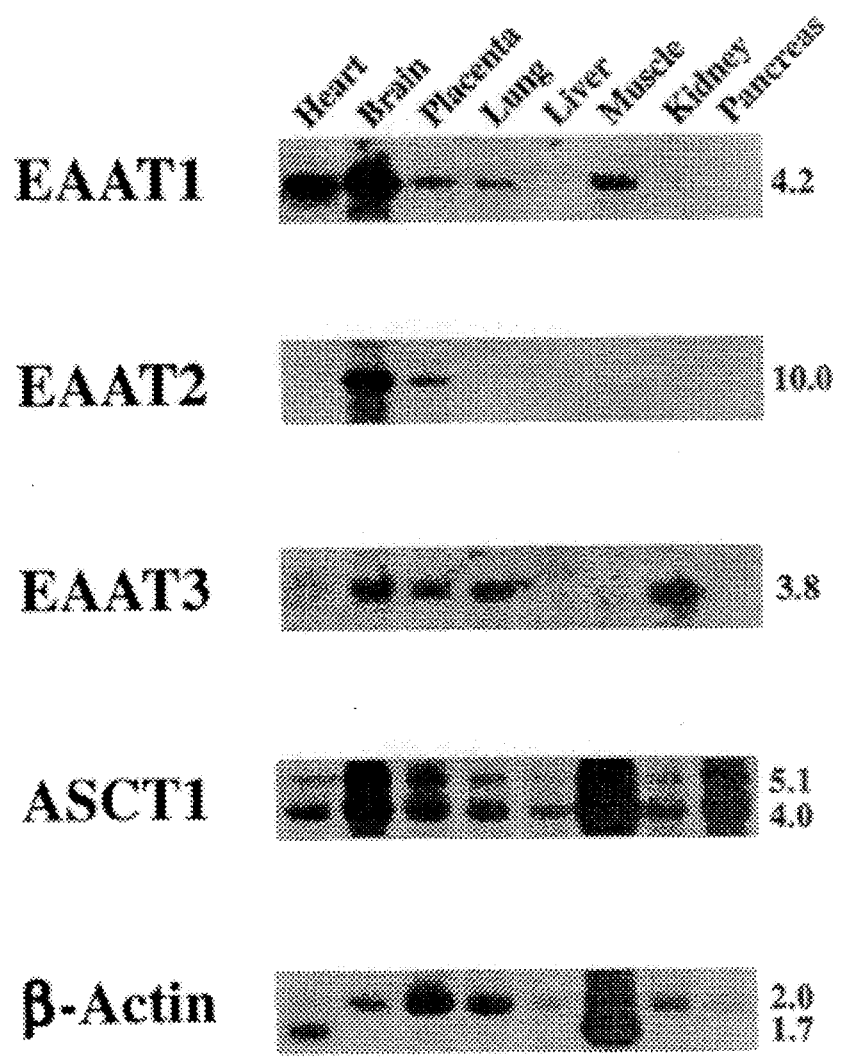
FIG. 9 shows the pattern of expression of EAAT1, EAAT2, EAAT3 and ASCT1 in human, tissues; β-actin is shown as a control for amount of RNA in each lane.
Figure 10:
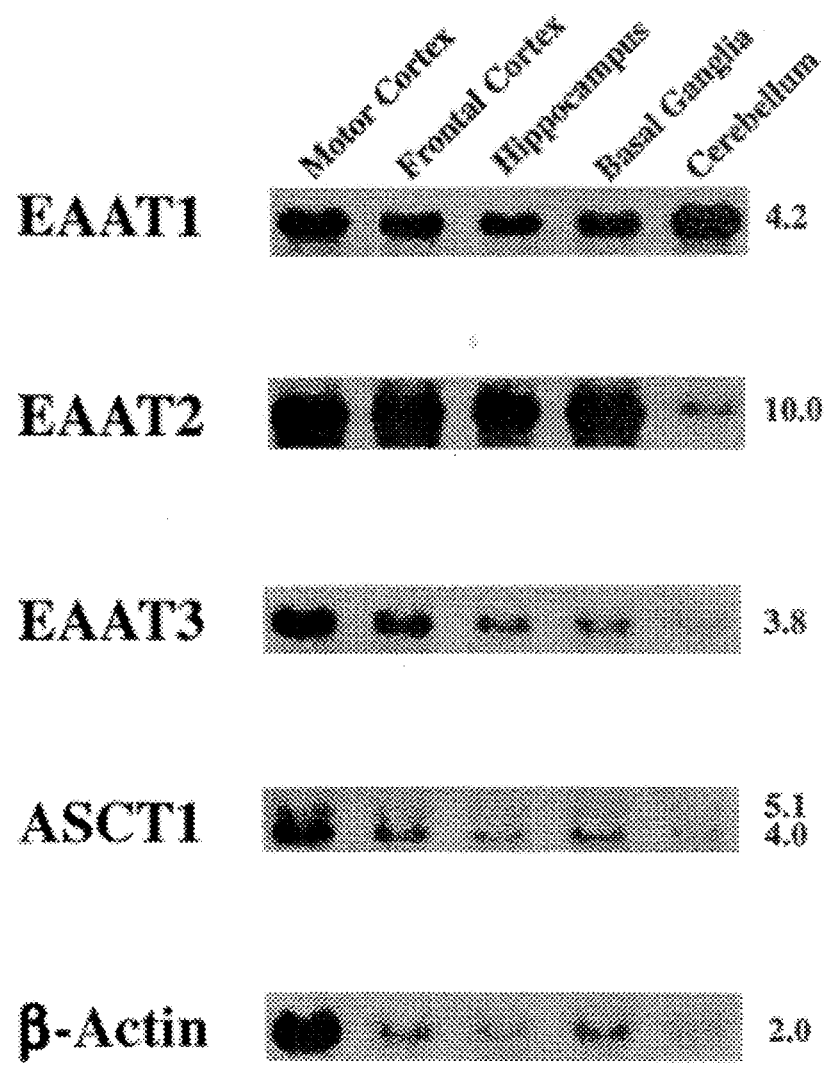
FIG. 10 shows the pattern of expression of EAAT1, EAAT2, EAAT3 and ASCT1 in human brain tissue, β-actin is shown as a control for the amount of RNA in each lane.

The results of these experiments are shown in FIGS. 9 and 10. FIG. 9 illustrates expression of each of the amino acid transporters in human heart, brain, placenta, lung, liver, muscle, kidney and pancreas. The size (in kb) of the transcripts corresponding to expression of each transporter are displayed along the right-hand border of each panel. As is seen from these autoradiographs, EAAT1 is expressed predominantly in brain, heart and muscle, to a lesser extent in placenta and lung, weakly in liver, and at levels below the ability of this assay to detect in kidney and the pancreas (if at all). EAAT2 is expressed in brain, and to a lesser extent in placenta; expression was not detected in any other tissue tested. EAAT3 is expressed predominantly in the kidney, but significant expression was also detected in brain, placenta, and lung. ASCT1 is expressed in all tissues tested as at least one of three differently-sized transcripts, possibly corresponding to differential RNA processing during expression of this transporter (which result might be due in the alternative to the utilization of alternative polyadenylation sites found in the 3' untranslated region). These results demonstrate that the amino acid transporters disclosed herein are encoded by separate and distinct, albeit related, genes and that each transporter has a unique pattern of tissue-specific expression.

FIG. 10 shows the distribution of these amino acid transporter transcripts in different human brain regions. Varying expression levels were found for each of the amino acid transporters in all brain regions examined. These results support the conclusion that the amino acid transporters of the invention may play an important role in normal brain function, and that disruption of amino acid transport by these transporter may be important determinants in organic brain dysfunction, as a result of ischemia or anoxia.

EXAMPLE 8

Construction of Vaccinia Virus-Recombinant Expression Constructs for Functional Expression of Amino Acid Transporters Using an alternative approach, the amino acid transporter proteins of the invention are expressed in human HeLa (vulval adenocarcinoma) cells via a vaccinia virus-based construct. In these experiments, each of the amino acid transporter cDNAs of the invention are excised from their respective pOTV-containing constructs and subcloned into a modified pBluescript (Strategene) vector wherein each of the amino acid transporter cDNAs described above is under the control of a bacteriophage T7 RNA polymerase promoter (as is described in Blakely et al. 1991, Anal. Biochem. 194:302–308), termed pT7-AAT constructs. HeLa cells are first infected with a recombinant vaccinia virus, VTF-7, that expresses T7 RNA polymerase. Cells are incubated with virus at a concentration of about 10 plaque-forming unit/cell in serum-free Dulbecco's modified Eagle's medium at 37° C. for 30 min., and then the cells were transfected with each of the amino acid transporter constructs described above (i.e. the pT7-AAT constructs) using a lipofectin-mediated (Bethesda Research Labs, Gaithersburg, Md.) transfection protocol (see Felgner et al., 1987, Proc. Natl. Acad. Sci. USA 84:7413–7417). Cells are then incubated for 12–24 h before being assayed for amino acid transporter expression as described in Example 5.

EXAMPLE 9

Construction of Fusion Proteins-Recombinant Expression Constructs for Expression of Immunologically-Active Epitopes of Amino Acid Transporters The amino acid transporter proteins of the invention are expressed as fusion proteins in bacteria to produce immunologically-active epitopes. In these experiments, each of the amino acid transporter cDNAs of the invention are excised from their respective pOTV-containing constructs and subcloned into a pGEX-2T construct (Pharmacia, Piscataway, N.J.) whereby the coding sequences of the amino acid transporter cDNAs are translationally in-frame with sequences encoding glutathione-S-transferase (described in Arriza et al., 1992, J. Neurosci. 12: 4045–4055), termed pGST-AAT constructs. After introduction of the pGST-AAT constructs into bacterial cells (*E. coli*, strain D5α) using conventional techniques (see Sambrook et al., ibid.), fusion protein expression is induced with isopropyl-1-thio-β-D-galactopyranoside as described (Smith & Johnson, 1988, Gene 67: 31–40) and are purified using glutathione-Sepharose 4B (Pharmacia). Antibodies are then raised against each of the amino acid transporters of the invention by inoculation of rabbits with 300–500 μg of purified fusion protein in Freund's adjuvant (Grand Island Biological Co., Grand Island, N.Y.), said inoculation repeated approximately every 4 weeks. Sera are immunoaffinity-purified on columns of Affi-Gel 15 derivatized with purified fusion protein. After salt elution, such antibodies are neutralized, stabilized with bovine serum albumin at a final concentration of 1 mg/mL, dialyzed against PBS and assayed by immunoblotting using conventional techniques (Harlow & Lane, 1988, *Antibodies: A Laboratory Manual*, Cold Spring Harbor Laboratory Press, Cold Spring Harbor, N.Y.).

It should be understood that the foregoing disclosure emphasizes certain specific embodiments of the invention and that all modifications or alternatives equivalent thereto are within the spirit and scope of the invention as set forth in the appended claims.

TABLE I

| Amino Acid (1 mM)* | ASCT1 RNA-injected Oocytes** | Water-injected Oocytes** |
|---|---|---|
| Alanine | 18 ± 2 | 0.6 ± 0.1 |
| Serine | 20 ± 5.1 | 0.4 ± 0.1 |
| Cysteine | 19.2 ± 5.9 | 1.0 ± 0.3 |

*n = 5;
**pmol/min per oocyte:

TABLE II

| Amino Acid* | $K_m$ (μM) | $I_{max}$** |
|---|---|---|
| Alanine | 71 ± 14 | (1.0) |
| Serine | 88 ± 11 | 1.2 ± 0.08 |
| Cysteine | 29 ± 6 | 1.0 ± 0.04 |
| Threonine | 137 ± 19 | 1.4 ± 0.03 |
| Valine | 390 ± 8 | 0.6 ± 0.11 |

NOTE: data is expressed as the mean of at least 5 determinations ± standard error.
*All amino acids were the L-stereoisomer
**$I_{max}$ was determined by least squares fit to the equation: $I = I_{max} \times ([S]/(K_m + [S]))$ where $I_{max}$ is the maximal current and $K_m$ is the transport constant

What we claim is:

1. An isolated nucleic acid comprising a nucleotide sequence encoding a human excitatory amino acid transporter selected from the group consisting of the glutamate transporter EAAT2.

2. An isolated nucleic acid according to claim 1 wherein the nucleotide sequence of the nucleic acid comprises the sequence of the human excitatory amino acid transporter EAAT2 (SEQ ID No.:6).

3. A homogeneous composition of a mammalian excitatory amino acid transporter having a molecular weight of about 62.1 kilodaltons and an amino acid sequence comprising the amino acid sequence of the human excitatory amino acid transporter EAAT2 (SEQ ID No.:7).

4. A nucleic acid hybridization probe for the detection of mammalian excitatory amino acid transporter expression comprising the nucleotide sequence of claim 2.

5. A recombinant expression construct comprising a nucleic acid having a nucleotide sequence encoding a mammalian excitatory amino acid transporter, wherein the nucleotide sequence comprises the sequence of the human EAAT2 excitatory amino acid transporter (SEQ ID No.:6), and wherein the construct is capable of expressing the EAAT2 excitatory amino acid transporter in a transformed culture of eukaryotic or prokaryotic cells.

6. A cell culture transformed with the recombinant expression construct of claim 5, wherein the transformed cell culture expresses the EAAT2 excitatory amino acid transporter.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

CTGRGCRATG AARATGGCAG CCAGGGC Y TC ATACAGGGCT GTGCCRTCCA TGTTRATGGT   60

RGC   63

( 2 ) INFORMATION FOR SEQ ID NO:2:

( i ) SEQUENCE CHARACTERISTICS:
        ( A ) LENGTH: 1680 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: 5'UTR
        ( B ) LOCATION: 1..30

( i x ) FEATURE:
        ( A ) NAME/KEY: CDS
        ( B ) LOCATION: 31..1626

( i x ) FEATURE:
        ( A ) NAME/KEY: 3'UTR
        ( B ) LOCATION: 1626..1680

( x i ) SEQUENCE DESCRIPTION: SEQ ID NO:2:

```
CACCTCTAGC TCGGAGCGGC GTGTAGCGCC ATG GAG AAG AGC AAC GAG ACC AAC        54
                                 Met Glu Lys Ser Asn Glu Thr Asn
                                  1               5

GGC TAC CTT GAC AGC GCT CAG GCG GGG CCT GCG GCC GGG CCC GGA GCT        102
Gly Tyr Leu Asp Ser Ala Gln Ala Gly Pro Ala Ala Gly Pro Gly Ala
        10              15                  20

CCG GGG ACC GCG GCG GGA CGC GCA CGG CGT TGC GCG CGC TTC CTG CGG        150
Pro Gly Thr Ala Ala Gly Arg Ala Arg Arg Cys Ala Arg Phe Leu Arg
 25              30                  35                  40

CGC CAA GCG CTG GTG CTG CTC ACC GTG TCC GGG GTG CTG GCG GGC GCG        198
Arg Gln Ala Leu Val Leu Leu Thr Val Ser Gly Val Leu Ala Gly Ala
                45                  50                  55

GGC CTG GGC GCG GCG TTG CGC GGG CTC AGC CTG AGC CGC ACG CAG GTC        246
Gly Leu Gly Ala Ala Leu Arg Gly Leu Ser Leu Ser Arg Thr Gln Val
            60                  65                  70

ACC TAC CTG GCC TTC CCC GGC GAG ATG CTG CTC CGC ATG CTG CGC ATG        294
Thr Tyr Leu Ala Phe Pro Gly Glu Met Leu Leu Arg Met Leu Arg Met
        75                  80                  85

ATC ATC CTG CCG CTG GTG GTC TGC AGC CTG GTG TCG GGC GCC GCC TCG        342
Ile Ile Leu Pro Leu Val Val Cys Ser Leu Val Ser Gly Ala Ala Ser
        90                  95                 100

CTC GAT GCC AGC TGC CTC GGG CGT CTG GGC GGC ATC CGT GTC GCC TAC        390
Leu Asp Ala Ser Cys Leu Gly Arg Leu Gly Gly Ile Arg Val Ala Tyr
105                 110                 115                 120

TTT GGC CTC ACC ACA CTG AGT GCC TCG GCG CTC GCC GTG GCC TTG GCG        438
Phe Gly Leu Thr Thr Leu Ser Ala Ser Ala Leu Ala Val Ala Leu Ala
                125                 130                 135

TTC ATC ATC AAG CCA GGA TCC GGT GCG CAG ACC CTT CAG TCC AGC GAC        486
Phe Ile Ile Lys Pro Gly Ser Gly Ala Gln Thr Leu Gln Ser Ser Asp
                140                 145                 150

CTG GGG CTG GAG GAC TCG GGG CCT CCT CCT GTC CCC AAA GAG ACG GTG        534
Leu Gly Leu Glu Asp Ser Gly Pro Pro Pro Val Pro Lys Glu Thr Val
                155                 160                 165

GAC TCT TTC CTC GAC CTG GCC AGA AAC CTG TTT CCC TCC AAT CTT GTG        582
Asp Ser Phe Leu Asp Leu Ala Arg Asn Leu Phe Pro Ser Asn Leu Val
            170                 175                 180
```

```
GTT GCA GCT TTC CGT ACG TAT GCA ACC GAT TAT AAA GTC GTG ACC CAG     630
Val Ala Ala Phe Arg Thr Tyr Ala Thr Asp Tyr Lys Val Val Thr Gln
185                 190                 195                 200

AAC AGC AGC TCT GGA AAT GTA ACC CAT GAA AAG ATC CCC ATA GGC ACT     678
Asn Ser Ser Ser Gly Asn Val Thr His Glu Lys Ile Pro Ile Gly Thr
                    205                 210                 215

GAG ATA GAA GGG ATG AAC ATT TTA GGA TTG GTC CTG TTT GCT CTG GTG     726
Glu Ile Glu Gly Met Asn Ile Leu Gly Leu Val Leu Phe Ala Leu Val
                220                 225                 230

TTA GGA GTG GCC TTA AAG AAA CTA GGC TCC GAA GGA GAA GAC CTC ATC     774
Leu Gly Val Ala Leu Lys Lys Leu Gly Ser Glu Gly Glu Asp Leu Ile
            235                 240                 245

CGT TTC TTC AAT TCC CTC AAC GAG GCG ACG ATG GTG CTG GTG TCC TGG     822
Arg Phe Phe Asn Ser Leu Asn Glu Ala Thr Met Val Leu Val Ser Trp
        250                 255                 260

ATT ATG TGG TAC GTA CCT GTG GGC ATC ATG TTC CTT GTT GGA AGC AAG     870
Ile Met Trp Tyr Val Pro Val Gly Ile Met Phe Leu Val Gly Ser Lys
265                 270                 275                 280

ATC GTG GAA ATG AAA GAC ATC ATC GTG CTG GTG ACC AGC CTG GGG AAA     918
Ile Val Glu Met Lys Asp Ile Ile Val Leu Val Thr Ser Leu Gly Lys
                285                 290                 295

TAC ATC TTC GCA TCT ATA TTG GGC CAT GTT ATT CAT GGA GGA ATT GTT     966
Tyr Ile Phe Ala Ser Ile Leu Gly His Val Ile His Gly Gly Ile Val
                300                 305                 310

CTG CCA CTT ATT TAT TTT GTT TTC ACA CGA AAA AAC CCA TTC AGA TTC    1014
Leu Pro Leu Ile Tyr Phe Val Phe Thr Arg Lys Asn Pro Phe Arg Phe
            315                 320                 325

CTC CTG GGC CTC CTC GCC CCA TTT GCG ACA GCA TTT GCT ACC TGC TCC    1062
Leu Leu Gly Leu Leu Ala Pro Phe Ala Thr Ala Phe Ala Thr Cys Ser
        330                 335                 340

AGC TCA GCG ACC CTT CCC TCT ATG ATG AAG TGC ATT GAA GAG AAC AAT    1110
Ser Ser Ala Thr Leu Pro Ser Met Met Lys Cys Ile Glu Glu Asn Asn
345                 350                 355                 360

GGT GTG GAC AAG AGG ATC AGC AGG TTT ATT CTC CCC ATC GGG GCC ACC    1158
Gly Val Asp Lys Arg Ile Ser Arg Phe Ile Leu Pro Ile Gly Ala Thr
                365                 370                 375

GTG AAC ATG GAC GGA GCA GCC ATC TTC CAG TGT GTG GCC GCG GTG TTC    1206
Val Asn Met Asp Gly Ala Ala Ile Phe Gln Cys Val Ala Ala Val Phe
                380                 385                 390

ATT GCG CAA CTC AAC AAC ATA GAG CTC AAC GCA GGA CAG ATT TTC ACC    1254
Ile Ala Gln Leu Asn Asn Ile Glu Leu Asn Ala Gly Gln Ile Phe Thr
            395                 400                 405

ATT CTA GTG ACT GCC ACA GCG TCC AGT GTT GGA GCA GCA GGC GTG CCA    1302
Ile Leu Val Thr Ala Thr Ala Ser Ser Val Gly Ala Ala Gly Val Pro
        410                 415                 420

GCT GGA GGG GTC CTC ACC ATT GCC ATT ATC CTG GAG GCC ATT GGG CTG    1350
Ala Gly Gly Val Leu Thr Ile Ala Ile Ile Leu Glu Ala Ile Gly Leu
425                 430                 435                 440

CCT ACT CAT GAC CTG CCT CTG ATC CTG GCT GTG GAC TGG ATT GTG GAC    1398
Pro Thr His Asp Leu Pro Leu Ile Leu Ala Val Asp Trp Ile Val Asp
                445                 450                 455

CGG ACC ACC ACG GTG GTG AAT GTG GAG GGG GAT GCC CTG GGT GCA GGC    1446
Arg Thr Thr Thr Val Val Asn Val Glu Gly Asp Ala Leu Gly Ala Gly
                460                 465                 470

ATT CTC CAC CAC CTG AAT CAG AAG GCA ACA AAG AAA GGC GAG CAG GAA    1494
Ile Leu His His Leu Asn Gln Lys Ala Thr Lys Lys Gly Glu Gln Glu
            475                 480                 485

CTT GCT GAG GTG AAA GTG GAA GCC ATC CCC AAC TGC AAG TCT GAG GAG    1542
Leu Ala Glu Val Lys Val Glu Ala Ile Pro Asn Cys Lys Ser Glu Glu
490                 495                 500
```

```
GAG ACA TCG CCC CTG GTG ACA CAC CAG AAC CCC GCT GGC CCC GTG GCC        1590
Glu Thr Ser Pro Leu Val Thr His Gln Asn Pro Ala Gly Pro Val Ala
505                 510                 515                 520

AGT GCC CCA GAA CTG GAA TCC AAG GAG TCG GTT CTG TGATGGGGCT              1636
Ser Ala Pro Glu Leu Glu Ser Lys Glu Ser Val Leu
                525                 530

GGGCTTTGGG CTTGCCTGCC AGCAGTGATG TCCCACCCTG TTCA                        1680
```

( 2 ) INFORMATION FOR SEQ ID NO:3:

( i ) SEQUENCE CHARACTERISTICS:
        ( A ) LENGTH: 532 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Glu Lys Ser Asn Glu Thr Asn Gly Tyr Leu Asp Ser Ala Gln Ala
 1               5                  10                  15

Gly Pro Ala Ala Gly Pro Gly Ala Pro Gly Thr Ala Ala Gly Arg Ala
                20                  25                  30

Arg Arg Cys Ala Arg Phe Leu Arg Arg Gln Ala Leu Val Leu Leu Thr
            35                  40                  45

Val Ser Gly Val Leu Ala Gly Ala Gly Leu Gly Ala Ala Leu Arg Gly
        50                  55                  60

Leu Ser Leu Ser Arg Thr Gln Val Thr Tyr Leu Ala Phe Pro Gly Glu
65                  70                  75                  80

Met Leu Leu Arg Met Leu Arg Met Ile Ile Leu Pro Leu Val Val Cys
                85                  90                  95

Ser Leu Val Ser Gly Ala Ala Ser Leu Asp Ala Ser Cys Leu Gly Arg
                100                 105                 110

Leu Gly Gly Ile Arg Val Ala Tyr Phe Gly Leu Thr Thr Leu Ser Ala
            115                 120                 125

Ser Ala Leu Ala Val Ala Leu Ala Phe Ile Ile Lys Pro Gly Ser Gly
        130                 135                 140

Ala Gln Thr Leu Gln Ser Ser Asp Leu Gly Leu Glu Asp Ser Gly Pro
145                 150                 155                 160

Pro Pro Val Pro Lys Glu Thr Val Asp Ser Phe Leu Asp Leu Ala Arg
                165                 170                 175

Asn Leu Phe Pro Ser Asn Leu Val Val Ala Ala Phe Arg Thr Tyr Ala
            180                 185                 190

Thr Asp Tyr Lys Val Val Thr Gln Asn Ser Ser Ser Gly Asn Val Thr
        195                 200                 205

His Glu Lys Ile Pro Ile Gly Thr Glu Ile Glu Gly Met Asn Ile Leu
210                 215                 220

Gly Leu Val Leu Phe Ala Leu Val Leu Gly Val Ala Leu Lys Lys Leu
225                 230                 235                 240

Gly Ser Glu Gly Glu Asp Leu Ile Arg Phe Phe Asn Ser Leu Asn Glu
                245                 250                 255

Ala Thr Met Val Leu Val Ser Trp Ile Met Trp Tyr Val Pro Val Gly
            260                 265                 270

Ile Met Phe Leu Val Gly Ser Lys Ile Val Glu Met Lys Asp Ile Ile
        275                 280                 285

Val Leu Val Thr Ser Leu Gly Lys Tyr Ile Phe Ala Ser Ile Leu Gly
290                 295                 300
```

```
His  Val  Ile  His  Gly  Gly  Ile  Val  Leu  Pro  Leu  Ile  Tyr  Phe  Val  Phe
305                      310                      315                      320

Thr  Arg  Lys  Asn  Pro  Phe  Arg  Phe  Leu  Leu  Gly  Leu  Leu  Ala  Pro  Phe
                    325                      330                      335

Ala  Thr  Ala  Phe  Ala  Thr  Cys  Ser  Ser  Ser  Ala  Thr  Leu  Pro  Ser  Met
               340                      345                      350

Met  Lys  Cys  Ile  Glu  Glu  Asn  Asn  Gly  Val  Asp  Lys  Arg  Ile  Ser  Arg
          355                      360                      365

Phe  Ile  Leu  Pro  Ile  Gly  Ala  Thr  Val  Asn  Met  Asp  Gly  Ala  Ala  Ile
     370                      375                      380

Phe  Gln  Cys  Val  Ala  Ala  Val  Phe  Ile  Ala  Gln  Leu  Asn  Asn  Ile  Glu
385                      390                      395                      400

Leu  Asn  Ala  Gly  Gln  Ile  Phe  Thr  Ile  Leu  Val  Thr  Ala  Thr  Ala  Ser
                    405                      410                      415

Ser  Val  Gly  Ala  Ala  Gly  Val  Pro  Ala  Gly  Gly  Val  Leu  Thr  Ile  Ala
               420                      425                      430.

Ile  Ile  Leu  Glu  Ala  Ile  Gly  Leu  Pro  Thr  His  Asp  Leu  Pro  Leu  Ile
          435                      440                      445

Leu  Ala  Val  Asp  Trp  Ile  Val  Asp  Arg  Thr  Thr  Thr  Val  Val  Asn  Val
450                      455                      460

Glu  Gly  Asp  Ala  Leu  Gly  Ala  Gly  Ile  Leu  His  His  Leu  Asn  Gln  Lys
465                 470                      475                      480

Ala  Thr  Lys  Lys  Gly  Glu  Gln  Glu  Leu  Ala  Glu  Val  Lys  Val  Glu  Ala
               485                      490                      495

Ile  Pro  Asn  Cys  Lys  Ser  Glu  Glu  Thr  Ser  Pro  Leu  Val  Thr  His
               500                      505                      510

Gln  Asn  Pro  Ala  Gly  Pro  Val  Ala  Ser  Ala  Pro  Glu  Leu  Glu  Ser  Lys
               515                      520                      525

Glu  Ser  Val  Leu
530
```

( 2 ) INFORMATION FOR SEQ ID NO:4:

( i ) SEQUENCE CHARACTERISTICS:
        ( A ) LENGTH: 1680 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: 5'UTR
        ( B ) LOCATION: 1..30

( i x ) FEATURE:
        ( A ) NAME/KEY: CDS
        ( B ) LOCATION: 31..1656

( i x ) FEATURE:
        ( A ) NAME/KEY: 3'UTR
        ( B ) LOCATION: 1657..1680

( x i ) SEQUENCE DESCRIPTION: SEQ ID NO:4:

```
AAAGAAGAGA  CCCTCCTAGA  AAAGTAAAAT  ATG  ACT  AAA  AGC  AAT  GGA  GAA  GAG         54
                                   Met  Thr  Lys  Ser  Asn  Gly  Glu  Glu
                                    1                 5

CCC  AAG  ATG  GGG  GGC  AGG  ATG  GAG  AGA  TTC  CAG  CAG  GGA  GTC  CGT  AAA   102
Pro  Lys  Met  Gly  Gly  Arg  Met  Glu  Arg  Phe  Gln  Gln  Gly  Val  Arg  Lys
         10                        15                       20

CGC  ACA  CTT  TTG  GCC  AAG  AAG  AAA  GTG  CAG  AAC  ATT  ACA  AAG  GAG  GTT   150
```

|     |     |     |     |     |     |     |     |     |     |     |     |     |     |     |     |
|---|---|---|---|---|---|---|---|---|---|---|---|---|---|---|---|
| Arg | Thr | Leu | Leu | Ala | Lys | Lys | Lys | Val | Gln | Asn | Ile | Thr | Lys | Glu | Val |
| 25  |     |     |     |     | 30  |     |     |     |     | 35  |     |     |     |     | 40  |

```
GTT AAA AGT TAC CTG TTT CGG AAT GCT TTT GTG CTG CTC ACA GTC ACC            198
Val Lys Ser Tyr Leu Phe Arg Asn Ala Phe Val Leu Leu Thr Val Thr
            45              50                  55

GCT GTC ATT GTG GGT ACA ATC CTT GGA TTT ACC CTC CGA CCA TAC AGA            246
Ala Val Ile Val Gly Thr Ile Leu Gly Phe Thr Leu Arg Pro Tyr Arg
            60              65                  70

ATG AGC TAC CGG GAA GTC AAG TAC TTC TCC TTT CCT GGG GAA CTT CTG            294
Met Ser Tyr Arg Glu Val Lys Tyr Phe Ser Phe Pro Gly Glu Leu Leu
            75              80                  85

ATG AGG ATG TTA CAG ATG CTG GTC TTA CCA CTT ATC ATC TCC AGT CTT            342
Met Arg Met Leu Gln Met Leu Val Leu Pro Leu Ile Ile Ser Ser Leu
            90              95                  100

GTC ACA GGA ATG GCG GCG CTA GAT AGT AAG GCA TCA GGG AAG TGG GAA            390
Val Thr Gly Met Ala Ala Leu Asp Ser Lys Ala Ser Gly Lys Trp Glu
105             110             115                 120

TGC GGA GCT GTA GTC TAT TAT ATG ACT ACC ACC ATC ATT GCT GTG GTG            438
Cys Gly Ala Val Val Tyr Tyr Met Thr Thr Thr Ile Ile Ala Val Val
            125             130                 135

ATT GGC ATA ATC ATT GTC ATC ATC ATC CAT CCT GGG AAG GGC ACA AAG            486
Ile Gly Ile Ile Ile Val Ile Ile Ile His Pro Gly Lys Gly Thr Lys
            140             145                 150

GAA AAC ATG CAC AGA GAA GGC AAA ATT GTA CGA GTG ACA GCT GCA GAT            534
Glu Asn Met His Arg Glu Gly Lys Ile Val Arg Val Thr Ala Ala Asp
            155             160                 165

GCC TTC CTG GAC TTG ATC AGG AAC ATG TTA AAT CCA AAT CTG GTA GAA            582
Ala Phe Leu Asp Leu Ile Arg Asn Met Leu Asn Pro Asn Leu Val Glu
170             175             180

GCC TGC TTT AAA CAG TTT AAA ACC AAC TAT GAG AAG AGA AGC TTT AAA            630
Ala Cys Phe Lys Gln Phe Lys Thr Asn Tyr Glu Lys Arg Ser Phe Lys
185             190             195                 200

GTG CCC ATC CAG GCC AAC GAA ACG CTT GTG GGT GCT GTG ATA AAC AAT            678
Val Pro Ile Gln Ala Asn Glu Thr Leu Val Gly Ala Val Ile Asn Asn
            205             210                 215

GTG TCT GAG GCC ATG GAG ACT CTT ACC CGA ATC ACA GAG GAG CTG GTC            726
Val Ser Glu Ala Met Glu Thr Leu Thr Arg Ile Thr Glu Glu Leu Val
            220             225                 230

CCA GTT CCA GGA TCT GTG AAT GGA GTC AAT GCC CTG GGT CTA GTT GTC            774
Pro Val Pro Gly Ser Val Asn Gly Val Asn Ala Leu Gly Leu Val Val
            235             240                 245

TTC TCC ATG TGC TTC GGT TTT GTG ATT GGA AAC ATG AAG GAA CAG GGG            822
Phe Ser Met Cys Phe Gly Phe Val Ile Gly Asn Met Lys Glu Gln Gly
            250             255                 260

CAG GCC CTG AGA GAG TTC TTT GAT TCT CTT AAC GAA GCC ATC ATG AGA            870
Gln Ala Leu Arg Glu Phe Phe Asp Ser Leu Asn Glu Ala Ile Met Arg
265             270             275                 280

CTG GTA GCA GTA ATA ATG TGG TAT GCC CCC GTG GGT ATT CTC TTC CTG            918
Leu Val Ala Val Ile Met Trp Tyr Ala Pro Val Gly Ile Leu Phe Leu
            285             290                 295

ATT GCT GGG AAG ATT GTG GAG ATG GAA GAC ATG GGT GTG ATT GGG GGG            966
Ile Ala Gly Lys Ile Val Glu Met Glu Asp Met Gly Val Ile Gly Gly
            300             305                 310

CAG CTT GCC ATG TAC ACC GTG ACT GTC ATT GTT GGC TTA CTC ATT CAC            1014
Gln Leu Ala Met Tyr Thr Val Thr Val Ile Val Gly Leu Leu Ile His
            315             320                 325

GCA GTC ATC GTC TTG CCA CTC CTC TAC TTC TTG GTA ACA CGG AAA AAC            1062
Ala Val Ile Val Leu Pro Leu Leu Tyr Phe Leu Val Thr Arg Lys Asn
330             335             340

CCT TGG GTT TTT ATT GGA GGG TTG CTG CAA GCA CTC ATC ACC GCT CTG            1110
```

| | | | | | | | | | | | | | | | | |
|---|---|---|---|---|---|---|---|---|---|---|---|---|---|---|---|---|
| Pro<br>345 | Trp | Val | Phe | Ile | Gly<br>350 | Gly | Leu | Leu | Gln | Ala<br>355 | Leu | Ile | Thr | Ala | Leu<br>360 | |
| GGG<br>Gly | ACC<br>Thr | TCT<br>Ser | TCA<br>Ser | AGT<br>Ser<br>365 | TCT<br>Ser | GCC<br>Ala | ACC<br>Thr | CTA<br>Leu | CCC<br>Pro<br>370 | ATC<br>Ile | ACC<br>Thr | TTC<br>Phe | AAG<br>Lys | TGC<br>Cys<br>375 | CTG<br>Leu | 1158 |
| GAA<br>Glu | GAG<br>Glu | AAC<br>Asn | AAT<br>Asn<br>380 | GGC<br>Gly | GTG<br>Val | GAC<br>Asp | AAG<br>Lys | CGC<br>Arg<br>385 | GTC<br>Val | ACC<br>Thr | AGA<br>Arg | TTC<br>Phe | GTG<br>Val<br>390 | CTC<br>Leu | CCC<br>Pro | 1206 |
| GTA<br>Val | GGA<br>Gly | GCC<br>Ala<br>395 | ACC<br>Thr | ATT<br>Ile | AAC<br>Asn | ATG<br>Met | GAT<br>Asp<br>400 | GGG<br>Gly | ACT<br>Thr | GCC<br>Ala | CTC<br>Leu | TAT<br>Tyr<br>405 | GAG<br>Glu | GCT<br>Ala | TTG<br>Leu | 1254 |
| GCT<br>Ala | GCC<br>Ala<br>410 | ATT<br>Ile | TTC<br>Phe | ATT<br>Ile | GCT<br>Ala | CAA<br>Gln<br>415 | GTT<br>Val | AAC<br>Asn | AAC<br>Asn | TTT<br>Phe | GAA<br>Glu<br>420 | CTG<br>Leu | AAC<br>Asn | TTC<br>Phe | GGA<br>Gly | 1302 |
| CAA<br>Gln<br>425 | ATT<br>Ile | ATT<br>Ile | ACA<br>Thr | ATC<br>Ile<br>430 | AGC<br>Ser | ATC<br>Ile | ACA<br>Thr | GCC<br>Ala | ACA<br>Thr<br>435 | GCT<br>Ala | GCC<br>Ala | AGT<br>Ser | ATT<br>Ile | GGG<br>Gly<br>440 | GCA<br>Ala | 1350 |
| GCT<br>Ala | GGA<br>Gly | ATT<br>Ile | CCT<br>Pro | CAG<br>Gln<br>445 | GCG<br>Ala | GGC<br>Gly | CTG<br>Leu | GTC<br>Val | ACT<br>Thr<br>450 | ATG<br>Met | GTC<br>Val | ATT<br>Ile | GTG<br>Val | CTG<br>Leu<br>455 | ACA<br>Thr | 1398 |
| TCT<br>Ser | GTC<br>Val | GGC<br>Gly | CTG<br>Leu<br>460 | CCC<br>Pro | ACT<br>Thr | GAC<br>Asp | GAC<br>Asp | ATC<br>Ile<br>465 | ACG<br>Thr | CTC<br>Leu | ATC<br>Ile | ATC<br>Ile | GCG<br>Ala<br>470 | GTG<br>Val | GAC<br>Asp | 1446 |
| TGG<br>Trp | TTC<br>Phe<br>475 | TTG<br>Leu | GAT<br>Asp | CGC<br>Arg | CTC<br>Leu | CGG<br>Arg<br>480 | ACC<br>Thr | ACC<br>Thr | ACC<br>Thr | AAC<br>Asn | GTA<br>Val<br>485 | CTG<br>Leu | GGA<br>Gly | GAC<br>Asp | TCC<br>Ser | 1494 |
| CTG<br>Leu | GGA<br>Gly<br>490 | GCT<br>Ala | GGG<br>Gly | ATT<br>Ile | GTG<br>Val | GAG<br>Glu<br>495 | CAC<br>His | TTG<br>Leu | TCA<br>Ser | CGA<br>Arg | CAT<br>His<br>500 | GAA<br>Glu | CTG<br>Leu | AAG<br>Lys | AAC<br>Asn | 1542 |
| AGA<br>Arg<br>505 | GAT<br>Asp | GTT<br>Val | GAA<br>Glu | ATG<br>Met<br>510 | GGT<br>Gly | AAC<br>Asn | TCA<br>Ser | GTG<br>Val | ATT<br>Ile<br>515 | GAA<br>Glu | GAG<br>Glu | AAT<br>Asn | GAA<br>Glu | ATG<br>Met<br>520 | AAG<br>Lys | 1590 |
| AAA<br>Lys | CCA<br>Pro | TAT<br>Tyr | CAA<br>Gln | CTG<br>Leu<br>525 | ATT<br>Ile | GCA<br>Ala | CAG<br>Gln | GAC<br>Asp | AAT<br>Asn<br>530 | GAA<br>Glu | ACT<br>Thr | GAG<br>Glu | AAA<br>Lys | CCC<br>Pro<br>535 | ATC<br>Ile | 1638 |
| GAC<br>Asp | AGT<br>Ser | GAA<br>Glu | ACC<br>Thr | AAG<br>Lys | ATG<br>Met<br>540 | TAGACTAACA | | TAAAGAAACA | | CTTT | | | | | | 1680 |

(2) INFORMATION FOR SEQ ID NO:5:

(i) SEQUENCE CHARACTERISTICS:
        (A) LENGTH: 542 amino acids
        (B) TYPE: amino acid
        (D) TOPOLOGY: linear (ii) MOLECULE TYPE: protein (xi) SEQUENCE DESCRIPTION: SEQ ID NO:5:

| | | | | | | | | | | | | | | |
|---|---|---|---|---|---|---|---|---|---|---|---|---|---|---|
| Met<br>1 | Thr | Lys | Ser | Asn<br>5 | Gly | Glu | Glu | Pro | Lys<br>10 | Met | Gly | Gly | Arg | Met<br>15 | Glu |
| Arg | Phe | Gln | Gln<br>20 | Gly | Val | Arg | Lys | Arg<br>25 | Thr | Leu | Leu | Ala | Lys<br>30 | Lys | Lys |
| Val | Gln | Asn | Ile<br>35 | Thr | Lys | Glu | Val<br>40 | Val | Lys | Ser | Tyr | Leu<br>45 | Phe | Arg | Asn |
| Ala | Phe<br>50 | Val | Leu | Leu | Thr | Val<br>55 | Thr | Ala | Val | Ile | Val<br>60 | Gly | Thr | Ile | Leu |
| Gly<br>65 | Phe | Thr | Leu | Arg | Pro<br>70 | Tyr | Arg | Met | Ser | Tyr<br>75 | Arg | Glu | Val | Lys | Tyr<br>80 |
| Phe | Ser | Phe | Pro | Gly<br>85 | Glu | Leu | Leu | Met | Arg<br>90 | Met | Leu | Gln | Met | Leu<br>95 | Val |

Leu Pro Leu Ile Ile Ser Ser Leu Val Thr Gly Met Ala Ala Leu Asp
                    100                     105                     110

Ser Lys Ala Ser Gly Lys Trp Glu Cys Gly Ala Val Val Tyr Tyr Met
            115                     120                     125

Thr Thr Thr Ile Ile Ala Val Val Ile Gly Ile Ile Ile Val Ile Ile
        130                     135                     140

Ile His Pro Gly Lys Gly Thr Lys Glu Asn Met His Arg Glu Gly Lys
145                     150                     155                     160

Ile Val Arg Val Thr Ala Ala Asp Ala Phe Leu Asp Leu Ile Arg Asn
                    165                     170                     175

Met Leu Asn Pro Asn Leu Val Glu Ala Cys Phe Lys Gln Phe Lys Thr
                180                     185                     190

Asn Tyr Glu Lys Arg Ser Phe Lys Val Pro Ile Gln Ala Asn Glu Thr
            195                     200                     205

Leu Val Gly Ala Val Ile Asn Asn Val Ser Glu Ala Met Glu Thr Leu
        210                     215                     220

Thr Arg Ile Thr Glu Glu Leu Val Pro Val Pro Gly Ser Val Asn Gly
225                     230                     235                     240

Val Asn Ala Leu Gly Leu Val Val Phe Ser Met Cys Phe Gly Phe Val
                    245                     250                     255

Ile Gly Asn Met Lys Glu Gln Gly Gln Ala Leu Arg Glu Phe Phe Asp
                260                     265                     270

Ser Leu Asn Glu Ala Ile Met Arg Leu Val Ala Val Ile Met Trp Tyr
            275                     280                     285

Ala Pro Val Gly Ile Leu Phe Leu Ile Ala Gly Lys Ile Val Glu Met
        290                     295                     300

Glu Asp Met Gly Val Ile Gly Gly Gln Leu Ala Met Tyr Thr Val Thr
305                     310                     315                     320

Val Ile Val Gly Leu Leu Ile His Ala Val Ile Val Leu Pro Leu Leu
                    325                     330                     335

Tyr Phe Leu Val Thr Arg Lys Asn Pro Trp Val Phe Ile Gly Gly Leu
                340                     345                     350

Leu Gln Ala Leu Ile Thr Ala Leu Gly Thr Ser Ser Ser Ser Ala Thr
            355                     360                     365

Leu Pro Ile Thr Phe Lys Cys Leu Glu Glu Asn Asn Gly Val Asp Lys
        370                     375                     380

Arg Val Thr Arg Phe Val Leu Pro Val Gly Ala Thr Ile Asn Met Asp
385                     390                     395                     400

Gly Thr Ala Leu Tyr Glu Ala Leu Ala Ala Ile Phe Ile Ala Gln Val
                    405                     410                     415

Asn Asn Phe Glu Leu Asn Phe Gly Gln Ile Ile Thr Ile Ser Ile Thr
                420                     425                     430

Ala Thr Ala Ala Ser Ile Gly Ala Ala Gly Ile Pro Gln Ala Gly Leu
            435                     440                     445

Val Thr Met Val Ile Val Leu Thr Ser Val Gly Leu Pro Thr Asp Asp
        450                     455                     460

Ile Thr Leu Ile Ile Ala Val Asp Trp Phe Leu Asp Arg Leu Arg Thr
465                     470                     475                     480

Thr Thr Asn Val Leu Gly Asp Ser Leu Gly Ala Gly Ile Val Glu His
                    485                     490                     495

Leu Ser Arg His Glu Leu Lys Asn Arg Asp Val Glu Met Gly Asn Ser
                500                     505                     510

Val Ile Glu Glu Asn Glu Met Lys Lys Pro Tyr Gln Leu Ile Ala Gln

|  | 515 |  |  |  | 520 |  |  |  |  | 525 |  |
|---|---|---|---|---|---|---|---|---|---|---|---|
| Asp | Asn | Glu | Thr | Glu | Lys | Pro | Ile | Asp | Ser | Glu | Thr | Lys | Met |
| 530 |  |  |  |  | 535 |  |  |  | 540 |  |  |

( 2 ) INFORMATION FOR SEQ ID NO:6:

( i ) SEQUENCE CHARACTERISTICS:
        ( A ) LENGTH: 1800 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: 5'UTR
        ( B ) LOCATION: 1..33

( i x ) FEATURE:
        ( A ) NAME/KEY: CDS
        ( B ) LOCATION: 34..1755

( i x ) FEATURE:
        ( A ) NAME/KEY: 3'UTR
        ( B ) LOCATION: 1756..1800

( x i ) SEQUENCE DESCRIPTION: SEQ ID NO:6:

| GATAGTGCTG | AAGAGGAGGG | GCGTTCCCAG | ACC | ATG | GCA | TCT | ACG | GAA | GGT | GCC | 54 |
|---|---|---|---|---|---|---|---|---|---|---|---|
|  |  |  |  | Met | Ala | Ser | Thr | Glu | Gly | Ala |  |
|  |  |  |  | 1 |  |  |  | 5 |  |  |  |

| AAC | AAT | ATG | CCC | AAG | CAG | GTG | GAA | GTG | CGA | ATG | CCA | GAC | AGT | CAT | CTT | 102 |
|---|---|---|---|---|---|---|---|---|---|---|---|---|---|---|---|---|
| Asn | Asn | Met | Pro | Lys | Gln | Val | Glu | Val | Arg | Met | Pro | Asp | Ser | His | Leu |  |
|  |  | 10 |  |  |  |  | 15 |  |  |  |  | 20 |  |  |  |  |

| GGC | TCA | GAG | GAA | CCC | AAG | CAC | CGG | CAC | CTG | GGC | CTG | CGC | CTG | TGT | GAC | 150 |
|---|---|---|---|---|---|---|---|---|---|---|---|---|---|---|---|---|
| Gly | Ser | Glu | Glu | Pro | Lys | His | Arg | His | Leu | Gly | Leu | Arg | Leu | Cys | Asp |  |
|  | 25 |  |  |  |  | 30 |  |  |  |  | 35 |  |  |  |  |  |

| AAG | CTG | GGG | AAG | AAT | CTG | CTC | ACC | CTG | ACG | GTG | TTT | GGT | GTC | ATC | 198 |
|---|---|---|---|---|---|---|---|---|---|---|---|---|---|---|---|
| Lys | Leu | Gly | Lys | Asn | Leu | Leu | Leu | Thr | Leu | Thr | Val | Phe | Gly | Val | Ile |
| 40 |  |  |  |  | 45 |  |  |  |  | 50 |  |  |  | 55 |  |

| CTG | GGA | GCA | GTG | TGT | GGA | GGG | CTT | CTT | CGC | TTG | GCA | TCT | CCC | ATC | CAC | 246 |
|---|---|---|---|---|---|---|---|---|---|---|---|---|---|---|---|---|
| Leu | Gly | Ala | Val | Cys | Gly | Gly | Leu | Leu | Arg | Leu | Ala | Ser | Pro | Ile | His |  |
|  |  |  | 60 |  |  |  |  | 65 |  |  |  |  | 70 |  |  |  |

| CCT | GAT | GTG | GTT | ATG | TTA | ATA | GCC | TTC | CCA | GGG | GAT | ATA | CTC | ATG | AGG | 294 |
|---|---|---|---|---|---|---|---|---|---|---|---|---|---|---|---|---|
| Pro | Asp | Val | Val | Met | Leu | Ile | Ala | Phe | Pro | Gly | Asp | Ile | Leu | Met | Arg |  |
|  |  |  | 75 |  |  |  |  | 80 |  |  |  |  | 85 |  |  |  |

| ATG | CTA | AAA | ATG | CTC | ATT | CTG | GGT | CTA | ATC | ATC | TCC | AGC | TTA | ATC | ACA | 342 |
|---|---|---|---|---|---|---|---|---|---|---|---|---|---|---|---|---|
| Met | Leu | Lys | Met | Leu | Ile | Leu | Gly | Leu | Ile | Ile | Ser | Ser | Leu | Ile | Thr |  |
|  |  | 90 |  |  |  |  | 95 |  |  |  |  | 100 |  |  |  |  |

| GGG | TTG | TCA | GGC | CTG | GAT | GCT | AAG | GCT | AGT | GGC | CGC | TTG | GGC | ACG | AGA | 390 |
|---|---|---|---|---|---|---|---|---|---|---|---|---|---|---|---|---|
| Gly | Leu | Ser | Gly | Leu | Asp | Ala | Lys | Ala | Ser | Gly | Arg | Leu | Gly | Thr | Arg |  |
|  | 105 |  |  |  |  | 110 |  |  |  |  | 115 |  |  |  |  |  |

| GCC | ATG | GTG | TAT | TAC | ATG | TCC | ACG | ACC | ATC | ATT | GCT | GCA | GTA | CTG | GGG | 438 |
|---|---|---|---|---|---|---|---|---|---|---|---|---|---|---|---|---|
| Ala | Met | Val | Tyr | Tyr | Met | Ser | Thr | Thr | Ile | Ile | Ala | Ala | Val | Leu | Gly |  |
| 120 |  |  |  |  | 125 |  |  |  |  | 130 |  |  |  |  | 135 |  |

| GTC | ATT | CTG | GTC | TTG | GCT | ATC | CAT | CCA | GGC | AAT | CCC | AAG | CTC | AAG | AAG | 486 |
|---|---|---|---|---|---|---|---|---|---|---|---|---|---|---|---|---|
| Val | Ile | Leu | Val | Leu | Ala | Ile | His | Pro | Gly | Asn | Pro | Lys | Leu | Lys | Lys |  |
|  |  |  |  | 140 |  |  |  |  | 145 |  |  |  |  | 150 |  |  |

| CAG | CTG | GGG | CCT | GGG | AAG | AAG | AAT | GAT | GAA | GTG | TCC | AGC | CTG | GAT | GCC | 534 |
|---|---|---|---|---|---|---|---|---|---|---|---|---|---|---|---|---|
| Gln | Leu | Gly | Pro | Gly | Lys | Lys | Asn | Asp | Glu | Val | Ser | Ser | Leu | Asp | Ala |  |
|  |  |  | 155 |  |  |  |  | 160 |  |  |  |  | 165 |  |  |  |

| TTC | CTG | GAC | CTT | ATT | CGA | AAT | CTC | TTC | CCT | GAA | AAC | CTT | GTC | CAA | GCC | 582 |
|---|---|---|---|---|---|---|---|---|---|---|---|---|---|---|---|---|
| Phe | Leu | Asp | Leu | Ile | Arg | Asn | Leu | Phe | Pro | Glu | Asn | Leu | Val | Gln | Ala |  |
|  |  | 170 |  |  |  |  | 175 |  |  |  |  | 180 |  |  |  |  |

| TGC | TTT | CAA | CAG | ATT | CAA | ACA | GTG | ACG | AAG | AAA | GTC | CTG | GTT | GCA | CCA | 630 |
|---|---|---|---|---|---|---|---|---|---|---|---|---|---|---|---|---|

```
Cys Phe Gln Gln Ile Gln Thr Val Thr Lys Lys Val Leu Val Ala Pro
185             190                 195

CCG CCA GAC GAG GAG GCC AAC GCA ACC AGC GCT GAA GTC TCT CTG TTG    678
Pro Pro Asp Glu Glu Ala Asn Ala Thr Ser Ala Glu Val Ser Leu Leu
200             205                 210             215

AAC GAG ACT GTG ACT GAG GTG CCG GAG GAG ACT AAG ATG GTT ATC AAG    726
Asn Glu Thr Val Thr Glu Val Pro Glu Glu Thr Lys Met Val Ile Lys
                220                 225                 230

AAG GGC CTG GAG TTC AAG GAT GGG ATG AAC GTC TTA GGT CTG ATA GGG    774
Lys Gly Leu Glu Phe Lys Asp Gly Met Asn Val Leu Gly Leu Ile Gly
            235                 240                 245

TTT TTC ATT GCT TTT GGC ATC GCT ATG GGG AAG ATG GGA GAT CAG GCC    822
Phe Phe Ile Ala Phe Gly Ile Ala Met Gly Lys Met Gly Asp Gln Ala
        250                 255                 260

AAG CTG ATG GTG GAT TTC TTC AAC ATT TTG AAT GAG ATT GTA ATG AAG    870
Lys Leu Met Val Asp Phe Phe Asn Ile Leu Asn Glu Ile Val Met Lys
    265                 270                 275

TTA GTG ATC ATG ATC ATG TGG TAC TCT CCC CTG GGT ATC GCC TGC CTG    918
Leu Val Ile Met Ile Met Trp Tyr Ser Pro Leu Gly Ile Ala Cys Leu
280                 285                 290                 295

ATC TGT GGA AAG ATC ATT GCA ATC AAG GAC TTA GAA GTG GTT GCT AGG    966
Ile Cys Gly Lys Ile Ile Ala Ile Lys Asp Leu Glu Val Val Ala Arg
                300                 305                 310

CAA CTG GGG ATG TAC ATG GTA ACA GTG ATC ATA GGC CTC ATC ATC CAC   1014
Gln Leu Gly Met Tyr Met Val Thr Val Ile Ile Gly Leu Ile Ile His
            315                 320                 325

GGG GGC ATC TTT CTC CCC TTG ATT TAC TTT GTA GTG ACC AGG AAA AAC   1062
Gly Gly Ile Phe Leu Pro Leu Ile Tyr Phe Val Val Thr Arg Lys Asn
        330                 335                 340

CCC TTC TCC CTT TTT GCT GGC ATT TTC CAA GCT TGG ATC ACT GCC CTG   1110
Pro Phe Ser Leu Phe Ala Gly Ile Phe Gln Ala Trp Ile Thr Ala Leu
    345                 350                 355

GGC ACC GCT TCC AGT GCT GGA ACT TTG CCT GTC ACC TTT CGT TGC CTG   1158
Gly Thr Ala Ser Ser Ala Gly Thr Leu Pro Val Thr Phe Arg Cys Leu
360                 365                 370                 375

GAA GAA AAT CTG GGG ATT GAT AAG CGT GTG ACT AGA TTC GTC CTT CCT   1206
Glu Glu Asn Leu Gly Ile Asp Lys Arg Val Thr Arg Phe Val Leu Pro
                380                 385                 390

GTT GGA GCA ACC ATT AAC ATG GAT GGT ACA GCC CTT TAT GAA GCG GTG   1254
Val Gly Ala Thr Ile Asn Met Asp Gly Thr Ala Leu Tyr Glu Ala Val
            395                 400                 405

GCC GCC ATC TTT ATA GCC CAA ATG AAT GGT GTT GTC CTG GAT GGA GGA   1302
Ala Ala Ile Phe Ile Ala Gln Met Asn Gly Val Val Leu Asp Gly Gly
        410                 415                 420

CAG ATT GTG ACT GTA AGC CTC ACA GCC ACC CTG GCA AGC GTC GGC GCG   1350
Gln Ile Val Thr Val Ser Leu Thr Ala Thr Leu Ala Ser Val Gly Ala
    425                 430                 435

GCC AGT ATC CCC AGT GCC GGG CTG GTC ACC ATG CTC CTC ATT CTG ACA   1398
Ala Ser Ile Pro Ser Ala Gly Leu Val Thr Met Leu Leu Ile Leu Thr
440                 445                 450                 455

GCC GTG GGC CTG CCA ACA GAG GAC ATC AGC TTG CTG GTG GCT GTG GAC   1446
Ala Val Gly Leu Pro Thr Glu Asp Ile Ser Leu Leu Val Ala Val Asp
                460                 465                 470

TGG CTG CTG GAC AGG ATG AGA ACT TCA GTC AAT GTT GTG GGT GAC TCT   1494
Trp Leu Leu Asp Arg Met Arg Thr Ser Val Asn Val Val Gly Asp Ser
            475                 480                 485

TTT GGG GCT GGG ATA GTC TAT CAC CTC TCC AAG TCT GAG CTG GAT ACC   1542
Phe Gly Ala Gly Ile Val Tyr His Leu Ser Lys Ser Glu Leu Asp Thr
        490                 495                 500

ATT GAC TCC CAG CAT CGA GTG CAT GAA GAT ATT GAA ATG ACC AAG ACT   1590
```

|  |  |  |  |  |  |  |  |  |  |  |  |
|---|---|---|---|---|---|---|---|---|---|---|---|
| Ile | Asp | Ser | Gln | His | Arg | Val | His | Glu | Asp | Ile | Glu | Met | Thr | Lys | Thr |
| 505 |  |  |  |  | 510 |  |  |  |  | 515 |  |  |  |  |  |

| CAA | TCC | ATT | TAT | GAT | GAC | ATG | AAG | AAC | CAC | AGG | GAA | AGC | AAC | TCT | AAT | 1638 |
| Gln | Ser | Ile | Tyr | Asp | Asp | Met | Lys | Asn | His | Arg | Glu | Ser | Asn | Ser | Asn |
| 520 | | | | | 525 | | | | | 530 | | | | | 535 |

| CAA | TGT | GTC | TAT | GCT | GCA | CAC | AAC | TCT | GTC | ATA | GTA | GAT | GAA | TGC | AAG | 1686 |
| Gln | Cys | Val | Tyr | Ala | Ala | His | Asn | Ser | Val | Ile | Val | Asp | Glu | Cys | Lys |
| | | | | 540 | | | | | 545 | | | | | 550 | |

| GTA | ACT | CTG | GCA | GCC | AAT | GGA | AAG | TCA | GCC | GAC | TGC | AGT | GTT | GAG | GAA | 1734 |
| Val | Thr | Leu | Ala | Ala | Asn | Gly | Lys | Ser | Ala | Asp | Cys | Ser | Val | Glu | Glu |
| | | | 555 | | | | | 560 | | | | | 565 | | |

| GAA | CCT | TGG | AAA | CGT | GAG | AAA | TAAGGATATG | AGTCTCAGCA | AATTCTTGAA | 1785 |
| Glu | Pro | Trp | Lys | Arg | Glu | Lys |
| | | | | | 570 | |

TAAACTCCCC AGCGT                                                1800

(2) INFORMATION FOR SEQ ID NO:7:

(i) SEQUENCE CHARACTERISTICS:
        (A) LENGTH: 574 amino acids
        (B) TYPE: amino acid
        (D) TOPOLOGY: linear (ii) MOLECULE TYPE: protein (xi) SEQUENCE DESCRIPTION: SEQ ID NO:7:

| Met | Ala | Ser | Thr | Glu | Gly | Ala | Asn | Asn | Met | Pro | Lys | Gln | Val | Glu | Val |
| 1 | | | | 5 | | | | | 10 | | | | | 15 | |

| Arg | Met | Pro | Asp | Ser | His | Leu | Gly | Ser | Glu | Glu | Pro | Lys | His | Arg | His |
| | | | 20 | | | | | 25 | | | | | 30 | | |

| Leu | Gly | Leu | Arg | Leu | Cys | Asp | Lys | Leu | Gly | Lys | Asn | Leu | Leu | Leu | Thr |
| | | | 35 | | | | | 40 | | | | | 45 | | |

| Leu | Thr | Val | Phe | Gly | Val | Ile | Leu | Gly | Ala | Val | Cys | Gly | Gly | Leu | Leu |
| | 50 | | | | | 55 | | | | | | 60 | | | |

| Arg | Leu | Ala | Ser | Pro | Ile | His | Pro | Asp | Val | Val | Met | Leu | Ile | Ala | Phe |
| 65 | | | | | 70 | | | | | 75 | | | | | 80 |

| Pro | Gly | Asp | Ile | Leu | Met | Arg | Met | Leu | Lys | Met | Leu | Ile | Leu | Gly | Leu |
| | | | | 85 | | | | | 90 | | | | | 95 | |

| Ile | Ile | Ser | Ser | Leu | Ile | Thr | Gly | Leu | Ser | Gly | Leu | Asp | Ala | Lys | Ala |
| | | | 100 | | | | | 105 | | | | | 110 | | |

| Ser | Gly | Arg | Leu | Gly | Thr | Arg | Ala | Met | Val | Tyr | Tyr | Met | Ser | Thr | Thr |
| | | | 115 | | | | | 120 | | | | | 125 | | |

| Ile | Ile | Ala | Ala | Val | Leu | Gly | Val | Ile | Leu | Val | Leu | Ala | Ile | His | Pro |
| | 130 | | | | | 135 | | | | | 140 | | | | |

| Gly | Asn | Pro | Lys | Leu | Lys | Lys | Gln | Leu | Gly | Pro | Gly | Lys | Lys | Asn | Asp |
| 145 | | | | | 150 | | | | | 155 | | | | | 160 |

| Glu | Val | Ser | Ser | Leu | Asp | Ala | Phe | Leu | Asp | Leu | Ile | Arg | Asn | Leu | Phe |
| | | | | 165 | | | | | 170 | | | | | 175 | |

| Pro | Glu | Asn | Leu | Val | Gln | Ala | Cys | Phe | Gln | Gln | Ile | Gln | Thr | Val | Thr |
| | | | 180 | | | | | 185 | | | | | 190 | | |

| Lys | Lys | Val | Leu | Val | Ala | Pro | Pro | Asp | Glu | Glu | Ala | Asn | Ala | Thr |
| | | | 195 | | | | | 200 | | | | | 205 | |

| Ser | Ala | Glu | Val | Ser | Leu | Leu | Asn | Glu | Thr | Val | Thr | Glu | Val | Pro | Glu |
| | 210 | | | | | 215 | | | | | 220 | | | | |

| Glu | Thr | Lys | Met | Val | Ile | Lys | Lys | Gly | Leu | Glu | Phe | Lys | Asp | Gly | Met |
| 225 | | | | | 230 | | | | | 235 | | | | | 240 |

| Asn | Val | Leu | Gly | Leu | Ile | Gly | Phe | Phe | Ile | Ala | Phe | Gly | Ile | Ala | Met |
| | | | | 245 | | | | | 250 | | | | | 255 | |

```
Gly Lys Met Gly Asp Gln Ala Lys Leu Met Val Asp Phe Phe Asn Ile
            260                 265                 270

Leu Asn Glu Ile Val Met Lys Leu Val Ile Met Ile Met Trp Tyr Ser
        275                 280                 285

Pro Leu Gly Ile Ala Cys Leu Ile Cys Gly Lys Ile Ile Ala Ile Lys
        290                 295                 300

Asp Leu Glu Val Val Ala Arg Gln Leu Gly Met Tyr Met Val Thr Val
305                     310                 315                 320

Ile Ile Gly Leu Ile Ile His Gly Gly Ile Phe Leu Pro Leu Ile Tyr
                325                 330                 335

Phe Val Val Thr Arg Lys Asn Pro Phe Ser Leu Phe Ala Gly Ile Phe
            340                 345                 350

Gln Ala Trp Ile Thr Ala Leu Gly Thr Ala Ser Ser Ala Gly Thr Leu
            355                 360                 365

Pro Val Thr Phe Arg Cys Leu Glu Glu Asn Leu Gly Ile Asp Lys Arg
        370                 375                 380

Val Thr Arg Phe Val Leu Pro Val Gly Ala Thr Ile Asn Met Asp Gly
385                     390                 395                 400

Thr Ala Leu Tyr Glu Ala Val Ala Ala Ile Phe Ile Ala Gln Met Asn
                405                 410                 415

Gly Val Val Leu Asp Gly Gly Gln Ile Val Thr Val Ser Leu Thr Ala
            420                 425                 430

Thr Leu Ala Ser Val Gly Ala Ala Ser Ile Pro Ser Ala Gly Leu Val
        435                 440                 445

Thr Met Leu Leu Ile Leu Thr Ala Val Gly Leu Pro Thr Glu Asp Ile
    450                 455                 460

Ser Leu Leu Val Ala Val Asp Trp Leu Leu Asp Arg Met Arg Thr Ser
465                 470                 475                 480

Val Asn Val Val Gly Asp Ser Phe Gly Ala Gly Ile Val Tyr His Leu
                485                 490                 495

Ser Lys Ser Glu Leu Asp Thr Ile Asp Ser Gln His Arg Val His Glu
            500                 505                 510

Asp Ile Glu Met Thr Lys Thr Gln Ser Ile Tyr Asp Asp Met Lys Asn
        515                 520                 525

His Arg Glu Ser Asn Ser Asn Gln Cys Val Tyr Ala Ala His Asn Ser
    530                 535                 540

Val Ile Val Asp Glu Cys Lys Val Thr Leu Ala Ala Asn Gly Lys Ser
545                 550                 555                 560

Ala Asp Cys Ser Val Glu Glu Glu Pro Trp Lys Arg Glu Lys
                565                 570
```

( 2 ) INFORMATION FOR SEQ ID NO:8:

( i ) SEQUENCE CHARACTERISTICS:
        ( A ) LENGTH: 1674 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: 5'UTR
        ( B ) LOCATION: 1..15

( i x ) FEATURE:
        ( A ) NAME/KEY: CDS
        ( B ) LOCATION: 16..1590

( i x ) FEATURE:
    ( A ) NAME/KEY: 3'UTR
    ( B ) LOCATION: 1591..1674

( x i ) SEQUENCE DESCRIPTION: SEQ ID NO:8:

| | | | | | | | | | | | | | | | | |
|---|---|---|---|---|---|---|---|---|---|---|---|---|---|---|---|---|
| ATAGCGGCGA | CAGCC | ATG | GGG | AAA | CCG | GCG | AGG | AAA | GGA | TGC | CCG | AGT | TGG | | | 51 |
| | | Met | Gly | Lys | Pro | Ala | Arg | Lys | Gly | Cys | Pro | Ser | Trp | | | |
| | | 1 | | 5 | | | | | | 10 | | | | | | |
| AAG | CGC | TTC | CTG | AAG | AAT | AAC | TGG | GTG | TTG | CTG | TCC | ACC | GTG | GCC | GCG | 99 |
| Lys | Arg | Phe | Leu | Lys | Asn | Asn | Trp | Val | Leu | Leu | Ser | Thr | Val | Ala | Ala | |
| | | 15 | | | | 20 | | | | | 25 | | | | | |
| GTG | GTG | CTA | GGC | ATT | ACC | ACA | GGA | GTC | TTG | GTT | CGA | GAA | CAC | AGC | AAC | 147 |
| Val | Val | Leu | Gly | Ile | Thr | Thr | Gly | Val | Leu | Val | Arg | Glu | His | Ser | Asn | |
| | 30 | | | | | 35 | | | | | 40 | | | | | |
| CTC | TCA | ACT | CTA | GAG | AAA | TTC | TAC | TTT | GCT | TTT | CCT | GGA | GAA | ATT | CTA | 195 |
| Leu | Ser | Thr | Leu | Glu | Lys | Phe | Tyr | Phe | Ala | Phe | Pro | Gly | Glu | Ile | Leu | |
| 45 | | | | | 50 | | | | | 55 | | | | | 60 | |
| ATG | CGG | ATG | CTG | AAA | CTC | ATC | ATT | TTG | CCA | TTA | ATT | ATA | TCC | AGC | ATG | 243 |
| Met | Arg | Met | Leu | Lys | Leu | Ile | Ile | Leu | Pro | Leu | Ile | Ile | Ser | Ser | Met | |
| | | | | 65 | | | | | 70 | | | | | 75 | | |
| ATT | ACA | GGT | GTT | GCT | GCA | CTG | GAT | TCC | AAC | GTA | TCC | GGA | AAA | ATT | GGT | 291 |
| Ile | Thr | Gly | Val | Ala | Ala | Leu | Asp | Ser | Asn | Val | Ser | Gly | Lys | Ile | Gly | |
| | | | 80 | | | | | 85 | | | | | 90 | | | |
| CTG | CGC | GCT | GTC | GTG | TAT | TAT | TTC | TGT | ACC | ACT | CTC | ATT | GCT | GTT | ATT | 339 |
| Leu | Arg | Ala | Val | Val | Tyr | Tyr | Phe | Cys | Thr | Thr | Leu | Ile | Ala | Val | Ile | |
| | | 95 | | | | 100 | | | | | 105 | | | | | |
| CTA | GGT | ATT | GTG | CTG | GTG | GTG | AGC | ATC | AAG | CCT | GGT | GTC | ACC | CAG | AAA | 387 |
| Leu | Gly | Ile | Val | Leu | Val | Val | Ser | Ile | Lys | Pro | Gly | Val | Thr | Gln | Lys | |
| | 110 | | | | | 115 | | | | | 120 | | | | | |
| GTG | GGT | GAA | ATT | GCG | AGG | ACA | GGC | AGC | ACC | CCT | GAA | GTC | AGT | ACG | GTG | 435 |
| Val | Gly | Glu | Ile | Ala | Arg | Thr | Gly | Ser | Thr | Pro | Glu | Val | Ser | Thr | Val | |
| 125 | | | | | 130 | | | | | 135 | | | | | 140 | |
| GAT | GCC | ATG | TTA | GAT | CTC | ATC | AGG | AAT | ATG | TTC | CCT | GAG | AAT | CTT | GTC | 483 |
| Asp | Ala | Met | Leu | Asp | Leu | Ile | Arg | Asn | Met | Phe | Pro | Glu | Asn | Leu | Val | |
| | | | | 145 | | | | | 150 | | | | | 155 | | |
| CAG | GCC | TGT | TTT | CAG | CAG | TAC | AAA | ACT | AAG | CGT | GAA | GAA | GTG | AAG | CCT | 531 |
| Gln | Ala | Cys | Phe | Gln | Gln | Tyr | Lys | Thr | Lys | Arg | Glu | Glu | Val | Lys | Pro | |
| | | | 160 | | | | | 165 | | | | | 170 | | | |
| CCC | AGC | GAT | CCA | GAG | ATG | AAC | ATG | ACA | GAA | GAG | TCC | TTC | ACA | GCT | GTC | 579 |
| Pro | Ser | Asp | Pro | Glu | Met | Asn | Met | Thr | Glu | Glu | Ser | Phe | Thr | Ala | Val | |
| | | 175 | | | | 180 | | | | | 185 | | | | | |
| ATG | ACA | ACT | GCA | ATT | TCC | AAG | AAC | AAA | ACA | AAG | GAA | TAC | AAA | ATT | GTT | 627 |
| Met | Thr | Thr | Ala | Ile | Ser | Lys | Asn | Lys | Thr | Lys | Glu | Tyr | Lys | Ile | Val | |
| | 190 | | | | | 195 | | | | | 200 | | | | | |
| GGC | ATG | TAT | TCA | GAT | GGC | ATA | AAC | GTC | CTG | GGC | TTG | ATT | GTC | TTT | TGC | 675 |
| Gly | Met | Tyr | Ser | Asp | Gly | Ile | Asn | Val | Leu | Gly | Leu | Ile | Val | Phe | Cys | |
| 205 | | | | | 210 | | | | | 215 | | | | | 220 | |
| CTT | GTC | TTT | GGA | CTT | GTC | ATT | GGA | AAA | ATG | GGA | GAA | AAG | GGA | CAA | ATT | 723 |
| Leu | Val | Phe | Gly | Leu | Val | Ile | Gly | Lys | Met | Gly | Glu | Lys | Gly | Gln | Ile | |
| | | | | 225 | | | | | 230 | | | | | 235 | | |
| CTG | GTG | GAT | TTC | TTC | AAT | GCT | TTG | AGT | GAT | GCA | ACC | ATG | AAA | ATC | GTT | 771 |
| Leu | Val | Asp | Phe | Phe | Asn | Ala | Leu | Ser | Asp | Ala | Thr | Met | Lys | Ile | Val | |
| | | | 240 | | | | | 245 | | | | | 250 | | | |
| CAG | ATC | ATC | ATG | TGT | TAT | ATG | CCA | CTA | GGT | ATT | TTG | TTC | CTG | ATT | GCT | 819 |
| Gln | Ile | Ile | Met | Cys | Tyr | Met | Pro | Leu | Gly | Ile | Leu | Phe | Leu | Ile | Ala | |
| | | 255 | | | | | 260 | | | | | 265 | | | | |
| GGG | AAG | ATC | ATA | GAA | GTT | GAA | GAC | TGG | GAA | ATA | TTC | CGC | AAG | CTG | GGC | 867 |
| Gly | Lys | Ile | Ile | Glu | Val | Glu | Asp | Trp | Glu | Ile | Phe | Arg | Lys | Leu | Gly | |
| | 270 | | | | | 275 | | | | | 280 | | | | | |
| CTT | TAC | ATG | GCC | ACA | GTC | CTG | ACT | GGG | CTT | GCA | ATC | CAC | TCC | ATT | GTA | 915 |

|  |  |  |  |  |  |  |  |  |  |  |  |  |  |  |  |
|---|---|---|---|---|---|---|---|---|---|---|---|---|---|---|---|
| Leu | Tyr | Met | Ala | Thr | Val | Leu | Thr | Gly | Leu | Ala | Ile | His | Ser | Ile | Val |
| 285 |  |  |  |  | 290 |  |  |  | 295 |  |  |  |  |  | 300 |

| ATT | CTC | CCG | CTG | ATA | TAT | TTC | ATA | GTC | GTA | CGA | AAG | AAC | CCT | TTC | CGA | 963 |
|---|---|---|---|---|---|---|---|---|---|---|---|---|---|---|---|---|
| Ile | Leu | Pro | Leu | Ile | Tyr | Phe | Ile | Val | Val | Arg | Lys | Asn | Pro | Phe | Arg |  |
|  |  |  |  | 305 |  |  |  |  | 310 |  |  |  |  | 315 |  |  |

| TTT | GCC | ATG | GGA | ATG | GCC | CAG | GCT | CTC | CTG | ACA | GCT | CTC | ATG | ATC | TCT | 1011 |
|---|---|---|---|---|---|---|---|---|---|---|---|---|---|---|---|---|
| Phe | Ala | Met | Gly | Met | Ala | Gln | Ala | Leu | Leu | Thr | Ala | Leu | Met | Ile | Ser |  |
|  |  |  | 320 |  |  |  |  |  | 325 |  |  |  | 330 |  |  |  |

| TCC | AGT | TCA | GCA | ACA | CTG | CCT | GTC | ACC | TTC | CGC | TGT | GCT | GAA | GAA | AAT | 1059 |
|---|---|---|---|---|---|---|---|---|---|---|---|---|---|---|---|---|
| Ser | Ser | Ser | Ala | Thr | Leu | Pro | Val | Thr | Phe | Arg | Cys | Ala | Glu | Glu | Asn |  |
|  |  | 335 |  |  |  |  | 340 |  |  |  |  | 345 |  |  |  |  |

| AAC | CAG | GTG | GAC | AAG | AGG | ATC | ACT | CGA | TTC | GTG | TTA | CCC | GTT | GGT | GCA | 1107 |
|---|---|---|---|---|---|---|---|---|---|---|---|---|---|---|---|---|
| Asn | Gln | Val | Asp | Lys | Arg | Ile | Thr | Arg | Phe | Val | Leu | Pro | Val | Gly | Ala |  |
|  | 350 |  |  |  |  | 355 |  |  |  |  | 360 |  |  |  |  |  |

| ACA | ATC | AAC | ATG | GAT | GGG | ACC | GCG | CTC | TAT | GAA | GCA | GTG | GCA | GCG | GTG | 1155 |
|---|---|---|---|---|---|---|---|---|---|---|---|---|---|---|---|---|
| Thr | Ile | Asn | Met | Asp | Gly | Thr | Ala | Leu | Tyr | Glu | Ala | Val | Ala | Ala | Val |  |
| 365 |  |  |  |  | 370 |  |  |  |  | 375 |  |  |  |  | 380 |  |

| TTT | ATT | GCA | CAG | TTG | AAT | GAC | CTG | GAC | TTG | GGC | ATT | GGG | CAG | ATC | ATC | 1203 |
|---|---|---|---|---|---|---|---|---|---|---|---|---|---|---|---|---|
| Phe | Ile | Ala | Gln | Leu | Asn | Asp | Leu | Asp | Leu | Gly | Ile | Gly | Gln | Ile | Ile |  |
|  |  |  |  |  | 385 |  |  |  |  | 390 |  |  |  |  | 395 |  |

| ACC | ATC | AGT | ATC | ACG | GCC | ACA | TCT | GCC | AGC | ATC | GGA | GCT | GCT | GGC | GTG | 1251 |
|---|---|---|---|---|---|---|---|---|---|---|---|---|---|---|---|---|
| Thr | Ile | Ser | Ile | Thr | Ala | Thr | Ser | Ala | Ser | Ile | Gly | Ala | Ala | Gly | Val |  |
|  |  |  | 400 |  |  |  |  | 405 |  |  |  |  | 410 |  |  |  |

| CCC | CAG | GCT | GGC | CTG | GTG | ACC | ATG | GTG | ATT | GTG | CTG | AGT | GCC | GTG | GGC | 1299 |
|---|---|---|---|---|---|---|---|---|---|---|---|---|---|---|---|---|
| Pro | Gln | Ala | Gly | Leu | Val | Thr | Met | Val | Ile | Val | Leu | Ser | Ala | Val | Gly |  |
|  |  | 415 |  |  |  |  | 420 |  |  |  |  | 425 |  |  |  |  |

| CTG | CCC | GCC | GAG | GAT | GTC | ACC | CTG | ATC | ATT | GCT | GTC | GAC | TGG | CTC | CTG | 1347 |
|---|---|---|---|---|---|---|---|---|---|---|---|---|---|---|---|---|
| Leu | Pro | Ala | Glu | Asp | Val | Thr | Leu | Ile | Ile | Ala | Val | Asp | Trp | Leu | Leu |  |
| 430 |  |  |  |  |  | 435 |  |  |  |  | 440 |  |  |  |  |  |

| GAC | CGG | TTC | AGG | ACC | ATG | GTC | AAC | GTC | CTT | GGT | GAT | GCT | TTT | GGG | ACG | 1395 |
|---|---|---|---|---|---|---|---|---|---|---|---|---|---|---|---|---|
| Asp | Arg | Phe | Arg | Thr | Met | Val | Asn | Val | Leu | Gly | Asp | Ala | Phe | Gly | Thr |  |
| 445 |  |  |  |  | 450 |  |  |  |  | 455 |  |  |  |  | 460 |  |

| GGC | ATT | GTG | GAA | AAG | CTC | TCC | AAG | AAG | GAG | CTG | GAG | CAG | ATG | GAT | GTT | 1443 |
|---|---|---|---|---|---|---|---|---|---|---|---|---|---|---|---|---|
| Gly | Ile | Val | Glu | Lys | Leu | Ser | Lys | Lys | Glu | Leu | Glu | Gln | Met | Asp | Val |  |
|  |  |  |  | 465 |  |  |  |  | 470 |  |  |  |  | 475 |  |  |

| TCA | TCT | GAA | GTC | AAC | ATT | GTG | AAT | CCC | TTT | GCC | TTG | GAA | TCC | ACA | ATC | 1491 |
|---|---|---|---|---|---|---|---|---|---|---|---|---|---|---|---|---|
| Ser | Ser | Glu | Val | Asn | Ile | Val | Asn | Pro | Phe | Ala | Leu | Glu | Ser | Thr | Ile |  |
|  |  |  | 480 |  |  |  |  | 485 |  |  |  |  | 490 |  |  |  |

| CTT | GAC | AAC | GAA | GAC | TCA | GAC | ACC | AAG | AAG | TCT | TAT | GTC | AAT | GGA | GGC | 1539 |
|---|---|---|---|---|---|---|---|---|---|---|---|---|---|---|---|---|
| Leu | Asp | Asn | Glu | Asp | Ser | Asp | Thr | Lys | Lys | Ser | Tyr | Val | Asn | Gly | Gly |  |
|  |  | 495 |  |  |  |  | 500 |  |  |  |  | 505 |  |  |  |  |

| TTT | GCA | GTA | GAC | AAG | TCT | GAC | ACC | ATC | TCA | TTC | ACC | CAG | ACC | TCA | CAG | 1587 |
|---|---|---|---|---|---|---|---|---|---|---|---|---|---|---|---|---|
| Phe | Ala | Val | Asp | Lys | Ser | Asp | Thr | Ile | Ser | Phe | Thr | Gln | Thr | Ser | Gln |  |
| 510 |  |  |  |  | 515 |  |  |  |  | 520 |  |  |  |  |  |  |

| TTC | TAGGGCCCCT | GGCTGCAGAT | GACTGGAAAC | AAGGAAGGAC | ATTTCGTGAG | 1640 |
|---|---|---|---|---|---|---|
| Phe |  |  |  |  |  |  |
| 525 |  |  |  |  |  |  |

AGTCATCTCA AACACGGCTT AAGGAAAAGA GAAA                      1674

( 2 ) INFORMATION FOR SEQ ID NO:9:

( i ) SEQUENCE CHARACTERISTICS:
        ( A ) LENGTH: 525 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Met | Gly | Lys | Pro | Ala | Arg | Lys | Gly | Cys | Pro | Ser | Trp | Lys | Arg | Phe | Leu |
|---|---|---|---|---|---|---|---|---|---|---|---|---|---|---|---|
| 1 |  |  |  | 5 |  |  |  |  | 10 |  |  |  |  | 15 |  |

| | | | | | | | | | | | | | | |
|---|---|---|---|---|---|---|---|---|---|---|---|---|---|---|
|Lys|Asn|Asn|Trp|Val|Leu|Leu|Ser|Thr|Val|Ala|Ala|Val|Val|Leu|Gly|
| | | |20| | | |25| | | |30| | | |
|Ile|Thr|Thr|Gly|Val|Leu|Val|Arg|Glu|His|Ser|Asn|Leu|Ser|Thr|Leu|
| | |35| | | |40| | | |45| | | | |
|Glu|Lys|Phe|Tyr|Phe|Ala|Phe|Pro|Gly|Glu|Ile|Leu|Met|Arg|Met|Leu|
| |50| | | |55| | | | |60| | | | |
|Lys|Leu|Ile|Ile|Leu|Pro|Leu|Ile|Ile|Ser|Ser|Met|Ile|Thr|Gly|Val|
|65| | | |70| | | |75| | | | | |80|
|Ala|Ala|Leu|Asp|Ser|Asn|Val|Ser|Gly|Lys|Ile|Gly|Leu|Arg|Ala|Val|
| | | |85| | | |90| | | | | |95| |
|Val|Tyr|Tyr|Phe|Cys|Thr|Thr|Leu|Ile|Ala|Val|Ile|Leu|Gly|Ile|Val|
| | |100| | | |105| | | |110| | | | |
|Leu|Val|Val|Ser|Ile|Lys|Pro|Gly|Val|Thr|Gln|Lys|Val|Gly|Glu|Ile|
| |115| | | |120| | | |125| | | | | |
|Ala|Arg|Thr|Gly|Ser|Thr|Pro|Glu|Val|Ser|Thr|Val|Asp|Ala|Met|Leu|
|130| | | |135| | | |140| | | | | | |
|Asp|Leu|Ile|Arg|Asn|Met|Phe|Pro|Glu|Asn|Leu|Val|Gln|Ala|Cys|Phe|
|145| | | |150| | | |155| | | |160| | |
|Gln|Gln|Tyr|Lys|Thr|Lys|Arg|Glu|Glu|Val|Lys|Pro|Pro|Ser|Asp|Pro|
| | | |165| | | |170| | | | |175| | |
|Glu|Met|Asn|Met|Thr|Glu|Glu|Ser|Phe|Thr|Ala|Val|Met|Thr|Thr|Ala|
| | |180| | | |185| | | |190| | | | |
|Ile|Ser|Lys|Asn|Lys|Thr|Lys|Glu|Tyr|Lys|Ile|Val|Gly|Met|Tyr|Ser|
| |195| | | |200| | | |205| | | | | |
|Asp|Gly|Ile|Asn|Val|Leu|Gly|Leu|Ile|Val|Phe|Cys|Leu|Val|Phe|Gly|
|210| | | |215| | | |220| | | | | | |
|Leu|Val|Ile|Gly|Lys|Met|Gly|Glu|Lys|Gly|Gln|Ile|Leu|Val|Asp|Phe|
|225| | | |230| | | |235| | | | |240| |
|Phe|Asn|Ala|Leu|Ser|Asp|Ala|Thr|Met|Lys|Ile|Val|Gln|Ile|Ile|Met|
| | | |245| | | |250| | | | |255| | |
|Cys|Tyr|Met|Pro|Leu|Gly|Ile|Leu|Phe|Leu|Ile|Ala|Gly|Lys|Ile|Ile|
| | |260| | | |265| | | |270| | | | |
|Glu|Val|Glu|Asp|Trp|Glu|Ile|Phe|Arg|Lys|Leu|Gly|Leu|Tyr|Met|Ala|
| |275| | | |280| | | |285| | | | | |
|Thr|Val|Leu|Thr|Gly|Leu|Ala|Ile|His|Ser|Ile|Val|Ile|Leu|Pro|Leu|
|290| | | |295| | | |300| | | | | | |
|Ile|Tyr|Phe|Ile|Val|Val|Arg|Lys|Asn|Pro|Phe|Arg|Phe|Ala|Met|Gly|
|305| | | |310| | | |315| | | |320| | |
|Met|Ala|Gln|Ala|Leu|Leu|Thr|Ala|Leu|Met|Ile|Ser|Ser|Ser|Ala|
| | | |325| | | |330| | | |335| | | |
|Thr|Leu|Pro|Val|Thr|Phe|Arg|Cys|Ala|Glu|Glu|Asn|Asn|Gln|Val|Asp|
| | |340| | | |345| | | |350| | | | |
|Lys|Arg|Ile|Thr|Arg|Phe|Val|Leu|Pro|Val|Gly|Ala|Thr|Ile|Asn|Met|
| |355| | | |360| | | |365| | | | | |
|Asp|Gly|Thr|Ala|Leu|Tyr|Glu|Ala|Val|Ala|Ala|Val|Phe|Ile|Ala|Gln|
|370| | | |375| | | |380| | | | | | |
|Leu|Asn|Asp|Leu|Asp|Leu|Gly|Ile|Gly|Gln|Ile|Ile|Thr|Ile|Ser|Ile|
|385| | | |390| | | |395| | | | |400| |
|Thr|Ala|Thr|Ser|Ala|Ser|Ile|Gly|Ala|Ala|Gly|Val|Pro|Gln|Ala|Gly|
| | | |405| | | |410| | | | |415| | |
|Leu|Val|Thr|Met|Val|Ile|Val|Leu|Ser|Ala|Val|Gly|Leu|Pro|Ala|Glu|
| | |420| | | |425| | | |430| | | | |
|Asp|Val|Thr|Leu|Ile|Ile|Ala|Val|Asp|Trp|Leu|Leu|Asp|Arg|Phe|Arg|

|   | 435 |   |   |   | 440 |   |   |   | 445 |   |   |   |
|---|---|---|---|---|---|---|---|---|---|---|---|---|

Thr Met Val Asn Val Leu Gly Asp Ala Phe Gly Thr Gly Ile Val Glu
    450                                455                           460

Lys Leu Ser Lys Lys Glu Leu Glu Gln Met Asp Val Ser Ser Glu Val
465                         470                        475                        480

Asn Ile Val Asn Pro Phe Ala Leu Glu Ser Thr Ile Leu Asp Asn Glu
                485                        490                        495

Asp Ser Asp Thr Lys Lys Ser Tyr Val Asn Gly Gly Phe Ala Val Asp
        500                       505                    510

Lys Ser Asp Thr Ile Ser Phe Thr Gln Thr Ser Gln Phe
      515                      520                    525

( 2 ) INFORMATION FOR SEQ ID NO:10:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CGCGGGTACC GCCATGGAGA AGAGCAAC                            28

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CGCGTCTAGA TCACAGAACC GACTCCTTG                        29

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CGCGGGTACC AATATGACTA AAAGCAATG                         29

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CGCGTCTAGA CTACATCTTG GTTTCACTG                        29

( 2 ) INFORMATION FOR SEQ ID NO:14:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:14:

CGCGGGTACC ACCATGGCAT CTACGGAAG 29

( 2 ) INFORMATION FOR SEQ ID NO:15:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:15:

CGCGTCTAGA TTATTTCTCA CGTTTCCAAG 30

( 2 ) INFORMATION FOR SEQ ID NO:16:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:16:

CGCGGGTACC GCCATGGGGA AACCGGCG 28

( 2 ) INFORMATION FOR SEQ ID NO:17:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:17:

CGCGGGATCC CTAGAACTGT GAGGTCTG 28